US 8,591,878 B2

(12) United States Patent
McCauley et al.

(10) Patent No.: US 8,591,878 B2
(45) Date of Patent: *Nov. 26, 2013

(54) THERAPEUTIC COMPOUNDS

(75) Inventors: John A. McCauley, Maple Glen, PA (US); Nigel J. Liverton, Harleysville, PA (US); Steven Harper, Rome (IT); Charles J. McIntyre, Landsdale, PA (US); Michael T. Rudd, Collegeville, PA (US)

(73) Assignees: Merck Sharp & Dohme Corp., Rahway, NJ (US); Istituto di Ricerche di Biologia Molecolare P. Angeletti Spa, Rome (IT)

( * ) Notice: Subject to any disclaimer, the term of this patent is extended or adjusted under 35 U.S.C. 154(b) by 339 days.

This patent is subject to a terminal disclaimer.

(21) Appl. No.: 12/919,128

(22) PCT Filed: Feb. 12, 2009

(86) PCT No.: PCT/US2009/033859
§ 371 (c)(1),
(2), (4) Date: Aug. 24, 2010

(87) PCT Pub. No.: WO2009/108507
PCT Pub. Date: Sep. 3, 2009

(65) Prior Publication Data
US 2011/0002884 A1   Jan. 6, 2011

Related U.S. Application Data

(60) Provisional application No. 61/067,012, filed on Feb. 25, 2008.

(51) Int. Cl.
A61K 38/21 (2006.01)
A61K 38/12 (2006.01)
C07K 5/12 (2006.01)

(52) U.S. Cl.
USPC ....... 424/85.5; 424/85.6; 424/85.7; 514/21.1; 530/317

(58) Field of Classification Search
None
See application file for complete search history.

(56) References Cited

U.S. PATENT DOCUMENTS

| 2004/0229818 A1 | 11/2004 | Llinas-Brunet |
| 2005/0020503 A1 | 1/2005 | Llinas-Brunet et al. |
| 2010/0099695 A1* | 4/2010 | Liverton et al. ............... 514/281 |

FOREIGN PATENT DOCUMENTS

| WO | WO0009543 A2 | 2/2000 |
| WO | WO0177113 A2 | 10/2001 |
| WO | WO2004093915 A1 | 11/2004 |
| WO | WO2004103996 A1 | 12/2004 |
| WO | WO2006119061 A2 | 11/2006 |
| WO | WO2007015787 A1 | 2/2007 |
| WO | WO2007016441 A1 | 2/2007 |
| WO | WO2008057209 A1 | 5/2008 |

OTHER PUBLICATIONS

Ramamurthy, M.; Muir, A. Treatment of Hepaptitis C in Special Populations. Clin Liver Dis 2006, 10, pp. 851-865.*

* cited by examiner

Primary Examiner — Robert A Wax
Assistant Examiner — Jessica Worsham
(74) Attorney, Agent, or Firm — Melissa B. Wenk; Sheldon O. Heber

(57) ABSTRACT

A class of macrocyclic compounds of formula (I), wherein $R^1$, $R^3$, $R^4$, $R^a$, $R^b$, A, B, Z, M, W and n are defined herein, that are useful as inhibitors of viral proteases, particularly the hepatitis C virus (HCV) NS3 protease, are provided. Also provided are processes for the synthesis and use of such macrocyclic compounds for treating or preventing HCV infection.

26 Claims, No Drawings

THERAPEUTIC COMPOUNDS

CROSS-REFERENCE TO RELATED APPLICATIONS

This application is a National Stage application of International Patent Application No. PCT/US2009/033859, filed Feb. 12, 2009, which claims priority to U.S. Provisional Patent Application No. 61/067,012, filed Feb. 25, 2008.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target because it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. Patent Application Publication Nos. US 2005/0020503, US 2004/0229818, and US 2004/00229776, showing degrees of activity in inhibiting the NS3 protease. The aim of the present invention is to provide further compounds that exhibit activity against the HCV NS3 protease.

Macrocyclic compounds that exhibit activity against the HCV NS3 protease have already been disclosed in International Patent Application Publication Nos. WO 2006/119061, WO 2007/015855 and WO 2007/016441.

SUMMARY OF THE INVENTION

Thus, in one aspect, there is provided the compound of formula (I):

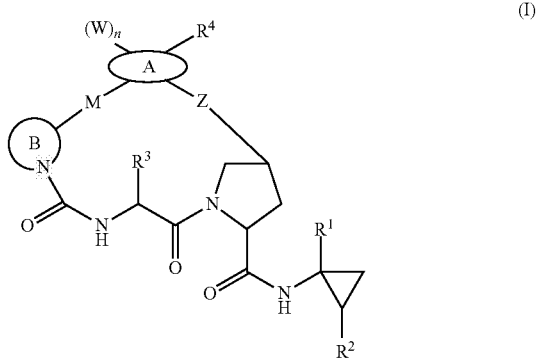

or a pharmaceutically acceptable salt thereof,
wherein:
n is 0, 1 or 2;
$R^1$ is selected from the group consisting of $CO_2R^{10}$, $CONR^{10}SO_2R^6$, $CONR^{10}SO_2NR^8R^9$ and tetrazolyl;
$R^2$ is selected from the group consisting of $C_{1-6}$alkyl, $C_{2-6}$alkenyl and $C_{3-8}$cycloalkyl, wherein said $R^2$ alkyl, alkenyl or cycloalkyl is substituted with 0 to 3 halogens;
$R^3$ is selected from the group consisting of $C_{1-6}$alkyl, $C_{3-8}$cycloalkyl, $C_{3-8}$cycloalkyl($C_{1-8}$)alkyl, aryl($C_{1-8}$) alkyl and Het, wherein said $R^3$ alkyl, cycloalkyl, or aryl is substituted with 0 to 3 substituents selected from the group consisting of halogen, $OR^{10}$, $SR^{10}$, $N(R^{10}SO_2$, $N(C_{1-6}alkyl)O(C_{1-6}alkyl)$, $C_{1-6}$alkyl, $C_{1-6}$haloalkyl, $C_{1-6}$haloalkoxy, $NO_2$, $CN$, $CF_3$, $SO_2(C_{1-6}$alkyl), $S(O)$ $(C_{1-6}$alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$ and $CON(R^{10})_2$;
Het is a 5- to 6-membered saturated cyclic ring having 1 or 2 heteroatoms selected from the group consisting of N, O and S, wherein said ring is substituted with 0 to 3 substituents selected from the group consisting of halogen, $OR^{10}$, $SR^{10}$, $N(R^{10})_2$, $N(C_{1-6}alkyl)O(C_{1-6}alkyl)$, $C_{1-6}$alkyl, $C_{1-6}$haloalkyl, $(C_{1-6}$haloalkoxy), $NO_2$, $CN$, $CF_3$, $SO_2(C_{1-6}$alkyl), $S(O)(C_{1-6}$alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^4$ is selected from the group consisting of H, halogen, OH, $C_{1-6}$alkoxy, $C_{1-6}$alkyl, CN, $CF_3$, $SR^{10}$, $SO_2(C_{1-6}$alkyl), $C_{3-8}$cycloalkyl, $C_{3-8}$cycloalkoxy, $C_{1-6}$haloalkyl, $N(R^7)_2$, aryl, heteroaryl and heterocyclyl; wherein said $R^4$ aryl, heteroaryl, heterocyclyl, cycloalkyl, cycloalkoxy, alkyl or alkoxy is substituted with 0 to 4 substituents selected from the group consisting of halogen, $OR^{10}$, $SR^{10}$, $N(R^7)_2$, $N(C_1alkyl)O(C_{1-6}alkyl)$, $C_{1-6}$alkyl, $C_{1-6}$haloalkyl, $C_{1-6}$haloalkoxy, $C_{3-6}$cycloalkyl, $C_{3-6}$cycloalkoxy, $NO_2$, $CN$, $CF_3$, $SO_2(C_{1-6}$ alkyl), $NR^{10}SO_2R^6$, $SO_2N(R^6)_2$, $S(O)(C_{1-6}$alkyl), $NHCOOR^6$, $NHCOR^6$, $NHCONHR^6$, $CO_2R^{10}$, $C(O)$ $R^{10}$ and $CON(R^{10})_2$; wherein the 2 adjacent substituents of said $R^4$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;
each $R^6$ is independently selected from the group consisting of $C_{1-6}$alkyl, $C_{3-6}$cycloalkyl, $C_{3-6}$cycloalkyl($C_{1-5}$) alkyl, aryl, aryl($C_{1-4}$)alkyl, heteroaryl, heteroaryl($C_{1-4}$ alkyl), heterocyclyl and heterocyclyl($C_{1-8}$alkyl), wherein said $R^6$ alkyl, cycloalkyl, aryl, heteroaryl, or heterocyclyl is substituted with 0 to 2 Q substituents;

each Q is independently selected from the group consisting of halogen, $OR^{10}$, $C_{1-6}$alkyl, CN, $CF_3$, $NO_2$, $SR^{10}$, $CO_2R^{10}$, $CON(R^{10})_2$, $C(O)R^{10})_2N(R^{10})$ $C(O)R^{10}$, $SO_2$($C_{1-6}$alkyl), $S(O)(C_{1-6}$alkyl), $C_{3-8}$cycloalkyl, $C_{3-8}$cycloalkoxy, $C_{1-6}$haloalkyl, $N(R^{10})_2$, $N(C_{1-6}$alkyl)$O(C_{1-6}$ alkyl), ($C_{1-6}$haloalkoxy), $NR^{10}SO_2R^{10}$, $SO_2N(O)_2$, $NHCOOR^{10}$, $NHCONHR^H$), aryl, heteroaryl and heterocyclyl;

each $R^7$ is independently selected from the group consisting of H, $C_{1-6}$alkyl, $C_{3-6}$cycloalkyl, $C_{3-6}$cycloalkyl($C_{1-5}$)alkyl, aryl, aryl($C_{1-4}$alkyl, heteroaryl, heteroaryl($C_{1-4}$alkyl), heterocyclyl and heterocyclyl($C_{1-8}$alkyl), wherein said $R^7$ alkyl, cycloalkyl, aryl, heteroaryl, or heterocyclyl is substituted with 0 to 2 Q substituents;

$R^8$ is selected from the group consisting of $C_{1-8}$alkyl, $C_{3-8}$cycloalkyl, $C_{3-8}$cycloalkyl($C_{1-8}$alkyl), aryl, aryl ($C_{1-4}$ alkyl), heteroaryl, heterocyclyl, heteroaryl($C_{1-4}$ alkyl) and heterocyclyl($C_{1-8}$alkyl), wherein said $R^8$ alkyl, cycloalkyl, aryl, heteroaryl or heterocyclyl is substituted with 0 to 4 substituents selected from the group consisting of aryl, $C_{3-8}$cycloalkyl, heteroaryl, heterocyclyl, $C_{1-6}$alkyl, $C_{1-6}$haloalkoxy, halo, $OR^{10}$, $SR'^o$, $N(R^{10})_2$, $N(C_{1-6}$alkyl)$O(C_{1-6}$ alkyl), $C_{1-6}$alkyl, $C(O)R^{10}$, $C_{1-6}$haloalkyl, $NO_2$, CN, $CF_3$, $SO_2(C_{1-6}$alkyl), $S(O)(C_{1-6}$ alkyl), $NR^{10}SO_2R^6$, $SO_2N(R^6)_2$, $NHCOOR^6$, $NHCOR^6$, $NHCONHR^6$, $CO_2R^{10}$ and $C(O)N(R^{10})_2$; wherein the 2 adjacent substituents of said $R^8$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;

$R^9$ is selected from the group consisting of $C_{1-8}$alkyl, $C_{3-8}$cycloalkyl, $C_{3-8}$cycloalkyl($C_{1-8}$alkyl), $C_{1-8}$alkoxy, $C_{3-8}$cycloalkoxy, aryl, aryl($C_{1-4}$alkyl), heteroaryl, heterocyclyl, heteroaryl($C_{1-4}$alkyl) and heterocyclyl($C_{1-8}$ alkyl), wherein said $R^9$ alkyl, cycloalkyl, alkoxy, cycloalkoxy, aryl, heteroaryl or heterocyclyl is substituted with 0 to 4 substituents selected from the group consisting of aryl, $C_{3-8}$cycloalkyl, heteroaryl, heterocyclyl, $C_{1-6}$alkyl, $C_{1-6}$haloalkoxy, halo, $OR^{10}$, $SR^{10}$, $N(R^{10})_2$, $N(C_{1-6}$alkyl)$O(C_{1-6}$alkyl), $C_{1-6}$alkyl, $C(O)R^{10}$, $C_{1-6}$haloalkyl, $NO_2$, CN, $CF_3$, $SO_2(C_{1-6}$alkyl), $S(O)(C_{1-6}$alkyl), $NR^{10}SO_2R^6$, $SO_2N(R^6)_2$, $NHCOOR^6$, $NHCOR^6$, $NHCONHR^6$, $CO_2R^{10}$ and)$C(O)N(R^{10})_2$; wherein the 2 adjacent substituents of said $R^9$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;

or $R^8$ and $R^9$ are optionally taken together, with the nitrogen atom to which they are attached, to form a 4- to 8-membered monocyclic ring containing 0 to 2 additional heteroatoms selected from the group consisting of N, O and S;

each $R^{10}$ is independently selected from the group consisting of H and $C_{1-6}$alkyl;

Z is $C_{1-6}$alkylene, $C_{0-5}$alkylene-O—, $C_{0-5}$alkylene-$NR^{10}$—, $C_{2-6}$alkenylene, $C_{2-5}$alkenylene-O—, $C_{2-5}$alkenylene-$NR^{10}$—, $C_{2-6}$alkynylene, $C_{2-5}$alkynylene-O—, $C_{2-5}$alkynylene-$NR^{10}$—, $C_{0-3}$alkylene-C(O)O—, $C_{0-3}$alkylene-C(O)—$NR^{10}$—, $C_{0-3}$alkylene-O—C(O)—$NR^{10}$— and $C_{0-3}$alkylene-$NR^{10}$—C(O)O—, each substituted by 0 to 2 $C_{1-4}$alkyl;

ring B is selected from the group consisting of N-linked 4- to 9-membered heterocycles containing one N atom, containing 0 or 1 additional heteroatom selected from N, O and S, and substituted by 0 to 2 $R^{10}$;

each W is independently selected from the group consisting of halogen, $OR^{10}$, $C_{1-6}$alkyl, CN, $NO_2$, $CF_3$, $CO_2R^{10}$, $CON(R^{18})_2$, $COR^{10}$, $NR^5C(O)R^{10}$, aryl and heteroaryl;

M is selected from the group consisting of $C_{3-9}$alkylene, $C_{3-9}$alkenylene and $C_{3-9}$alkynylene, substituted by 0 to 3 substituents selected from the group consisting of $C_{1-6}$alkyl, $(CH_2)_{0-3}C_{3-8}$cycloalkyl and $(CH_2)_{0-3}$aryl, and containing 0 or 1 member selected from the group consisting of O, S and $NR^{10}$ group; and ring A is selected from the group consisting of 8- to 14-membered fused carbobi- and carbotricyclic ring systems, containing 0 to 4 heteroatoms selected from N, O and S.

DETAILED DESCRIPTION OF THE INVENTION

In one embodiment of the present invention, n is 0 or 1. Preferably, n is 0.

In another embodiment, $R^1$ is $CONR^{10}SO_2R^6$ or $CONR^{10}SO_2NR^8R^9$ where $R^6$, $R^8$, $R^9$ and $R^{10}$ are as hereinbefore defined. Preferably, $R^1$ is $CONR^{10}SO_2R^6$ where $R^6$ and $R^{10}$ are as hereinbefore defined. More preferably, $R^1$ is $CONHSO_2R^6$ where $R^6$ is as hereinbefore defined. Especially, $R^1$ is $CONHSO_2$—$C_{3-8}$cycloalkyl. More especially, $R^1$ is $CONHSO_2$—$C_{3-6}$cycloalkyl. Most especially, $R^1$ is $CONHSO_2$-cyclopropyl. Other substituents are as defined in the summary.

In another embodiment, $R^2$ is $C_{1-6}$alkyl or $C_{2-6}$alkenyl, optionally substituted with 1 to 3 fluoro or chloro. Preferably, $R^2$ is $C_{1-4}$alkyl or $C_{2-4}$alkenyl, optionally substituted with 1 to 3 fluoro. More preferably, $R^2$ is $C_{1-2}$alkyl or $C_{2-3}$alkenyl. Most preferably, $R^2$ is ethyl or ethenyl. Other substituents are as defined in the summary or as provided in the above embodiment.

In another embodiment, $R^3$ is $C_{1-6}$alkyl, $(CH_2)_{0-3}C_{3-8}$cycloalkyl, $(CH_2)_{0-3}$aryl or Het, optionally substituted by halo, $OR^{10}SR^{10}$, $N(R^{10})_2$, $C_{1-6}$alkyl, $NO_2$, CN, $CF_3$, $NR^{10}SO_2R^6$, $SO_2N(R^6)_2$, $NHC(O)OR^6$, $NHC(O)R^6$, $NHC(O)NHR^6$, $CO_2R^{16}$, $C(O)R^{10}$ and $C(O)N(R^{10})_2$, where $R^6$ and $R^{10}$ are as hereinbefore defined. Preferably, $R^3$ is $C_{1-6}$alkyl or $(CH_2)_{0-3}C_{3-8}$cycloalkyl, optionally substituted by halo, $OR^{10}$ or $C_{1-6}$alkyl, where $R^{10}$ is as hereinbefore defined. More preferably, $R^3$ is $C_{1-6}$alkyl or $(CH_2)_{0-3}C_{3-8}$cycloalkyl. Most preferably, $R^3$ is $C_{1-4}$alkyl or $C_{3-6}$cycloalkyl. Especially, $R^3$ is $C_{3-4}$alkyl or $C_{5-6}$cycloalkyl. More especially, $R^3$ is tent-butyl, cyclopentyl or cyclohexyl. Other substituents are as defined in the summary or as provided in the above embodiments.

In another embodiment, each W is independently halo, $OR^{10}$, $C_{1-5}$alkyl, CN, $NO_2$, $CF_3$, $CO_2R^{10}$ or $CON(R^{10})_2$, where $R^{ID}$ is as hereinbefore defined. Preferably, each W is independently halo, $OC_{1-6}$alkyl, $C_{1-6}$alkyl, CN, $NO_2$ or $CF_3$. More preferably, each W is independently $OC_{1-4}$alkyl or $C_{1-4}$alkyl. Most preferably, W is $OC_{1-2}$alkyl or $C_{1-2}$alkyl. Especially, W is methoxy or methyl. Other substituents are as defined in the summary or as provided in the above embodiments.

In another embodiment, Z is $C_{0-5}$alkylene-O—, $C_{0-5}$alkylene-$NR^{10}$—, $C_{2-5}$alkenylene-O—, $C_{2-5}$alkenylene-$NR^{10}$—, $C_{2-5}$alkynylene-O—, $C_{2-5}$alkynylene-$NR^{10}$— or $C_{0-3}$alkylene-C(O)—O—, optionally substituted by $C_{1-4}$alkyl, where $R^{10}$ is as hereinbefore defined. Preferably, Z is $C_{0-5}$alkylene-O—, $C_{0-5}$alkylene-$NR^{10}$—, $C_{2-5}$alkenylene-O—, $C_{2-5}$alkenylene-$NR^{10}$— or $C_{0-3}$alkylene-C(O)—O—, where $R^{10}$ is as hereinbefore defined. More preferably, Z is $C_{0-5}$alkylene-O—, $C_{2-5}$alkenylene-O— or $C_{0-2}$alkylene-C(O)—O—. Most preferably, Z is $CO_{0-3}$alkylene-O—, $C_{2-3}$alkenylene-O— or $C_{0-2}$alkylene-C(O)—O—. Especially, Z is $C_{0-3}$alkylene-O— or $C_{0-1}$alkylene-C(O)—O—. More especially, Z is —CH$_2$—O—, O or C(O)O. Most especially, Z is O or C(O)O. Other substituents are as defined in the summary or as provided in the above embodiments.

In one embodiment, ring B is a N-linked 4- to 8-membered heterocycle containing one N atom, optionally containing one further heteroatom selected from N or O, and optionally substituted by $R^{10}$, where $R^{10}$ is as hereinbefore defined. Preferably, ring B is a N-linked 4- to 7-membered heterocycle containing one N atom, optionally containing one further N atom, and optionally substituted by $C_{1-6}$alkyl. More preferably, ring B is a N-linked 4- to 6-membered heterocycle. Examples of suitable B groups are:

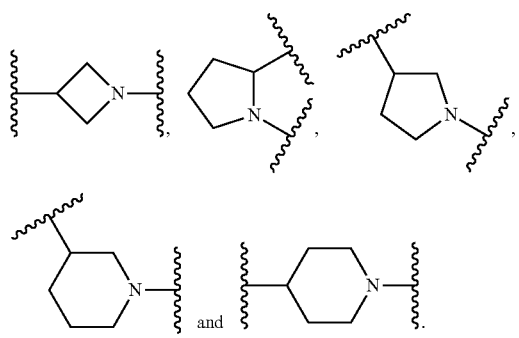

Other substituents are as defined in the summary or as provided in the above embodiments.

In one embodiment, M is $C_{3-8}$alkylene, $C_{3-8}$alkenylene or $C_{3-8}$alkynylene, optionally substituted by $C_{1-6}$alkyl, and optionally containing one O atom or one $NR^{10}$ group, where $R^{10}$ is as hereinbefore defined. Preferably, M is $C_{3-7}$alkylene or $C_{3-7}$alkenylene, optionally substituted by $C_{1-4}$alkyl, and optionally containing one O atom. More preferably, M is $C_{3-6}$alkylene or $C_{3-6}$alkenylene, optionally substituted by $C_{1-2}$alkyl, and optionally containing one O atom. Most preferably, M is $C_{3-5}$alkylene or $C_{3-5}$alkenylene, optionally containing one O atom. Examples of suitable M groups are: butylene,

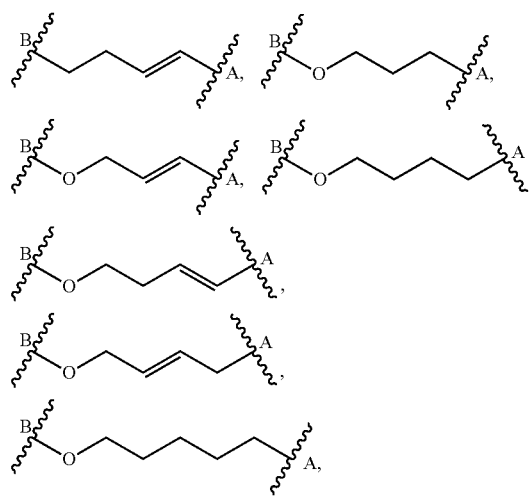

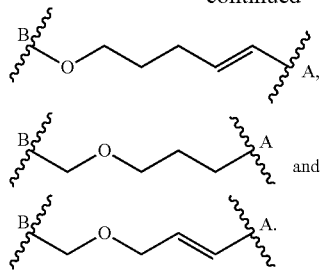

Other substituents are as defined in the summary or as provided in the above embodiments.

In another embodiment, ring A is a 8- to 14-membered fused carbobi- or carbotricyclic ring system, containing 0 to 3 heteroatoms selected from N and O, and optionally substituted by $R^4$, where $R^4$ is as hereinbefore defined. Preferably, ring A is a 8- to 14-membered fused carbobi- or carbotricyclic ring system, containing 0 or 2 N atoms, and optionally substituted by $R^4$, where $R^4$ is as hereinbefore defined. Examples of suitable A groups, optionally substituted by $R^4$ are:

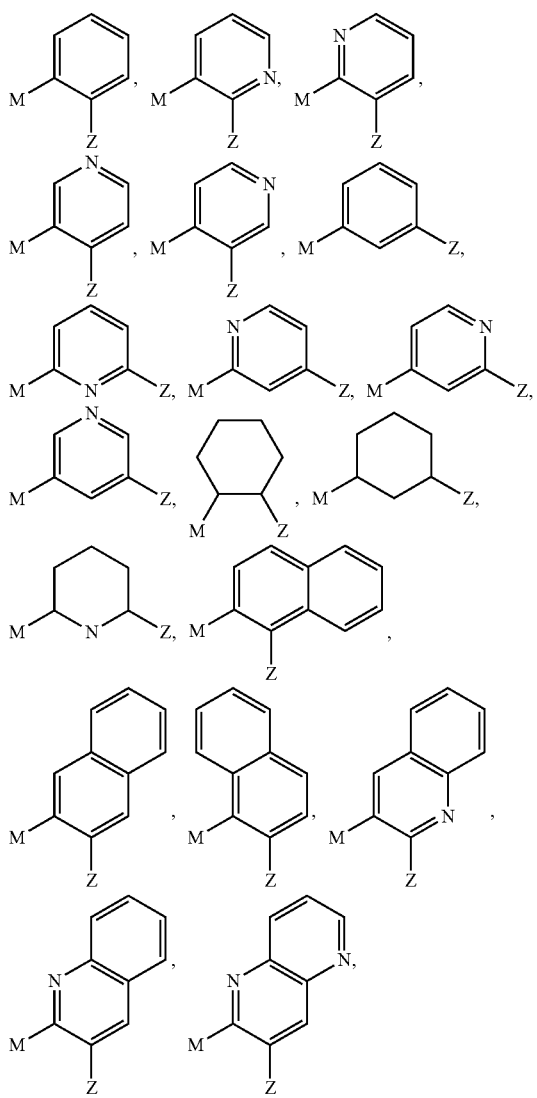

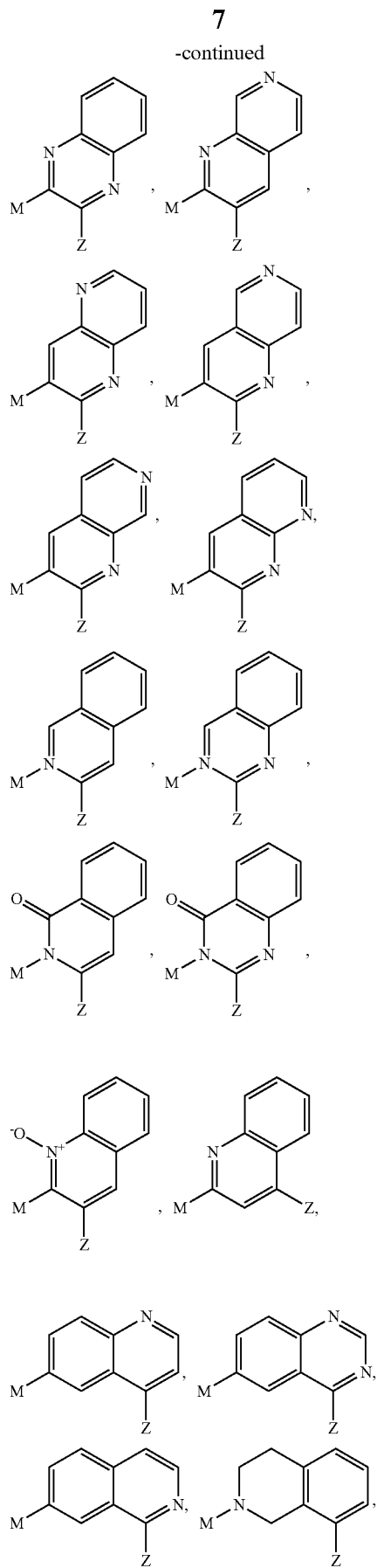
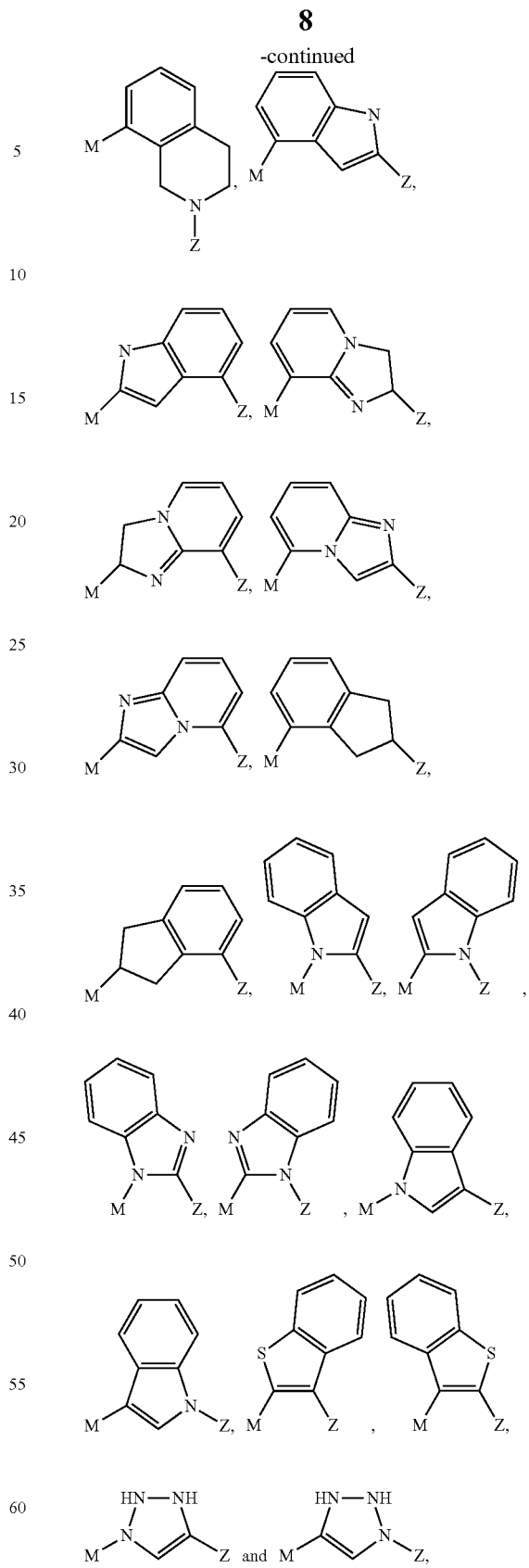
which may be substituted as indicated above. Other substituents are as defined in the summary or as provided in the above embodiments.

In another embodiment of the present invention, the compound of formula (I) is a compound of formula (Ia):

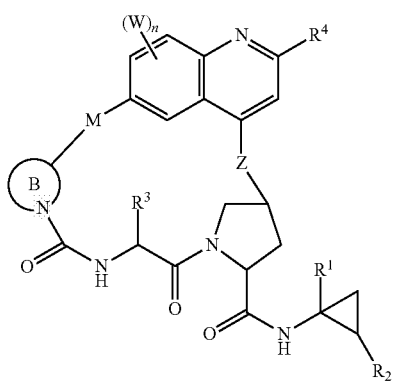

(Ia)

or a pharmaceutically acceptable salt thereof, wherein $R^1$, $R^2$, $R^3$, $R^4$, W, n, Z, M and ring B are as defined in relation to formula (I) or the above embodiments.

In another embodiment of the present invention, there is provided the compound of formula (I) is a compound of formula (Iaa):

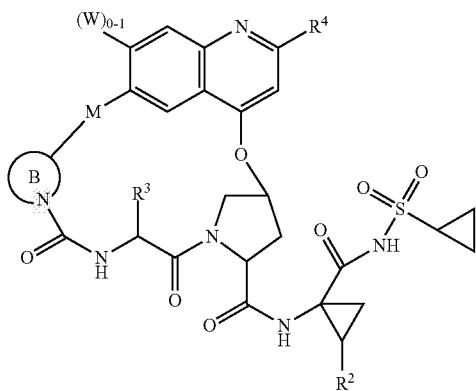

(Iaa)

or a pharmaceutically acceptable salt thereof, wherein $R^2$, $R^3$, $R^4$, W, M and ring B are as defined in relation to formula (I) or the above embodiments.

In another embodiment of the present invention, there is provided the compound of formula (I) is a compound of formula (Ib):

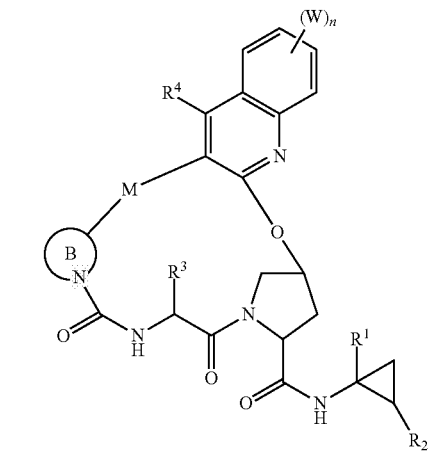

(Ib)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Iba):

(Iba)

or a pharmaceutically acceptable salt thereof, wherein $R^2$, $R^3$, W, M and ring B are as defined in relation to formula (I) or the above embodiments.

In another embodiment of the present invention, there is provided the compound of formula (I) is a compound of formula (Ic):

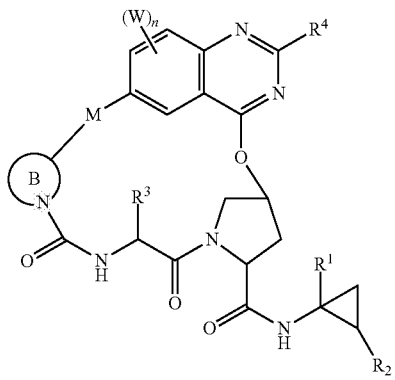

(Ic)

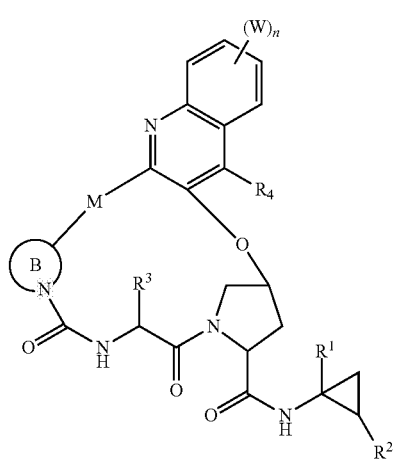

(Id)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Ica):

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Ida):

(Ica)

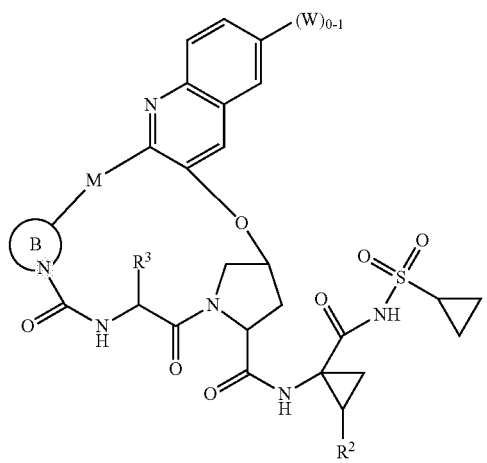

(Ida)

or a pharmaceutically acceptable salt thereof, wherein $R^2$, $R^3$, $R^4$, M and ring B are as defined in relation to formula (I) or the above embodiments.

In another embodiment of the present invention, there is provided the compound of formula (I) is a compound of formula (Id):

or a pharmaceutically acceptable salt thereof, wherein $R^2$, $R^3$, W, M and ring B are as defined in relation to formula (I) or the above embodiments.

In another embodiment of the present invention, there is provided the compound of formula (I) is a compound of formula (Ie):

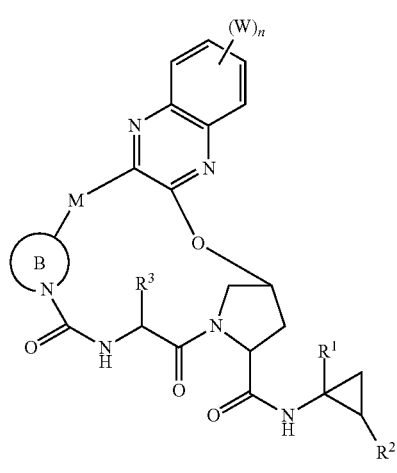

(Ie)

or a pharmaceutically acceptable salt thereof, wherein $R^1$, $R^2$, $R^3$, W, n, M and ring B are as defined in relation to formula (I) or the above embodiments.

In another embodiment of the present invention, there is provided the compound of formula (I) is a compound of formula (Iea):

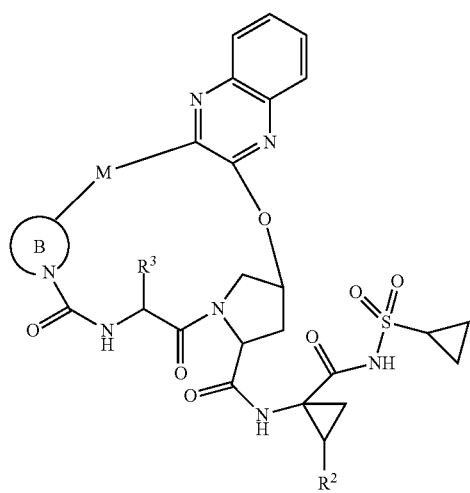

(Iea)

or a pharmaceutically acceptable salt thereof, wherein $R^2$, $R^3$, M and ring B are as defined in relation to formula (I) or the above embodiments.

In another embodiment of the present invention, there is provided the compound of formula (I) is a compound of formula (If):

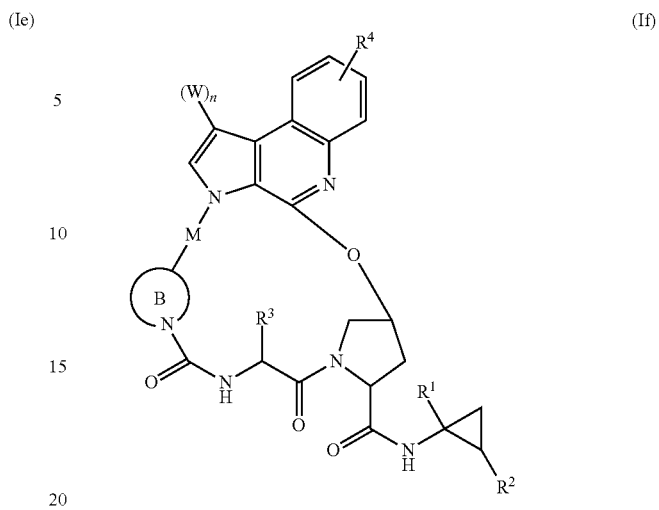

(If)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Ifa):

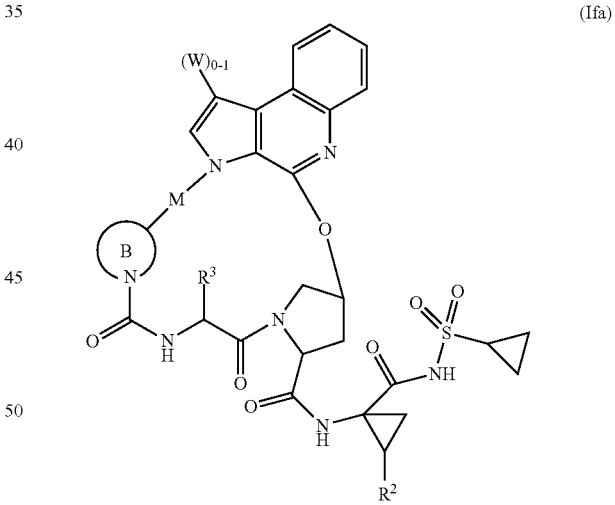

(Ifa)

or a pharmaceutically acceptable salt thereof, wherein $R^2$, $R^3$, W, M and ring B are as defined in relation to formula (I) or the above embodiments.

In another embodiment of the present invention, there is provided the compound of formula (I) is a compound of formula (Ig):

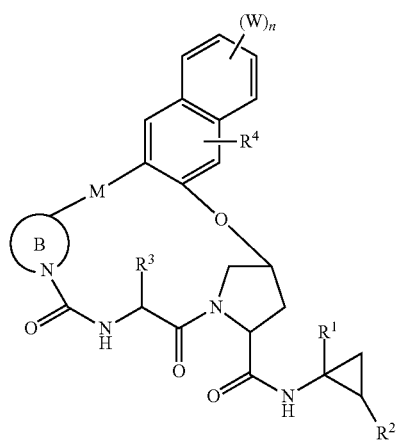

(Ig)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Iga):

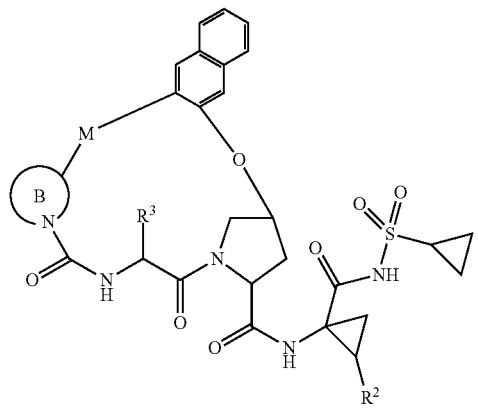

(Iga)

or a pharmaceutically acceptable salt thereof, wherein $R^2$, $R^3$, M and ring B are as defined in relation to formula (I) or the above embodiments.

In another embodiment of the present invention, there is provided the compound of formula (I) is a compound of formula (Ih):

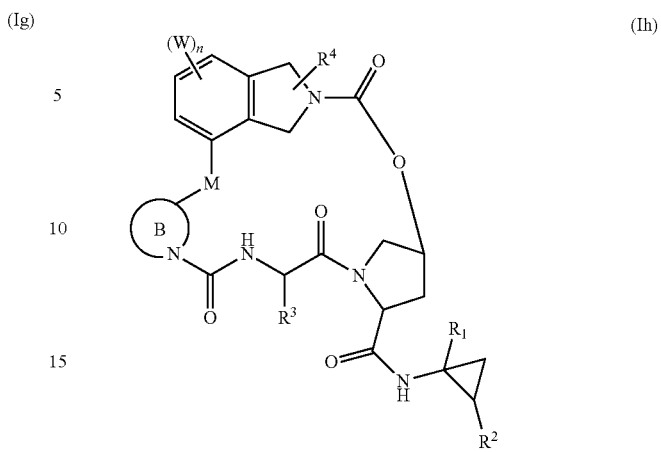

(Ih)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Iha):

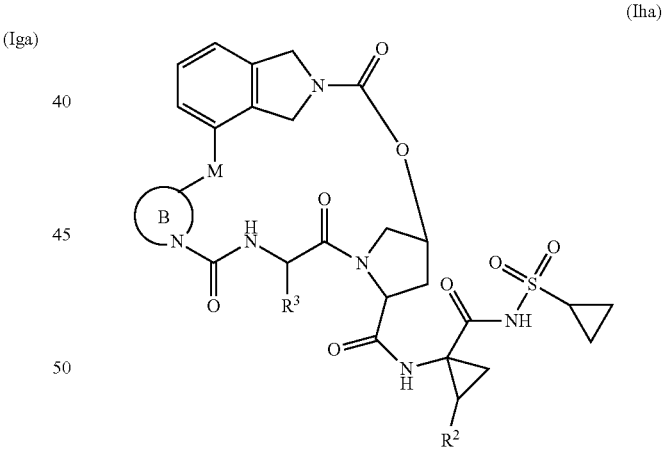

(Iha)

or a pharmaceutically acceptable salt thereof, wherein $R^2$, $R^3$, M and ring B are as defined in relation to formula (I) or the above embodiments.

In another embodiment of the present invention, there is provided the compound of formula (I) is a compound of formula (II):

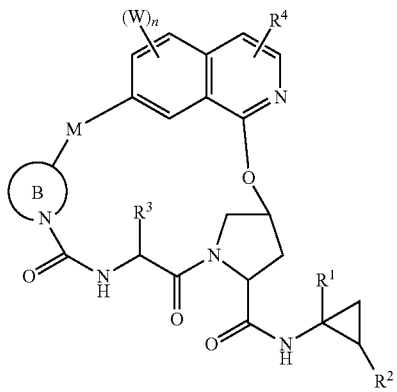

(Ii)

or a pharmaceutically acceptable salt thereof, wherein $R^1$, $R^2$, $R^3$, $R^4$, W, n, M and ring B are as defined in relation to formula (I) or the above embodiments.

In another embodiment of the present invention, there is provided the compound of formula (I) is a compound of formula (Iia):

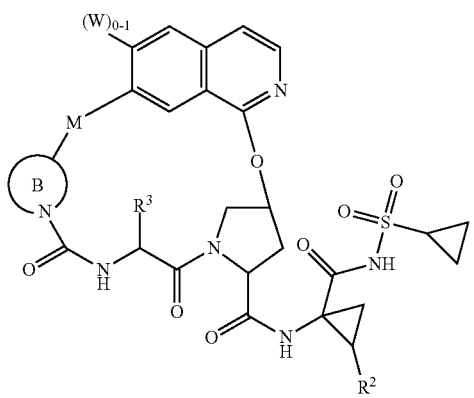

(Iia)

or a pharmaceutically acceptable salt thereof, wherein $R^2$, $R^3$, W, M and ring B are as defined in relation to formula (I) or the above embodiments.

In another embodiment of the present invention, there is provided the compound of formula (I) is a compound of formula (Ij):

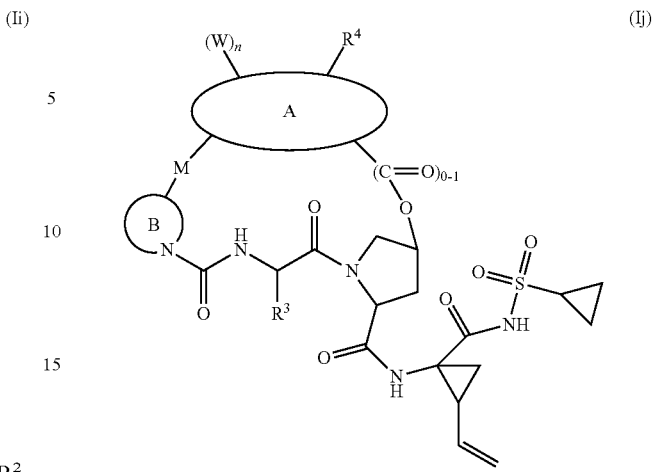

(Ij)

or a pharmaceutically acceptable salt thereof, wherein $R^3$, $R^4$, W, n, M and ring B are as defined in relation to formula (I) or the above embodiments.

When any variable occurs more than one time in formula (I) or in any substituent, its definition on each occurrence is independent of its definition at every other occurrence.

In another embodiment of the invention, the compound of the invention is selected from the exemplary species depicted in Examples 1 through 45 shown below.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination which is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS3 protease, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof which comprises administering to the subject an effective amount of a compound of formula (I).

(g) A method of treating HCV infection and/or reducing the likelihood or severity of symptoms of HCV infection in a subject in need thereof which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" as a group or part of a group refers to any linear or branched chain alkyl group having a number of carbon atoms in the specified range. Thus, for example, "$C_{1-6}$alkyl" refers to all of the hexyl alkyl and pentyl alkyl isomers as well as n-, iso-, sec- and tert-butyl, n- and iso-propyl, ethyl and methyl. As another example, "$C_{1-4}$alkyl" refers to n-, iso-, sec- and tert-butyl, n- and iso-propyl, ethyl and methyl.

The term "alkoxy" represents any linear or branched chain alkyl group having a number of carbon atoms in the specified range and attached through an oxygen bridge. Examples of suitable alkoxy groups include methoxy, ethoxy, n-propoxy, iso-propoxy, n-butoxy, sec-butoxy, iso-butoxy and tert-butoxy.

The term "alkenyl" as a group or part of a group refers to any linear or branched chain alkyl group containing at least one double bond, which may occur at any point along the chain, and having a number of carbon atoms in the specified range. E- and Z-forms are both included, where applicable. Examples of suitable alkenyl groups include vinyl, allyl, butenyl and pentenyl.

The term "alkynyl" as a group or part of a group refers to any linear or branched chain alkyl group containing at least one triple bond, which may occur at any point along the chain, and having a number of carbon atoms in the specified range. Examples of suitable alkynyl groups include ethynyl, propynyl, butynyl and pentynyl.

The term "cycloalkyl" refers to any cyclic alkyl ring having a number of carbon atoms in the specified range. Examples of suitable cycloalkyl groups include cyclopropyl, cyclobutyl, cyclopentyl and cyclohexyl.

The terms "alkylene", "alkenylene" and alkynylene" as a group or part of a group refer to the groups "alkyl", "alkenyl" and "alkynyl" respectively, when they are divalent, i.e. attached at two atoms.

The term "halogen" or "halo" means fluorine, chlorine, bromine and iodine (alternatively referred to as fluoro, chloro, bromo and iodo, respectively).

The term "aryl" as a group or part of a group means phenyl or naphthyl. The term "heteroaryl" as a group or part of a group means a 5- or 6-membered aromatic ring having 1, 2 or 3 heteroatoms selected from N, O and S, attached through a ring carbon or nitrogen. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl and tetrazolyl.

The term "heterocyclyl" as a group or part of a group means a 5- to 7-membered saturated or unsaturated non-aromatic ring having 1, 2, 3 or 4 heteroatoms selected from N, O and S, attached through a ring carbon or nitrogen.

Unless expressly stated to the contrary, all ranges cited herein are inclusive. For example, a heteroaryl ring described as containing from "1 to 3 heteroatoms" means the ring can contain 1, 2, or 3 heteroatoms.

Where a compound or group is described as "optionally substituted," the compound or group may be unsubstituted or one or more substituents may be present. Furthermore, optional substituents may be attached to the compounds or groups which they substitute in a variety of ways, either directly or through a connecting group such as amine, amide, ester, ether, thioether, sulfonamide, sulfamide, sulfoxide, urea, thiourea and urethane. As appropriate, an optional substituent may itself be substituted by another substituent, either directly to the former or through a connecting group such as those exemplified above.

Specific compounds within the scope of this invention include those named in the Examples and Tables hereinbelow and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, para-toluenesulfonic acid (p-toluenesulfonic acid), maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs* (H. Bundgaard ed., Elsevier 1985).

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

As used herein, the term "prodrug" is intended to encompass an inactive drug form or compound that is converted into an active drug form or compound by the action of enzymes, chemicals or metabolic processes in the body of an individual to whom it is administered.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

The present invention includes within its scope solvates of the compounds of formula (I) and salts thereof, for example, hydrates; reference to "compounds" includes complexes such as hydrates.

The present invention also includes within its scope any enantiomers, diastereomers, geometric isomers and tautomers of the compounds of formula (I). It is to be understood that all such isomers and mixtures thereof are encompassed within the scope of the invention.

Some preferred compounds of the present invention will have the stereochemistry as shown in formula (Ik):

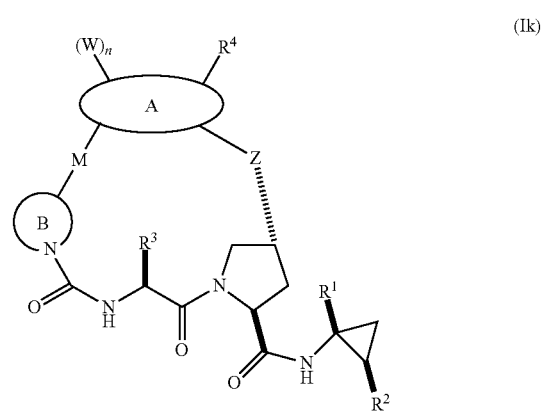

The present invention further provides a compound of formula (I) or a pharmaceutically acceptable salt thereof for use in therapy.

The present invention also provides a compound of formula (I) or a pharmaceutically acceptable salt thereof for use in the treatment or prevention of infection by hepatitis C virus in a human or animal.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon In a further aspect, the invention provides a method of inhibiting hepatitis C virus protease and/or of treating, preventing or reducing the likelihood or severity of an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof.

For the purpose of inhibiting HCV N3 protease and treating HCV infection and/or reducing the likelihood or severity of symptoms of HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in WO 01/60379. In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). Thus, inhibition of IMPDH represents another useful target for the discovery of inhibitors of HCV replication. Therefore, the compounds of the present invention may also be administered in combination with an inhibitor of IMPDH, such as VX-497, disclosed in WO 97/41211 and WO 01/00622; another IMPDH inhibitor, such as that disclosed in WO 00/25780; or mycophenolate mofetil. See A. C. Allison and E. M. Eugui, 44 (Suppl.) *Agents Action* 165 (1993).

For the treatment of HCV infection, the compounds of the present invention may also be administered in combination with the antiviral agent amantadine (1-aminoadamantane).

For a comprehensive description of this agent, see J. Kirschbaum, 12 *Anal. Profiles Drug Subs.* 1-36 (1983).

The compounds of the present invention may also be combined for the treatment of HCV infection with antiviral 2'-C-branched ribonucleosides disclosed in R. E. Harry-O'Kuru et al., 62 *J. Org. Chem.* 1754-59 (1997); M. S. Wolfe et al., 36 *Tet. Lett.* 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-(3-D-ribofitranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in International Patent Application Publications WO 02/51425, assigned to Mitsubishi Pharma Corp.; WO 01/79246, WO 02/32920, WO 02/48165 and WO2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007 and US 2004/0063658; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. No. 6,777,392 and U.S. Patent Application Publication US 2004/0067901; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

The compounds of the present invention may also be combined for the treatment of HCV infection with non-nucleoside inhibitors of HCV polymerase such as those disclosed in WO 01/77091; WO 01/47883; WO 02/04425; WO 02/06246; WO 03/062211; WO 2004/087714; WO 2004/110442; WO 2005/034941; WO 2005/023819; WO 2006/029912; WO 2006/008556; WO 2006/027628; GB 2430621; WO2006/046030; WO2006/046039; WO 2006/119975; WO 2007/028789; WO 2007/029029; WO 2007/054741; WO 02/20497; WO 2005/016927 (in particular JTK003); WO 2005/080399; WO 2006/020082; and WO 2004/041201.

The present invention also provides a process for the preparation of compounds of formula (I).

According to a general process (a), compounds of formula (I) may be prepared by the coupling of the ester of formula (II) with the amine of formula (III):

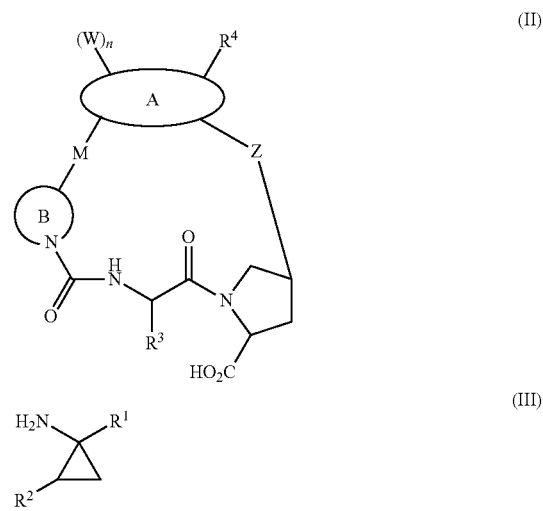

where $R^1$, $R^2$, $R^3$, $R^4$, M, W, n, Z, ring A and ring B are as defined in relation to formula (I). The reaction is conveniently carried out in the presence of a coupling reagent, such as TBTU or HATU, and a base, such as diisopropylethylamine or triethylamine, in a solvent. Suitable solvents include DMF and dichloromethane.

The compound of formula (II) where M has 4 or more carbon atoms in the tether and one or more double bonds may be prepared by the internal ring closure of the diene of formula (IV):

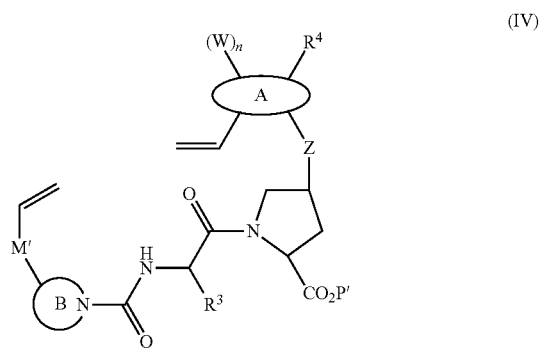

where $R^3$, $R^4$, W, n, Z, ring A and ring B are as defined in relation to formula (I), $P^1$ is a suitable protecting group, such as $C_{1-6}$alkyl, particularly methyl, and M' is a suitable precursor to group M. The reaction is conveniently carried out in the presence of a metathesis catalyst, such as Zhan catalyst (dichloro(5-chloro-2-isopropoxybenzylidene)(1,3-dimethylimidazolidin-2-ylidene)ruthenium), preferably at raised temperature, in a suitable solvent such as 1,2-dichloroethane. The resultant ring double bond may be hydrogenated to give a further compound of formula (II). The hydrogenation is preferably carried out in the presence of a suitable catalyst, such as palladium on carbon, in a suitable solvent, such as methanol/ethyl acetate mixture Compounds of formulae (II), (III) and (IV) may be prepared by conventional methodology well known to one of ordinary skill in the art using, for instance, procedures described in the accompanying Schemes and Examples, or by alternative procedures that will be readily apparent.

Further details of suitable procedures will be found in the accompanying Schemes and Examples. For instance compounds of formula (I) can be converted into other compounds of formula (I) using synthetic methodology well known in the art.

Thus, for instance, the compound of formula (I) where M is unsaturated may be converted into the compound of formula (I) where M is saturated by hydrogenation, preferably in the presence of a suitable catalyst, such as palladium on carbon, in a suitable solvent, such as methanol/ethyl acetate mixture.

The compounds of the present invention may be synthesized as outlined in the following general schemes below.

During any of the described synthetic sequences, it may be necessary and/or desirable to protect sensitive or reactive groups on any of the molecules concerned. This may be achieved by means of conventional protecting groups such as those described in *Protective Groups in Organic Chemistry* (J. F. W. McOmie ed., Plenum Press 1973); and T. W. Greene & P. G. M. Wuts, *Protective Groups in Organic Synthesis* (John Wiley & Sons, 3$^{rd}$ ed. 1999). The protecting groups may be removed at a convenient subsequent stage using methods known from the art.

The compounds of the present inventions are useful in the inhibition of HCV protease (e.g., HCV NS3 protease) and the treatment prevention or reduction of the likelihood or severity of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention are commercial products to be sold for these purposes.

The HCV NS3 protease inhibitory activity of the present compounds may be tested using assays known in the art. One such assay is HCV NS3 protease time-resolved fluorescence (TRF) assay described as follows:

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% TRITON X-100, 10 mM DTT, and 0.1% PEG 8000. The NS3 protease was pre-incubated with various concentrations of inhibitors for 10-30 minutes. The peptide substrate for the assay is Ac—C (Eu)-DDMEE-Abu-[COO]-XSAK(QSY7)-NH$_2$ (SEQ ID NO. 1) g65, where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a VICTOR V2 or FUSION fluorimeter (Perkin Elmer Life and Analytical Sciences) with excitation at 340 nm and emission at 615 nm with 50-400 µs is delay. Testing concentrations of different enzyme forms was selected with a signal to background ratio of 10-30. The inhibition constants were derived using a four-parameter fit.

Another suitable assay is the cellular Replicon or rheplisa assay described as follows:

Cell-Based HCV Replication Assay

Cell clones that stably maintain subgenomic HCV replicon were obtained by transfecting Huh-7 cells with an RNA replicon identical to I$_{377}$neo/NS3-3'/wt described by V. Lohmann et al., 285 SCIENCE 110 (Jul. 2, 1999) (EMBL-GENBANK No. AJ242652), followed by selection with neomycin sulfate (G418). Viral replication was monitored by measuring the expression of the NS3 protein by an ELISA assay performed directly on cells grown in 96-well microtiter plates (Cell-ELISA) using the anti-NS3 monoclonal antibody 10E5/24 (as described in International Patent Application Publication WO 02/59321). Cells were seeded into 96 well plates at a density of $10^4$ cells per well in a final volume of 0.1 ml of DMEM/ 10% FCS. Two hours after plating, 50 µl of DMEM/10% FCS containing a 3× concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS+0.1% TRITON X-100+0.02% SDS (PBSTS) and then incubated o/n at 4° C. with the 10E5/ 24 mab diluted in Milk/PBSTS. After washing 5 times with PBSTS, the cells were incubated for 3 hours at room temperature with Fe-specific anti-mouse IgG conjugated to alkaline phosphatase (Sigma), diluted in Milk/PBSTS. After washing again as above, the reaction was developed with p-nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 (IC$_{50}$) was calculated by fitting the data to the Hill equation, $$\text{Fraction inhibition} = 1-(A_i-b)/(A_0-b) = [I]^n/([I]^n + IC_{50})$$

where:
- Ai=absorbance value of HBI10 cells supplemented with the indicated inhibitor concentration.
- A$_0$=absorbance value of HBI10 cells incubated without inhibitor.
- b=absorbance value of Huh-7 cells plated at the same density in the same microtiter plates and incubated without inhibitor.
- n=Hill coefficient.

The tested compounds of the present invention were active in the cell based HCV replication assay with activities <50 µM, and especially <5 µM.

Other examples of such assays are described in e.g., International Patent Application Publication WO 2005/046712. Compounds useful as HCV NS3 protease inhibitors would have a Ki less than 50 µM, more preferably less than 10 µM, most preferably less than 1 µM, especially less than 100 nM, and more especially less than 50 nM.

The following examples serve to illustrate the invention and its practice.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in Hertz (Hz); number of protons. Mass spectral (MS) data were obtained on a PERKIN ELMER API 100, or WATERS MICROMASS ZQ, operating in negative (ES) or positive (ES+) ionization mode and results are reported as the ratio of mass over charge (m/z). Preparative scale HPLC separations were carried out on a WATERS MICROMASS System incorporating a 2525 pump module, a MICROMASS ZMD detector and a 2767 collection module, under FRACTION LINX software or on a SHIMADZU preparative system.

LIST OF ABBREVIATIONS

| | |
|---|---|
| AcOH | Acetic acid |
| BOP | Benzotriazole-1-yl-oxy-tris-(dimethylamino)-phosphonium hexafluorophosphate |
| Brosyl chloride | 4-Bromobenzenesulfonyl chloride |
| BuLi | Butyl lithium |
| $CDCl_3$ | Deuterio-trichloromethane |
| $CH_3CN$ | Acetonitrile |
| mCPBA | m-Chloroperbenzoic acid |
| $Cs_2CO_3$ | Cesium carbonate |
| DABCO | 1,4-Diazabicyclo[2.2.2]octane |
| DBU | 1,8-Diazabicyclo[5.4.0]undec-7-ene |
| DCC | Dicyclohexylcarbodiimide |
| DCE | 1,2-Dichloroethane |
| DCM | Dichloromethane |
| DEAD | Diethyl azodicarboxylate |
| DIEA | Diethylamine |
| DIPEA | Diisoproylethylamine |
| DMAP | 4-Dimethylaminopyridine |
| DMF | Dimethylformamide |
| DMSO | Dimethyl sSulfoxide |
| DPPF (also dppf) | 1,1'-bis(Diphenylphosphino)ferrocene |
| EDC | N-(3-Dimethylaminopropyl)-N'-ethylcarbodiimide hydrochloride |
| $Et_2O$ | Diethyl ether |
| EtOAc | Ethyl acetate |
| EtOH | Ethanol |
| h | hour(s) |
| HATU | O-(7-Azabenzotriazol-1-yl)-N,N,N',N'-tetramethyluronium hexafluorophosphate |
| HBr | Hydrobromic acid |
| HCl | Hydrochloric acid |
| $H_2O_2$ | Hydrogen peroxide |
| HOAc | Acetic acid |
| HOAt | 1-Hydroxy-7-azabenzotriazole |
| $KHSO_4$ | Potassium bisulfate |
| LiOH | Lithium hydroxide |
| MeCN | Acetonitrile |
| MeOH | Methanol |
| $MgSO_4$ | Magnesium sulfate |
| min | minute(s) |
| MTBE | Methyl tert-butyl ether |
| $Na_2SO_4$ | Sodium sulfate |
| $Na_2SO_3$ | Sodium sulfite |
| $NaHCO_3$ | Sodium bicarbonate |
| NaOH | Sodium hydroxide |
| $NH_4Cl$ | Ammonium chloride |
| $NH_4OH$ | Ammonium hydroxide |
| Nle | Norleucine |
| NMP | N-Methyl pyrrolidinone |
| Pd/C | Palladium on carbon |
| $PdCl_2(dppf)$-$CH_2Cl_2$ adduct | 1,1'-bis(diphenylphosphino)ferrocene-palladium(II)dichloride dichloromethane complex |
| PE | Petroleum ether |
| PhMe | Toluene |
| $P_2O_5$ | Phosphorus pentoxide ($P_4O_{10}$) |
| $POBr_3$ | Phosphoryl tribromide |
| $PPh_3$ | Triphenylphosphine |
| RT | Room temperature |
| Ru/C | Ruthenium on carbon |
| TBAF | Tetrabutylammonium fluoride |
| TBTU | O-Benzotriazol-1-yl-N,N,N',N'-tetramethyluronium tetrafluoroborate |
| TEA | Triethylamine |
| THF | Tetrahydrofuran |

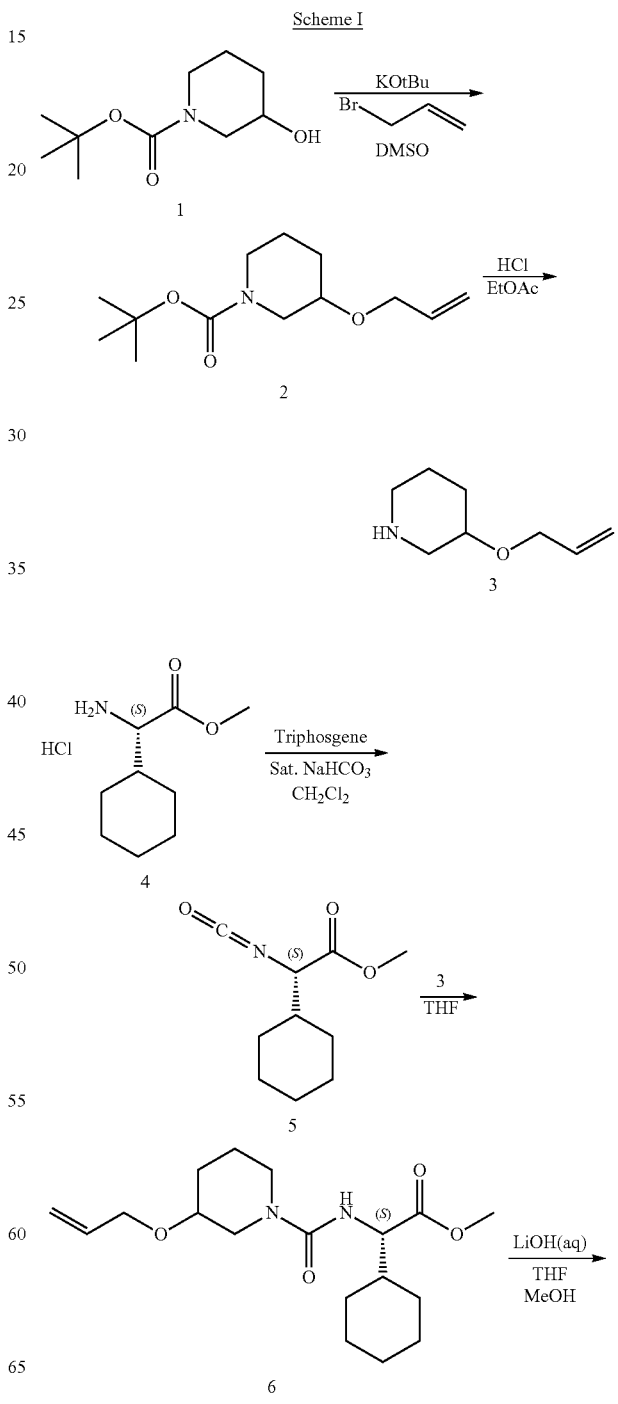

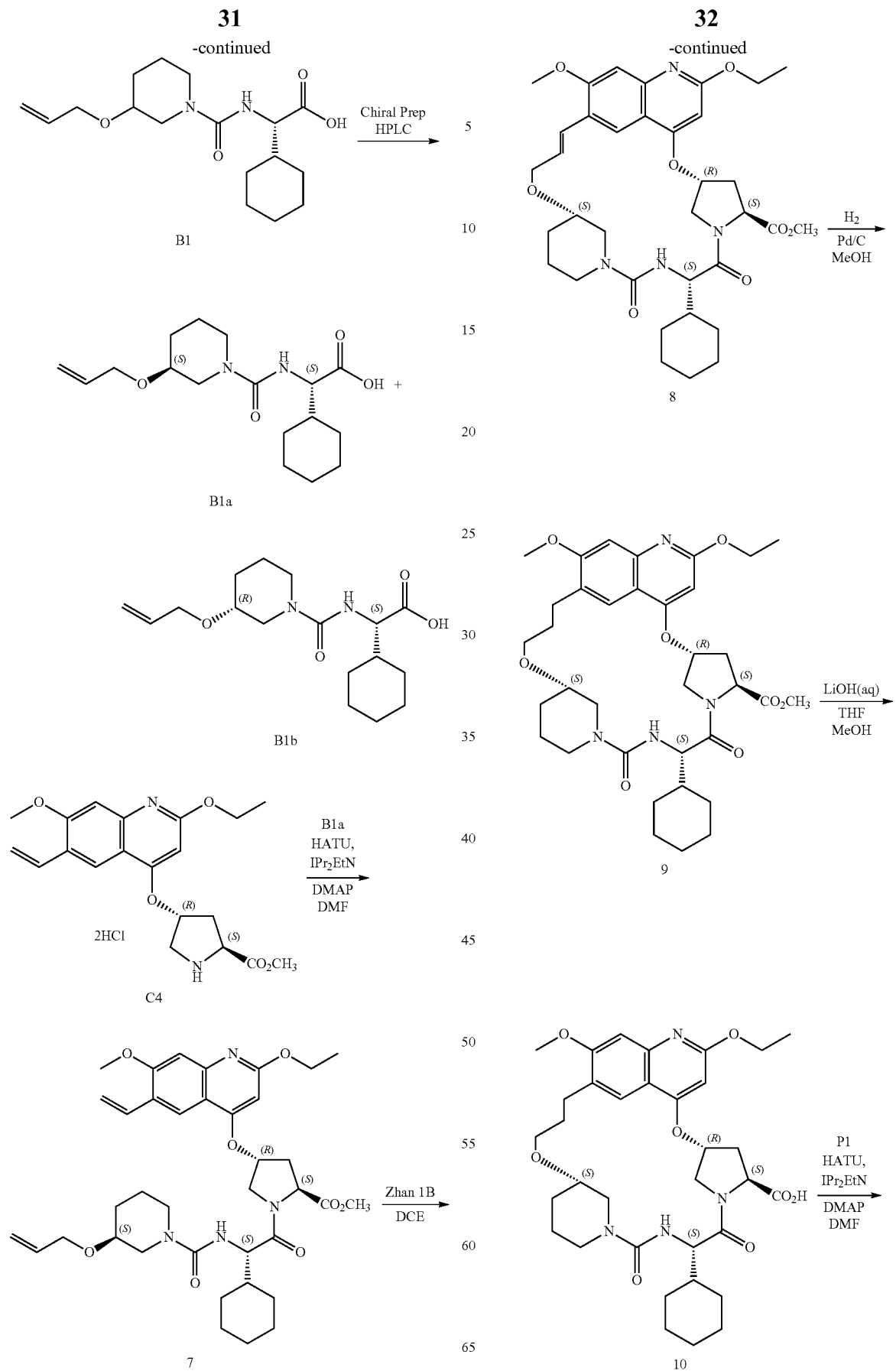

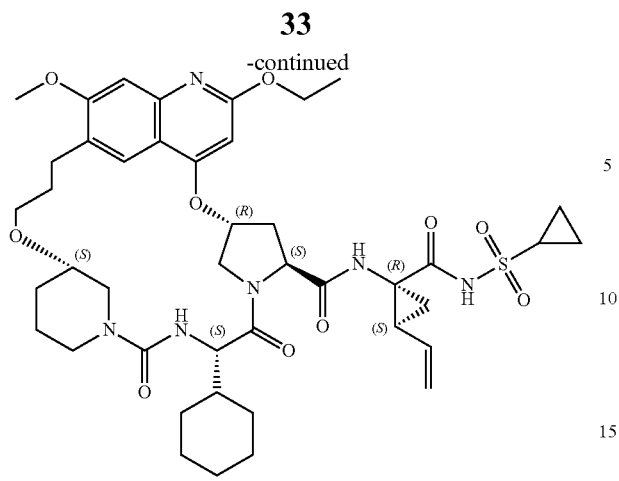
EXAMPLE 1
Scheme 2
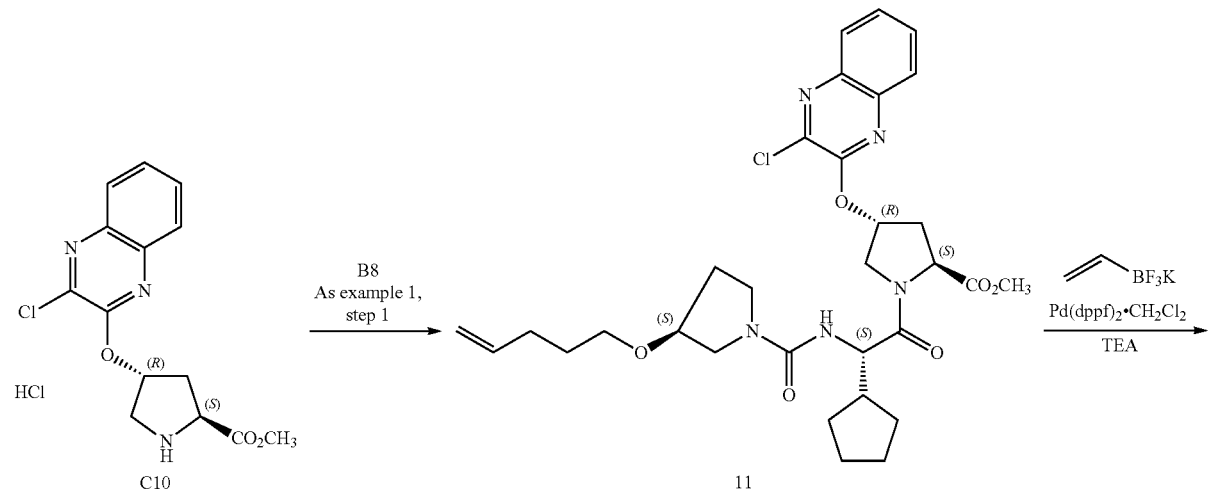
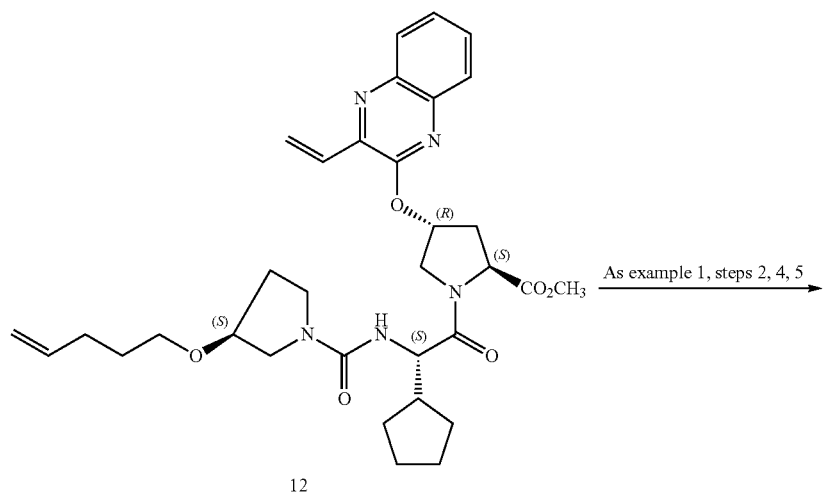

-continued

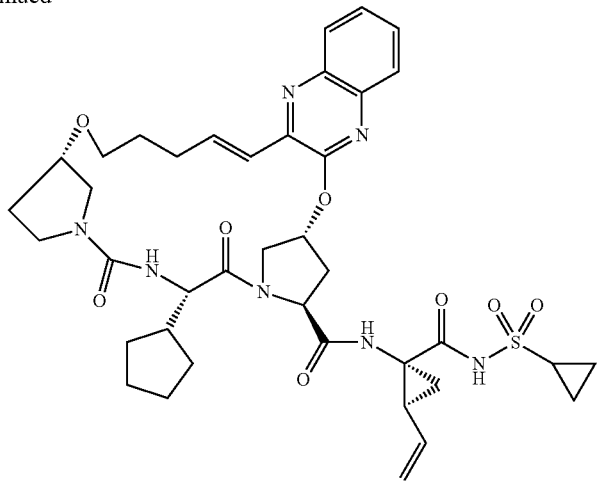

EXAMPLE 2

SYNTHESIS OF INTERMEDIATES

Synthesis of Intermediates A

| Intermediate # | Structure | Name | Literature Reference |
|---|---|---|---|
| A1 | 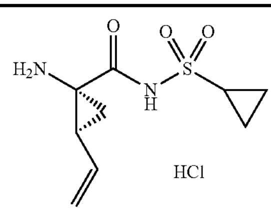 | (1R,2S)-1-Amino-N-(cyclopropylsulfonyl)-2-vinylcyclopropanecarboxamide hydrochloride | U.S. Pat. No. 6,995,174 |
| A2 | 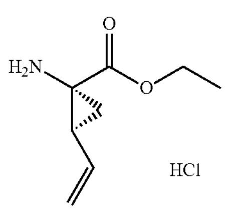 | Ethyl (1R,2S)-1-amino-2-vinylcyclopropanecarboxylate hydrochloride | U.S. Pat. No. 6,323,180 |

Intermediate A3: (1R,2R)-1-Amino-N-(cyclopropyl-sulfonyl)-2-ethylcyclopropanecarboxamide hydrochloride

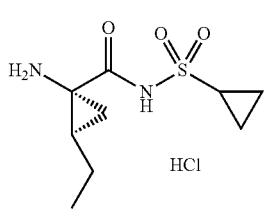

Step 1: tert-Butyl((1R,2R)-1-{[(cyclopropylsulfonyl)amino]carbonyl}-2-ethylcyclopropyl)carbamate

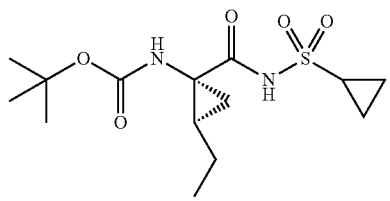 [SMILES: CC[C@@H]1C[C@]1(NC(=O)OC(C)(C)C)C(=O)NS(=O)(=O)C1CC1]

A hydrogenation vessel was charged with a MeOH (1000 mL) slurry of tert-butyl((1R,2S)-1-{[(cyclopropylsulfonyl)amino]carbonyl}-2-vinylcyclopropyl)carbamate (164 g, 0.50 mol) (U.S. Pat. No. 6,995,174) and 5% Ru/C (dry, 7.5 wt %, 12.4 g) and set stirring. The vessel was placed under nitrogen (20 psig) and vented to atmospheric pressure three times to remove residual oxygen. The vessel was then placed under hydrogen (50 psig). After 20 h, the vessel was vented to atmospheric pressure. The reaction slurry was then transferred out of the reaction and filtered through SOLKA FLOK (34 grams, wetted with 100 mL MeOH) to yield a clear, light brown solution. The SOLKA FLOK was rinsed with MeOH (200 mL×2). The combined MeOH solutions were concentrated under reduced pressure to yield crude product as a white solid (153 g). The crude product was slurried in EtOAc (800 mL), warmed to 40° C. and aged for 30 min. The solution was then seeded, aged for 30 min, and heptane (500 mL) was added via addition funnel over 30 min. The partially crystallized solid was cooled to RT and aged overnight after which additional heptane (500 mL) was added. After 1 h, additional heptane (250 mL) was added via addition funnel, and the white slurry aged for 1 h. The solution was filtered, and the solid was rinsed with heptane/EtOAc (500 mL, 4:1) and dried under reduced pressure to give tert-butyl((1R,2R)-1-{[(cyclopropylsulfonyl)amino]carbonyl}-2-ethylcyclopropyl)carbamate (125.9 g).

Step 2: (1R,2R)-1-Amino-N-(cyclopropylsulfonyl)-2-ethylcyclopropanecarboxamide hydrochloride (Intermediate A3)

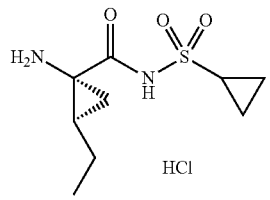

A solution of the product from step 1 above (92 g, 0.28 mol) in DCM (1200 mL) was cooled to 0° C., and HCl was bubbled through the solution. After 10 min, the cooling bath was removed, and the reaction mixture was stirred for 2 h. Nitrogen was bubbled through the reaction mixture for 5 min, and the volatiles evaporated. The residue was azeotroped with DCM (×3) to give an off white powder (75 g). LRMS (M+H)⁺ Calcd.=233; found 233.

Synthesis of Intermediates B

Intermediate B1: (2S)-({[(3R)(3S)-3-(Allyloxy)piperidin-1-yl]carbonyl}amino)(cyclohexyl) acetic acid

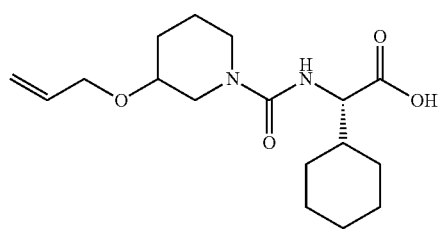 [SMILES: C=CCOC1CCCN(C(=O)N[C@H](C(=O)O)C2CCCCC2)C1]

Step 1: tert-Butyl (3R)(3S)-3-(allyloxy)piperidine-1-carboxylate (2)

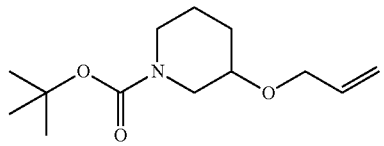

An oven-dried 3-neck 1 L round-bottom flask under nitrogen was charged with N—BOC-(3R)(3S)-3-hydroxypiperidine (10.0 g, 49.7 mmol) and DMSO (100 mL). Potassium tert-butoxide (5.58 g, 49.7 mmol) was added in a single portion. The reaction mixture was stirred at RT for 0.5 h, after which allyl bromide (4.30 mL, 49.7 mmol) in DMSO (50 mL) was added dropwise via an addition funnel. After 20 h, the contents of the reaction flask were poured into 5% KHSO₄ and extracted three times with Et₂O. The combined organic portions were washed with brine, dried with anhydrous MgSO₄, filtered and evaporated. The crude product was subjected to flash column chromatography (90/10, hexanes/EtOAc). Evaporation of fractions containing product gave the title compound as a colorless oil. LRMS (M+1)=242.3.

Step 2: (3R)(3S)-3-(Allyloxy)piperidine (3)

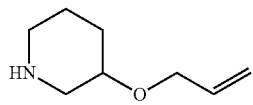

A 500 mL round-bottom flask was charged with tent-butyl (3R)(3S)-3-(allyloxy)piperidine-1-carboxylate (9.60 g, 39.8 mmol) and EtOAc (150 ml) then cooled in an ice bath under nitrogen. The reaction solution was saturated with HCl (g) and stirred 1 h with cooling, then 2 h at RT. Evaporation under reduced pressure gave a white solid, which was triturated with Et₂O and isolated. The solid was poured into 10M NaOH(aq) and extracted three times with DCM, dried with anhydrous MgSO₄, filtered and rotary evaporated to give the title compound as a colorless oil.

Step 3: Methyl (2S)-cyclohexyl(isocyanato)acetate (5)

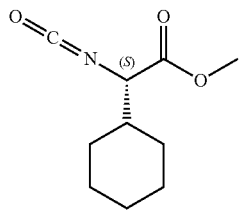

A 500 mL round-bottom flask was charged with saturated NaHCO₃ (80 mL) and DCM (80 ml) and cooled in an ice bath with vigorous stirring. Methyl (2S)-amino(cyclohexyl)acetate hydrochloride (4.0 g, 19.26 mmol) was added followed by triphosgene (1.886 g, 6.36 mmol). The contents of the reaction flask were stirred for 1 hr with cooling, then poured into a reparatory funnel. The layers were separated, and the aqueous layers were extracted with 20 mL DCM. The combined organic portions were dried with anhydrous MgSO₄, filtered and evaporated to give the title compound as a colorless oil. ¹H NMR (CDCl₃): δ 3.90 (d, J 4, 1H), 3.81 (s, 3H), 1.88-1.83 (m, 1H), 1.79-1.76 (m, 2H), 1.69-1.62 (m, 2H), 1.54-1.48 (m, 1H), 1.29-1.11 (m, 5H) ppm.

Step 4: Methyl(2S)-({[(3R)(3S)-3-(allyloxy)piperidin-1-yl]carbonyl}amino)(cyclohexyl)acetate (6)

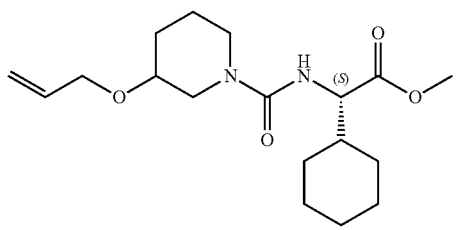

A 500 mL round-bottom flask was charged with methyl (2S)-cyclohexyl(isocyanato)acetate (3.80 g, 19.27 mmol) and THF (50 ml). (3R)(3S)-3-(allyloxy)piperidine (3.80 g, 19.27 mmol) was added, and the resulting solution stirred 24 h at RT. Evaporation followed by flash column chromatography (60 hexane/40 EtOAc) gave the title compound as a colorless oil. LRMS (M+1)=339.3.

Step 5: (2S)-({[(3R)(3S)-3-(Allyloxy)piperidin-1-yl]carbonyl}amino)(cyclohexyl)acetic acid (Intermediate B1)

A 500 mL round-bottom flask was charged with methyl (2S)-({[(3R)(3S)-3-(allyloxy)piperidin-1-yl]carbonyl}amino)(cyclohexyl)acetate (7.00 g, 20.68 mmol), MeOH (20 ml), and THF (20 ml). LiOH (1M, 62.0 ml, 62.0 mmol) was added. The resulting solution was stirred at RT for 18 h. The organic solvents were removed under reduced pressure, and the remaining aqueous was poured into 5% KHSO₄. The mixture was extracted three times with EtOAc, the combined organic portions dried with anhydrous MgSO₄, filtered and rotary evaporated to give the title compound as a white foam/oil. LRMS (M+1)=325.3.

Step 6: (2S)-({[(3S) or (3R)-3-(Allyloxy)piperidin-1-yl]carbonyl}amino)(cyclohexyl)acetic acid (Intermediate B1a) (2S)-({[(3R) or (3S)-3-(allyloxy)piperidin-1-yl]carbonyl}amino) (cyclohexyl)acetic acid (Intermediate B1b)

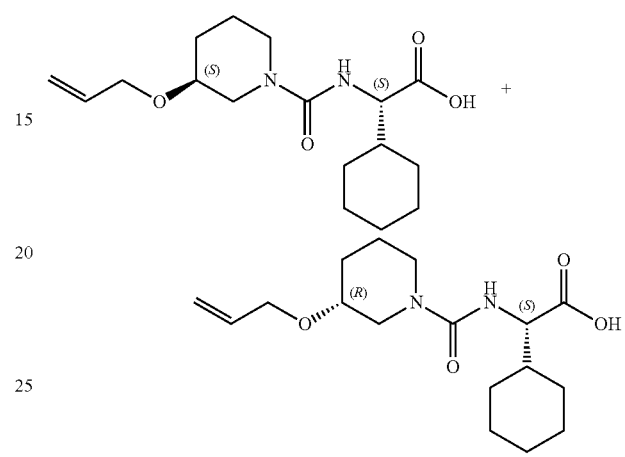

The mixture of diastereomers, (2S)-({[(3R)(3S)-3-(Allyloxy)piperidin-1-yl]carbonyl}amino)(cyclohexyl)acetic acid (4.00 g, 12.33 mmol), was resolved by preparative chiral SFC using the following conditions:
Column: CHIRALPAK AD, 2×25 cm, 10μ
Mobile Phase: 80% CO₂/20% MeOH
Flow: 70 mL/min
Detector: λ=214 nm
Evaporation of like fractions gave the title compounds as colorless oils:
First Eluting Diastereomer:
(2S)-({[(3S) or (3R)-3-(Allyloxy)piperidin-1-yl]carbonyl}amino)(cyclohexyl)acetic acid (1-6) LRMS (M+1)= 325.3.
Second Eluting Diastereomer:
(2S)-({[(3R) or (3S)-3-(allyloxy)piperidin-1-yl]carbonyl}amino)(cyclohexyl)acetic acid (1-7) LRMS (M+1)= 325.3.
The following Intermediates B were prepared according to the procedures described for Intermediate B1 using appropriate amine.

| Intermediate | Amino Acid | Amine | Structure | Name |
|---|---|---|---|---|
| B2 | L-tert-Butylglycine | | 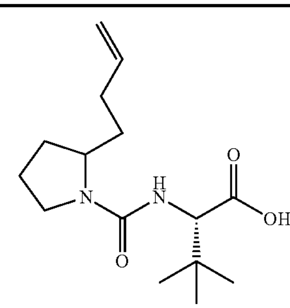 | N-[(2-But-3-en-1-ylpyrrolidin-1-yl)carbonyl]-3-methyl-L-valine |

-continued

| Intermediate | Amino Acid | Amine | Structure | Name |
|---|---|---|---|---|
| B3 | L-cyclohexyl-glycine | N-Boc-(3S)-pyrrolidin-3-ol | 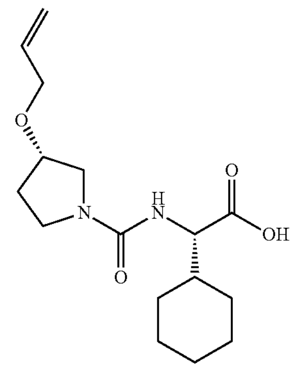 [SMILES: C=CCO[C@H]1CCN(C(=O)N[C@H](C(=O)O)C2CCCCC2)C1] | (2S)-({[(3S)-3-(Allyloxy)pyrrolidin-1-yl]carbonyl}amino)(cyclohexyl)acetic acid |
| B4 | L-cyclohexyl-glycine | N-Boc-(3R)-pyrrolidin-3-ol | 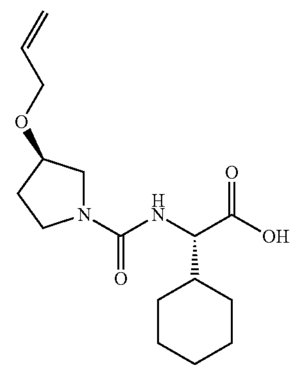 [SMILES: C=CCO[C@@H]1CCN(C(=O)N[C@H](C(=O)O)C2CCCCC2)C1] | (2R)-({[(3S)-3-(Allyloxy)pyrrolidin-1-yl]carbonyl}amino)(cyclohexyl)acetic acid |
| B5 | L-cyclohexyl-glycine | tert-Butyl 3-but-3-en-1-ylpiperidine-1-carboxylate | 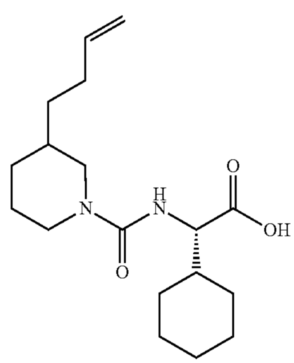 [SMILES: C=CCCC1CCCN(C(=O)N[C@H](C(=O)O)C2CCCCC2)C1] | (2S)-{[(3-But-3-en-1-ylpiperidin-1-yl)carbonyl]amino}(cyclohexyl)acetic acid |
| B6 | L-cyclopentyl-glycine | N-Boc-piperidin-3-ol | 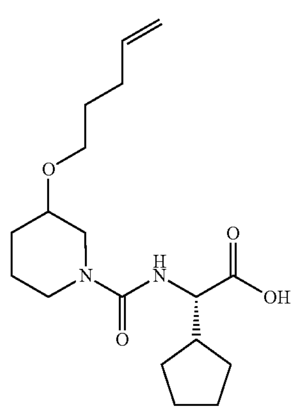 [SMILES: C=CCCCOC1CCCN(C(=O)N[C@H](C(=O)O)C2CCCC2)C1] | (2S)-Cyclopentyl({[(3-(pent-4-en-1-yloxy)piperidin-1-yl]carbonyl}amino)acetic acid |

-continued

| Intermediate | Amino Acid | Amine | Structure | Name |
|---|---|---|---|---|
| B7 | L-cyclopentyl-glycine | N-Boc-piperidin-3-ol | 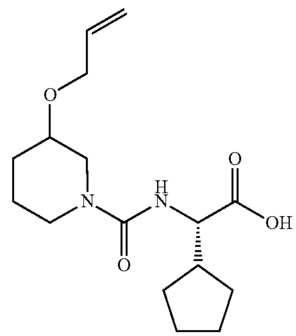 [SMILES: C=CCOC1CCCN(C(=O)N[C@H](C(=O)O)C2CCCC2)C1] | (2S)-({[3-(Allyloxy)piperidin-1-yl]carbonyl}amino)(cyclopentyl)acetic acid |
| B8 | L-cyclopentyl-glycine | N-Boc-(3S)-pyrrolidin-3-ol | 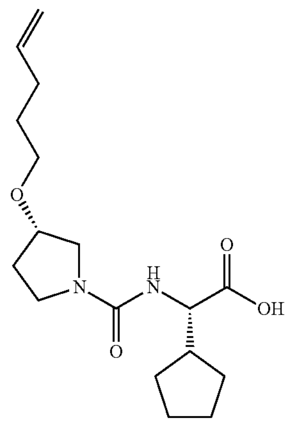 [SMILES: C=CCCCO[C@H]1CCN(C(=O)N[C@H](C(=O)O)C2CCCC2)C1] | (2S)-Cyclopentyl({[(3S)-3-(pent-4-en-1-yloxy)pyrrolidin-1-yl]carbonyl}amino)acetic acid |
| B9 | L-cyclopentyl-glycine | N-Boc(3R)-pyrrolidin-3-ol | 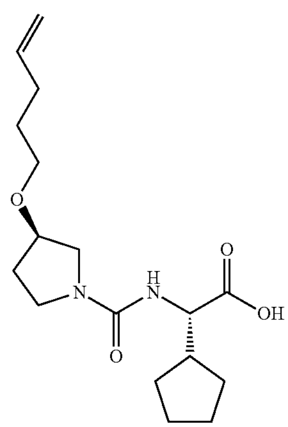 [SMILES: C=CCCCO[C@@H]1CCN(C(=O)N[C@H](C(=O)O)C2CCCC2)C1] | (2S)-Cyclopentyl({[(3R)-3-(pent-4-en-1-yloxy)pyrrolidin-1-yl]carbonyl}amino)acetic acid |
| B10 | L-cyclopentyl-glycine | N-Boc-(3S)-pyrrolidin-3-ol | 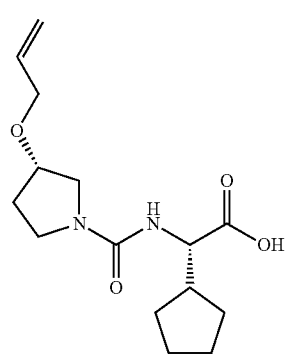 [SMILES: C=CCO[C@H]1CCN(C(=O)N[C@H](C(=O)O)C2CCCC2)C1] | (2S)-({[(3S)-3-(Allyloxy)pyrrolidin-1-yl]carbonyl}amino)(cyclopentyl)acetic acid |

| Intermediate | Amino Acid | Amine | Structure | Name |
|---|---|---|---|---|
| B11 | L-cyclopentyl-glycine | N-Boc-(3R)-pyrrolidin-3-ol | 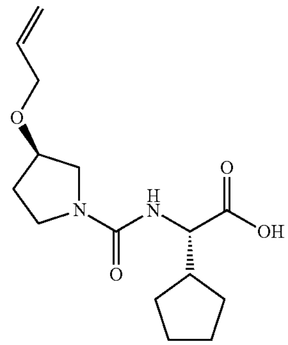 [SMILES: C=CCO[C@@H]1CCN(C(=O)N[C@H](C(=O)O)C2CCCC2)C1] | (2S)-({[(3R)-3-(Allyloxy)pyrrolidin-1-yl]carbonyl}amino)(cyclopentyl)acetic acid |
| B12 | L-cyclopentyl-glycine | N-Boc-(2R)-pyrrolidin-2-ylmethanol | 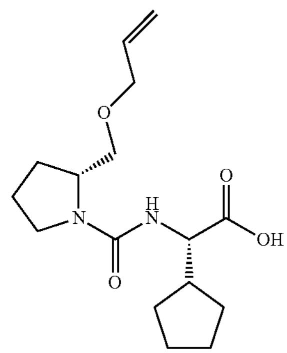 [SMILES: C=CCOC[C@H]1CCCN1C(=O)N[C@H](C(=O)O)C1CCCC1] | (2S)-[({(2R)-2-[(Allyloxy)methyl]pyrrolidin-1-yl}carbonyl)amino](cyclopentyl)acetic acid |
| B13 | L-cyclopentyl-glycine | N-Boc-(2S)-pyrrolidin-2-ylmethanol | 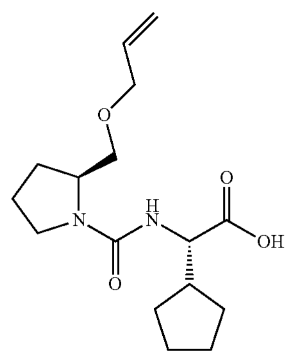 [SMILES: C=CCOC[C@@H]1CCCN1C(=O)N[C@H](C(=O)O)C1CCCC1] | (2S)-[({(2S)-2-[(Allyloxy)methyl]pyrrolidin-1-yl}carbonyl)amino](cyclopentyl)acetic acid |
| B14 | L-cyclopentyl-glycine | (3S)-Pyrrolidin-3-ylmethanol | 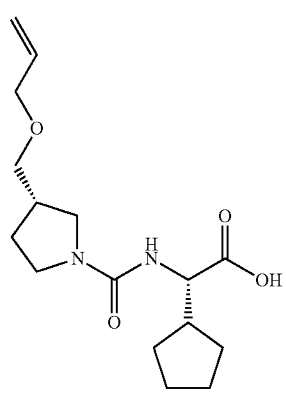 [SMILES: C=CCOC[C@H]1CCN(C(=O)N[C@H](C(=O)O)C2CCCC2)C1] | (2S)-[({(3S)-2-[(Allyloxy)methyl]pyrrolidin-1-yl}carbonyl)amino](cyclopentyl)acetic acid |

-continued

| Intermediate | Amino Acid | Amine | Structure | Name |
|---|---|---|---|---|
| B15 | L-cyclohexyl-glycine | N-Boc-piperidin-4-ol | 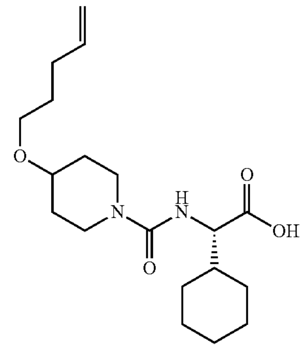 [SMILES: C=CCCCOC1CCN(C(=O)N[C@H](C(=O)O)C2CCCCC2)CC1] | (2S)-Cyclohexyl({[4-(pent-4-en-1-yloxy)piperidin-1-yl]carbonyl}amino)acetic acid |
| B16 | L-cyclohexyl-glycine | N-Boc-azetidin-3-ol | 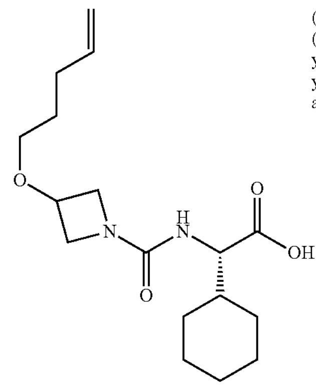 [SMILES: C=CCCCOC1CN(C(=O)N[C@H](C(=O)O)C2CCCCC2)C1] | (2S)-Cyclohexyl({[3-(pent-4-en-1-yloxy)azetidin-1-yl]carbonyl}amino)acetic acid |
| B17 | L-cyclohexyl-glycine | N-Boc-(3S)-pyrrolidin-3-ol | 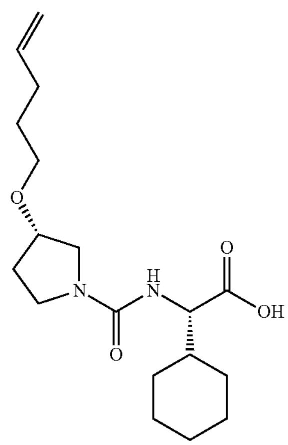 [SMILES: C=CCCCO[C@H]1CCN(C(=O)N[C@H](C(=O)O)C2CCCCC2)C1] | (2S)-Cyclohexyl({[(3S)-3-(pent-4-en-1-yloxy)pyrrolidin-1-yl]carbonyl}amino)acetic acid |

Intermediate B18: tert-Butyl 3-but-en-1-ylpiperidine-1-carboxylate

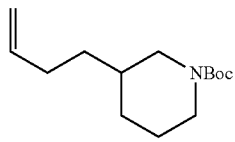 [SMILES: C=CCCC1CCCN(C(=O)OC(C)(C)C)C1]

Step 1: 3-Piperidin-3-ylpropan-1-ol

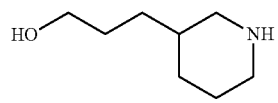

A 500 mL Parr hydrogenation bottle was charged with 3-Pyridinepropanol (10.0 g, 72.9 mmol), platinum(IV)oxide hydrate (Adam's Catalyst) (500 mg), AcOH (30 mL), and HCl, 37% (1 mL). Contents of the bottle were hydrogenated at 47 psi for three days. EtOH and water were added, and the reaction mixture was filtered through CELITE. NaOH (10 N)

was added and the mixture was extracted with methylene chloride, dried with anhydrous MgSO$_4$, filtered and concentrated. The product was concentrated from PhMe and used without further purification. $^1$H NMR (CD$_3$OD): δ 3.55 (t, J=5 Hz, 2H), 3.05 2.95 (m, 2H), 2.55 2.45 (m, 1H), 2.23 (t, J=10 Hz, 1H), 1.89 1.86 (m, 1H), 1.70 1.66 (m, 1H), 1.60 1.44 (m, 4H), 1.28 1.22 (m, 2H), 1.06 1.00 (m, 1H) ppm.

Step 2 tert-Butyl 3-(3-hydroxypropyl)piperidine-1-carboxylate

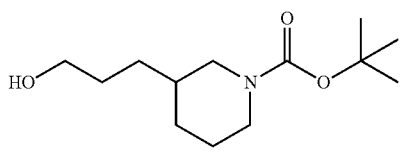 [SMILES: CC(C)(C)OC(=O)N1CCCC(CCCO)C1]

A 500 mL round-bottom flask was charged with 3-piperidin-3-ylpropan-1-ol (10.5 g, 73.1 mmol) and DCM (150 mL), and the mixture was cooled in an ice bath under nitrogen. BOC-Anhydride (18.67 ml, 80 mmol) and DMAP (8.93 mg, 0.073 mmol) were added, and the reaction mixture was warmed to RT and stirred for 18 h. The reaction mixture was poured into 5% KHSO$_4$ and extracted with methylene chloride. The organic layers were washed with 2.5% NaHCO$_3$ and brine, dried with anhydrous MgSO$_4$, filtered and concentrated. Purification by silica gel chromatography (50 hexane/50 EtOAc) gave the title compound. LRMS (M+H)$^+$=244.3.

Step 3 tert-Butyl 3-(3-oxopropyl)piperidine-1-carboxylate

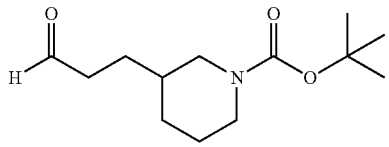 [SMILES: CC(C)(C)OC(=O)N1CCCC(CCC=O)C1]

An oven-dried 3-neck 1 L round-bottom flask under nitrogen was charged with DCM (100 mL) and oxalyl chloride (1.98 mL, 22.6 mmol) and cooled to −60° C. DMSO (3.21 mL, 45.2 mmol) was added dropwise, and the reaction mixture was stirred for 5 min. A solution of tert-butyl 3-(3-hydroxypropyl)piperidine-1-carboxylate (5.00 g, 20.6 mmol) in DCM (100 mL) was added via addition funnel, and the reaction mixture was stirred for 20 min. TEA (14.3 mL, 103 mmol) was added, and the reaction mixture was warmed slowly to RT. The reaction mixture was poured into 2.5% NaHCO$_3$ and extracted with methylene chloride. The combined organic layers were washed with 5% KHSO$_4$ then brine, dried with anhydrous MgSO$_4$, filtered and concentrated. The product was purified by silica gel chromatography (80 hexane/20 EtOAc). LRMS (M+H)$^+$=242.3.

Step 4 tert-Butyl 3-but-3-en-1-ylpiperidine-1-carboxylate

A 1 L oven-dried round-bottom flask was charged with methyltriphenylphosphonium bromide (9.30 g, 26.0 mmol) and THF (250 mL) and cooled to −70° C. A solution of BuLi (2.5 M in hexanes, 10.4 mL, 26.0 mmol) was added dropwise, and the reaction mixture was stirred for 1 h. A solution of tert-butyl 3-(3-oxopropyl)piperidine-1-carboxylate (4.19 g, 17.4 mmol) in THF (15 mL) was added, and the reaction mixture was slowly warmed to RT and stirred for 3 days. The reaction mixture was quenched with water and concentrated to remove THF. The mixture was extracted with EtOAc and the combined organic layers were washed with brine, dried with anhydrous MgSO$_4$, filtered and concentrated. The residue was purified by silica gel chromatography (95 hexane/5 EtOAc) to give the title compound as a colorless oil. $^1$H NMR (CDCl$_3$): δ 5.83-5.77 (m, 1H), 5.04 4.95 (m, 2H), 3.92 3.88 (m, 2H), 2.77 (s, br, 1H)), 2.60 2.35 (m, 1H), 2.11 2.07 (m, 2H), 1.81 (m, 1H), 1.64 1.58 (m, 1H), 1.50 1.20 (m, 13H), 1.25 1.00 (m, 1H) ppm.

Synthesis of Intermediates C

Intermediate C1: Methyl (4R)-4-[(7-methoxy-2-phenyl-6-vinylquinolin-4-yl)oxy]-L-prolinate hydrochloride

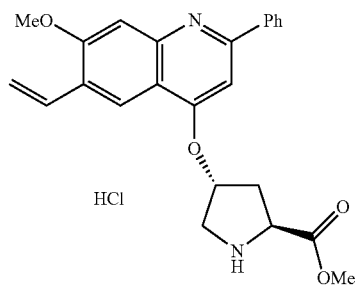 [SMILES: C=Cc1cc2c(O[C@H]3CN[C@H](C(=O)OC)C3)cc(-c3ccccc3)nc2cc1OC ; Cl]

Step 1: Ethyl 3-(methylamino)-3-phenylacrylate

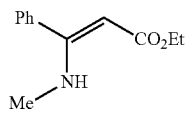

Acetic acid (44.7 mL, 780 mmol) was added to a solution of ethyl benzoylacetate (30 g, 156 mmol) and methyl amine (2M in THF, 390 mL, 780 mmol) in EtOH (150 mL). The reaction mixture was heated to reflux and stirred for 15 h. The reaction mixture was concentrated and partitioned between DCM and 1M HCl. The layers were separated, and the organic layer was dried over Na$_2$SO$_4$, filtered and concentrated to give the title compound (32 g, 99% yield) which was used with no further purification.

Step 2: Ethyl 3-[(4-bromo-3-methoxyphenyl)amino]-3-phenylacrylate

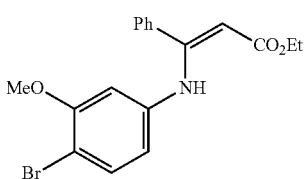 [SMILES: CCOC(=O)/C=C(\Nc1ccc(Br)c(OC)c1)c1ccccc1]

PPTS (38.3 g, 152 mmol) was added to a solution of the product from Step 1 (31.3 g, 152 mmol) and 4-bromo-3-methoxyaniline (28 g, 139 mmol) in DCM (700 mL). The mixture was heated to reflux and stirred for 20 h. The mixture was cooled, and the solids were removed by filtration and washed with DCM. The filtrate was concentrated and purified on silica gel (gradient elution 10% to 50% DCM in hexanes) to give the title compound (49 g, 94% yield). LRMS (M+H)$^+$ Calcd.: 376.0; found 376.2.

Step 3: 6-Bromo-7-methoxy-2-phenylquinolin-4(1H)-one

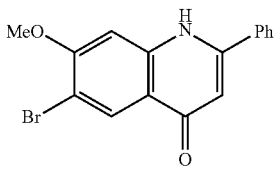 [SMILES: COc1cc2[nH]c(-c3ccccc3)cc(=O)c2cc1Br]

DOWTHERM A (450 mL) was heated to reflux (~300 C). A mixture of the product from step 2 (49 g, 130 mmol) in DOWTHERM A (50 mL) was added to the heated DOWTHERM A solution portionwise. The mixture was stirred at reflux for 30 min after the addition was complete. The mixture was cooled RT, and hexane (400 mL) was added. The mixture was stirred for 30 min and filtered, and the solids were washed with hexane to give the title compound (38 g, 88% yield). LRMS (M+H)$^+$ Calcd.: 330.0; found 330.2.

Step 4: 1-tert-Butyl 2-methyl (2S,4S)-4{([(4-bromophenyl)sulfonyl]oxy}pyrrolidine-1,2-dicarboxylate

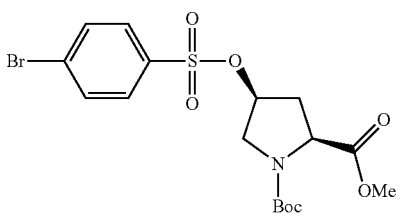 [SMILES: COC(=O)[C@@H]1C[C@H](OS(=O)(=O)c2ccc(Br)cc2)CN1C(=O)OC(C)(C)C]

A solution of brosyl chloride (3.14 g, 12.3 mmol) in PhMe (5 mL) was added to a solution of 1-tent-butyl 2-methyl (2S,4S)-4-hydroxypyrrolidine-1,2-dicarboxylate (2.15 g, 8.76 mmol) and DABCO (1.57 g, 14.0 mmol) in PhMe (10 mL) at RT. A white precipitate formed; the reaction mixture was stirred for 20 min and filtered. The filtrate was partitioned between EtOAc and saturated aqueous NaHCO$_3$. The layers were separated, and the organic layer was washed with 1 M HCl, water and brine, dried over Na$_2$SO$_4$, filtered and concentrated. The title compound (4.0 g, 98% yield) was then used without further purification. LRMS (M+Na)$^+$ Calcd.: 488; found 488.

Step 5: 1-tert-Butyl 2-methyl (2S,4R)-4-[(6-bromo-7-methoxy-2-phenylquinolin-4-yl)oxy]pyrrolidine-1,2-dicarboxylate

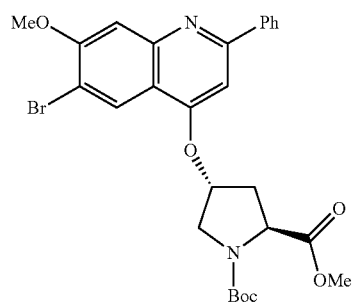 [SMILES: COC(=O)[C@@H]1C[C@@H](Oc2cc(-c3ccccc3)nc3cc(OC)c(Br)cc23)CN1C(=O)OC(C)(C)C]

Cs$_2$CO$_3$ (20.0 g, 61.3 mmol) was added to a solution of the product from step 4 (19.4 g, 41.7 mmol) and the product from step 3 (13.5 g, 40.9 mmol) in N-methylpyrrolidine (200 mL). The reaction mixture was heated to 45° C., stirred for 15 h and cooled. The reaction mixture was poured onto EtOAc and water, and the white solids were removed by filtration. The layers were separated, and the organic layer was washed with saturated aqueous NaHCO$_3$, water and brine, dried over Na$_2$SO$_4$, filtered and concentrated. The residue was purified on silica gel (gradient elution 10% to 50% EtOAc in hexanes) to give the title compound (21.0 g, 92% yield) as a pale yellow solid. LRMS (M+H)$^+$ Calcd.: 557.1; found 557.3.

Step 6: 1-tert-Butyl 2-methyl (2S,4R)-4-[(7-methoxy-2-phenyl-6-vinylquinolin-4-yl)oxy]pyrrolidine-1,2-dicarboxylate

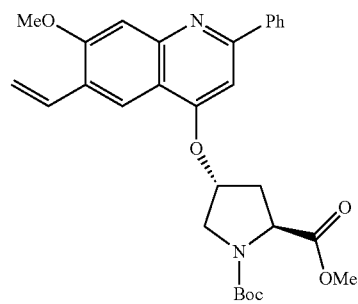 [SMILES: C=Cc1cc2c(O[C@@H]3C[C@@H](C(=O)OC)N(C(=O)OC(C)(C)C)C3)cc(-c3ccccc3)nc2cc1OC]

Potassium vinyltrifluoroborate (5.05 g, 37.7 mmol), TEA (5.25 mL, 37.7 mmol) and PdCl$_2$(dppf)-CH$_2$Cl$_2$ adduct (1025 mg, 1.26 mmol) were added to a solution of the product from step 5 (14.0 g, 21.5 mmol) in EtOH (300 mL). The mixture was then heated to reflux for 1.5 h, at which time LC-MS revealed the disappearance of starting material. The reaction mixture was cooled and concentrated and partitioned between EtOAc and water. The layers were separated, and the organic layer was dried over Na₂SO₄, filtered and concentrated. The residue was purified on silica gel (gradient elution 10% to 80% EtOAc in hexanes) to give the title compound (10.4 g, 82% yield). LRMS (M+H)⁺ Calcd.: 505.2; found 505.5.

Step 7: Methyl (4R)-4-[(7-methoxy-2-phenyl-6-vinylquinolin-4-yl)oxy]-L-prolinate hydrochloride (Intermediate C1)

A solution of the product from step 6 (10.4 g, 20.6 mmol) in dioxane (300 mL) was cooled to 0° C. HCl gas was bubbled through the solution for 20 min. The reaction mixture was warmed to RT and stirred for 2 h. The reaction mixture was concentrated and Et₂O (150 mL) was added, and the mixture was stirred for 1 h. Filtration gave the title compound (9.0 g, 99% yield) as a yellow solid, which was used without further purification. LRMS (M+H)⁺ Calcd.: 405.2; found 405.3.

Intermediate C2: (3R,5S)-5-(Methoxycarbonyl)pyrrolidin-3-yl 4-vinyl-1,3-dihydro-2H-isoindole-2-carboxylate Hydrochloride

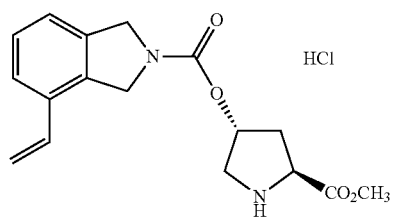 [SMILES: C=Cc1cccc2c1CN(C(=O)O[C@H]1CN[C@H](C(=O)OC)C1)C2 ; Cl]

Step 1: 1-Bromo-2,3-bis(bromomethyl)benzene

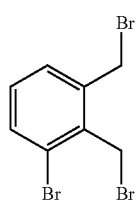

A suspension of 3-bromo-o-xylene (196 g, 1.06 mol), N-bromosuccinimide (377 g, 2.15 mol) and benzoyl peroxide (0.26 g, 1.0 mmol) in carbon tetrachloride (1800 mL) was heated to reflux under nitrogen for 15 h. The contents of the reaction flask were cooled and filtered, and the filtrate evaporated. The crude material was distilled under high vacuum; the major fractions were distilled between 88° C. and 152° C. From these distillates, 108 g of pure material was recovered, and 182 g of slightly crude material, which could be used in the following reaction, was also recovered. ¹H NMR (CDCl₃) δ 7.56 (d, 8.0 Hz, 1H), 7.31 (d, J=8.0 Hz, 1H), 7.26 (s, 1H), 7.16 (t, J=8.0 Hz, 1H), 4.84 (s, 2H), 4.64 (s, 2H) ppm.

Step 2: 2-Benzyl-4-bromoisoindoline

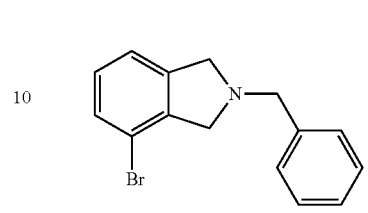

KHSO₄ (204 g, 2.04 mol) was suspended in CH₃CN (12 L), and the mixture was heated to 80° C. Solutions of 1-bromo-2,3-bis(bromomethyl)benzene (280 g, 0.82 mol in 500 mL CH₃CN) and benzylamine (87.5 g, 0.82 mol in 500 mL CH₃CN) were added concurrently via addition funnels over 1 h. The reaction mixture was stirred at 77° C. for 16 h. The contents of the reaction flask were cooled and filtered, and the solvent was removed by evaporation. The reaction was partitioned between 1M K₂CO₃ and EtOAc. The organics were washed with brine, dried with anhydrous Na₂SO₄, filtered and evaporated. Flash column chromatography (gradient elution: heptane to 10% EtOAc in heptane) gave, after evaporation, the title compound as a pale oil. ¹H NMR (CDCl₃) δ 7.41-7.39 (m, 2H), 7.37-7.34 (m, 2H), 7.32-7.27 (m, 2H), 7.10-7.03 (m, 2H), 4.02 (s, 2H), 3.97 (s, 2H), 3.91 (s, 2H), LRMS (ESI) m/z 289 [(M+H)⁺; calcd. for C₁₅H₁₅BrN: 289].

The product was converted to HCl salt in HCl/MeOH by the addition of MTBE and filtration of the solid to give 118 g of product as the HCl salt.

Step 3: 2-Benzyl-4-vinylisoindoline

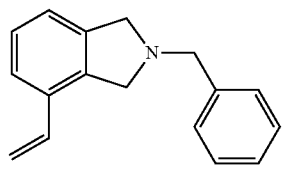 [SMILES: C=Cc1cccc2c1CN(Cc1ccccc1)C2]

A solution of 2-benzyl-4-bromoisoindoline (16.7 g, 58.0 mmol) and tributyl(vinyl)tin (20.3 mL, 69.6 mmol) in PhMe (400 mL) was degassed by bubbling nitrogen gas through the solution for 0.25 h. Tetrakis(triphenylphosphine)palladium (0) (1.30 g, 1.16 mmol) was added, and the resulting solution heated in a 100° C. oil bath under nitrogen for 24 h. The contents of the reaction flask were cooled, evaporated and subjected to flash column chromatography eluting with hexane/EtOAc 95/5 to give after evaporation the title compound as a pale oil that turned pink on standing. LRMS (ESI) m/z 236 [(M+H)⁺; calcd for $C_{17}H_{18}N$: 236].

Step 4: 4-Vinylisoindoline

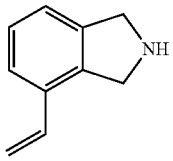

A solution of 2-benzyl-4-vinylisoindoline (58 mmol) in 1,2-dichloroethane (150 mL) was placed in a 1 L round-bottom flask under nitrogen. An addition funnel containing a solution of 1-chloroethyl chloroformate (7.51 mL, 69.6 mmol) in 1,2-dichloroethane was attached to the reaction flask. The reaction flask was cooled in an ice bath, and the contents of the addition funnel were added dropwise over 20 min, keeping the internal reaction temperature <5° C. After the addition was complete, the reaction flask was allowed to warm to RT, then heated to reflux for 45 min. The contents of the reaction flask were cooled to RT, then the solvent was removed by evaporation. MeOH (200 mL) was added, and the contents of the reaction flask were heated to reflux for 30 min. The reaction flask was cooled, and the solvent removed by evaporation. Water (200 mL) was added, and the resulting mixture washed with EtOAc (2×250 mL). The aqueous layer was made basic with 2N NaOH then extracted with methylene chloride (4×250 mL). The combined organic extracts were dried with anhydrous $Na_2SO_4$, filtered and the filtrate evaporated. The remaining residue was subjected to flash column chromatography eluting with methylene chloride/MeOH/$NH_4$OH 97/3/0.3 to 95/5/0.5. Evaporation of fractions gave the title compound as a brown oil, 6.00 g (41.4 mmol, 71% yield for two steps). LRMS (ESI) m/z 146 [(M+H)⁺; calcd for $C_{10}H_{12}N$: 146].

Step 5: 1-tert-Butyl 2-methyl (2S,4R)-4-{[(4-vinyl-1,3-dihydro-2,1-isoindol-2-yl)carbonyl]oxy}pyrrolidine-1,2-dicarboxylate

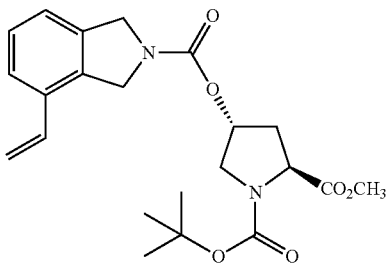 [SMILES: C=Cc1cccc2c1CN(C(=O)O[C@@H]1C[C@@H](C(=O)OC)N(C(=O)OC(C)(C)C)C1)C2]

A solution of 1-tert-butyl 2-methyl (2S,4R)-4-hydroxypyrrolidine-1,2-dicarboxylate (10.1 g, 41.4 mmol) in DMF (90 mL) under nitrogen was cooled to 0° C. Solid 1,1'-carbonyldiimidazole (6.70 g, 41.4 mmol) was added to the reaction. The contents of the reaction flask were warmed to RT, and, after 2 h, a solution of 4-vinylisoindoline (6.00 g, 41.4 mmol) in DMF (10 mL) was added. The reaction was heated in a 60° C. oil bath for 2 h, then cooled and poured into water and 5% $KHSO_4$. The resulting mixture was extracted with EtOAc (4×250 mL). The combined organics were washed with brine, dried with anhydrous $Na_2SO_4$, filtered and evaporated. Flash column chromatography eluting with hexane/EtOAc 70/30 gave the title compound as a white foam, 13.9 g (33.4 mmol, 81% yield). LRMS (ESI) m/z 417 [(M+H)⁺, calcd for $C_{227}H_{29}N_2O_6$: 417].

Step 6: (3R,5S)-5-(Methoxycarbonyl)pyrrolidin-3-yl 4-vinyl-1,3-dihydro-2H-isoindole-2-carboxylate hydrochloride (Intermediate C2)

A solution of 1-tert-Butyl 2-methyl (2S,4R)-4-{[(4-vinyl-1,3-dihydro-2H-isoindol-2-yl)carbonyl]oxy}pyrrolidine-1,2-dicarboxylate (13.9 g, 33.4 mmol) in EtOAc (700 mL) was cooled in an ice bath the saturated with HCl gas. The reaction flask was sealed and allowed to warm to RT. After 3.5 h, the solvent was removed by evaporation to give the title compound as a gray solid, 11.2 g, 95% yield). ¹H NMR (500 MHz, $CD_3OD$) δ 7.47-7.45 (m, 1H), 7.32-7.31 (m, 1H), 7.26-7.21 (m, 1H), 6.79-6.73 (m, 1H), 5.79-5.73 (m, 1H), 5.46 (s, 1H), 5.41-5.38 (m, 1H), 4.80-4.72 (m, 4H), 3.91 (s, 3H), 3.74-3.63 (m, 2H), 2.77-2.71 (m, 1H), 2.51-2.46 (m, 1H). LRMS (ESI) m/z 317 [(M+H)⁺; calcd for $C_{17}H_{21}N_2O_4$: 317].

Intermediate C3: Ethyl (4R)-4-[(6-methoxy-7-vinyl-isoquinolin-1-yl)oxy]-L-prolinate hydrochloride

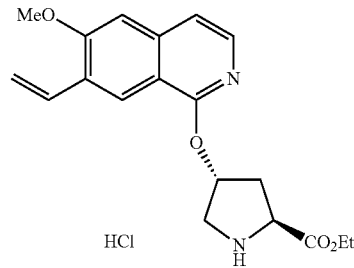 [SMILES: C=Cc1cc2c(O[C@H]3CN[C@H](C(=O)OCC)C3)nccc2cc1OC ; Cl]

Step 1: (2E)-3-(4-Bromo-3-methoxyphenyl)acrylic acid

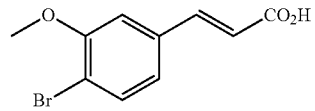

Acrylic acid (9.61 g, 133 mmol), TEA (37.2 mL, 267 mmol) and palladium acetate (719 mg, 3.2 mmol) were added to a solution of 1-bromo-4-iodo-2-methoxybenzene (US 2004/0254159) (33.45 g, 107 mmol) in MeCN (100 mL). The reaction mixture was heated to 90° C. for 40 min, cooled to RT and poured into 2.4 L 1M HCl. After stirring for 30 min, the solid was filtered, heated to reflux in EtOH (230 mL), allowed to cool to RT and stirred overnight. The solid was filtered and washed with 1:1 EtOH:hexanes (50 mL) to give desired product. LRMS ESI⁺ (M+H)⁺ 257.0.

Step 2: 7-Bromo-6-methoxyisoquinolin-1(2H)-one

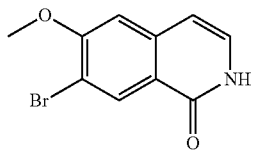

A portion of the product from step 1 [(2E)-3-(4-bromo-3-methoxyphenyl)acrylic acid] (12.5 g, 48.6 mmol) was azeotroped with benzene, suspended in benzene (94 mL) with TEA (9.49 mL, 68.1 mmol) was added diphenylphosphoryl azide (10.48 mL, 48.6 mmol), and the reaction mixture stirred at RT for 1 h. The mixture was filtered through a pad of silica and eluted with ~1 L of PhMe; the volatiles were evaporated; the residue was resuspended in diphenylmethane (94 mL); and the mixture was heated to reflux for three hours (internal temperature 250° C.). The reaction mixture was allowed to cool to RT, stirred overnight and filtered, and the solid washed with hexanes (100 mL) to give tan solid (7.4 g). LRMS ESI⁺ (M+H)⁺254.1.

Step 3: 7-Bromo-1-chloro-6-methoxyisoquinoline

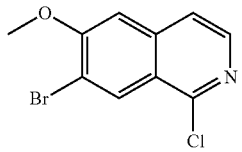

A mixture of the product from step 2 (7-bromo-6-methoxyisoquinolin-1(2H)-one) (4.7 g, 18.5 mmol) in phosphorus oxychloride (30 mL) was heated to reflux. After 2 h, the mixture was cooled to RT; the volatiles were evaporated, and the residue was partitioned between 3M NaOH and DCM. The organic phase was dried over Na₂SO₄; solvent was evaporated; and the solid was triturated with Et₂O (20 mL) and filtered to give a solid (3.75 g). LRMS ESI⁺ (M+H)⁺ 274.0.

Step 4: (4R)-4-[(7-Bromo-6-methoxyisoquinolin-1-yl)oxy]-1-(tert-butoxycarbonyl)-L-proline

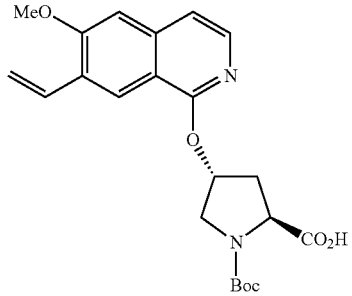 [SMILES: C=Cc1cc2c(O[C@@H]3C[C@@H](C(=O)O)N(C(=O)OC(C)(C)C)C3)nccc2cc1OC]

Potassium tert-butoxide (14.1 g, 125 mmol) was added to a solution of trans 4-hydroxy L-BOC-proline (9.67 g, 41.8 mmol) in DMSO (180 mL) at RT. The reaction mixture was stirred at RT for 30 min and cooled to 15° C. The product from step 3 (11.4 g, 41.8 mmol) was added to the reaction mixture as a solution in DMSO (45 mL); the reaction mixture was allowed to warm to RT and stirred for 30 min. The reaction mixture was quenched with ice-cold 10% citric acid solution and partitioned with EtOAc. The organic layer was washed with aqueous citric acid solution, water and brine, and the aqueous phases were back-extracted with EtOAc. The combined organic phases were dried over anhydrous Na₂SO₄, and the solvent was evaporated. LRMS ESI⁺ (M+H-tBu)⁺411.2.

Step 5: (4R)-1-(tert-Butoxycarbonyl)-4-[(6-methoxy-7-vinylisoquinolin-1-yl)oxy]-proline

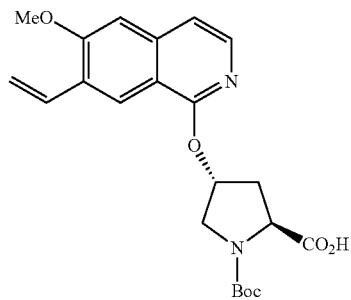 [SMILES: C=Cc1cc2c(O[C@@H]3C[C@@H](C(=O)O)N(C(=O)OC(C)(C)C)C3)nccc2cc1OC]

TEA (0.24 mL, 1.70 mmol) was added to a solution of (4R)-4-[(7-bromo-6-methoxyisoquinolin-1-yl)oxy]-1-(tert-butoxycarbonyl)-L-proline (560 mg, 1.13 mmol) in EtOH (30 mL). Potassium vinyltrifluoroborate (227 mg, 1.70 mmol) and PdCl₂(dppf)-CH₂Cl₂ adduct (46 mg, 0.06 mmol) were then added, and the reaction mixture was stirred at 100° C. for 18 h. The reaction mixture was worked up with EtOAc and water, and the layers were separated. The organic layer was washed with brine, dried over MgSO₄, filtered and concentrated. The crude material was purified on silica (40% EtOAc/hexanes) to yield the title compound as an oil. LRMS (M+H)⁺= 443.4.

Step 6: Ethyl (4R)-4-[(6-methoxy-7-vinylisoquinolin-1-yl)oxy]-L-prolinate hydrochloride Intermediate C3

The product from step 4 (41.8 g, 89 mmol) was dissolved in EtOH (400 mL), and the mixture was cooled to 0° C. HCl was bubbled through the solution, until the solution was saturated. The reaction mixture was then stirred at RT for 60 h, and the volatiles were evaporated under reduced pressure. The solid was triturated in Et₂O (300 mL) and EtOH (50 mL) and filtered to give the title product (33.0 g, 85% yield) as a gray solid. LRMS ESI⁺ (M+H)⁺395.2.

Intermediate C4: Methyl (4R)-4-[(2-ethoxy-methoxy-6-vinylquinolin-4-yl)oxy]-L-prolinate hydrochloride

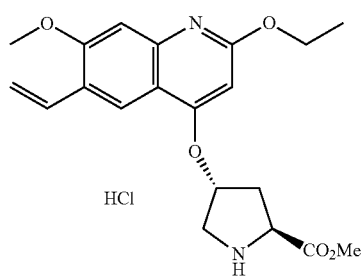 [SMILES: C=Cc1cc2c(O[C@H]3CN[C@H](C(=O)OC)C3)cc(OCC)nc2cc1OC ; Cl]

Step 1:
6-Bromo-4-hydroxy-7-methoxyquinolin-2(1H)-one

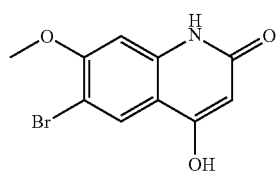

POCl₃ (5.07 ml, 54.4 mmol) was added to a mixture of 4-bromo-3-methoxyaniline (10 g, 49.5 mmol) and malonic acid (5.15 g, 49.5 mmol) with thorough mixing, and the solution was then heated to 105° C. After 5 min, the reaction began to bubble vigorously and eventually formed a hard foam, and heating was continued for 1 h. After cooling, water (200 mL) was added, and the mixture was stirred for 30 min. The solid was filtered off and washed with water. 2N NaOH (300 mL) was added to the solid, and stirring was continued overnight. The remaining solid was filtered off. EtOH (5 mL) was then added to the filtrate, and the basic layer was then acidified with concentrated HCl to pH 2. The resulting solid was then filtered off and washed with water. The solid was then transferred to a flask, and the remaining water was removed by stripping off EtOH (200 mL×2). The solid was then further dried under high vacuum for 15 h to yield 8.75 g (66%) of the title compound as an off-white solid. LRMS EST (M+H)⁺270.2/272.2.

Step 2: 1-tert-Butyl 2-methyl (2S,4R)-4-[(6-bromo-7-methoxy-2-oxo-1,2-dihydroquinolin-4-yl)oxy]pyrrolidine-1,2-dicarboxylate

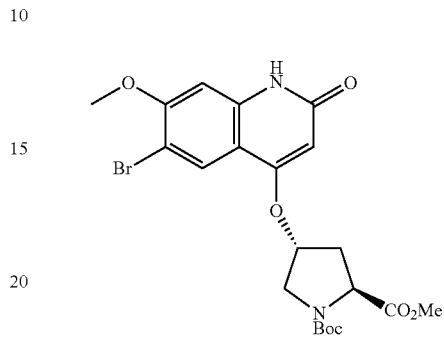

Cs₂CO₃ (8.42 g, 25.8 mmol) was added to a solution of 1-tert-butyl 2-methyl (2S,4S)-4-{[(4-bromophenyl)sulfonyl]oxy}pyrrolidine-1,2-dicarboxylate (4 g, 8.61 mmol) and the product from step 1 (3.49 g, 12.92 mmol) in NMP (86 ml) under nitrogen. The mixture was then heated to 60° C. After 6.5 h, the reaction was extracted with water and EtOAc. The organic layer was extracted with water and brine and dried over MgSO₄. The solvent was then removed in vacuo. The crude product (6.5 g) was purified on silica (gradient elution, 0-100% EtOAc/hexanes, and then 0-5% MeOH/DCM) to yield 2.26 g (53%) of the title compound. LRMS ESI⁺ ((M-Boc)+H)⁺ 397.3/399.3.

Step 3: 1-tert-Butyl 2-methyl (2S,4R)-4-[(7-methoxy-2-oxo-6-vinyl-1,2-dihydroquinolin-4-yl)oxy]pyrrolidine-1,2-dicarboxylate

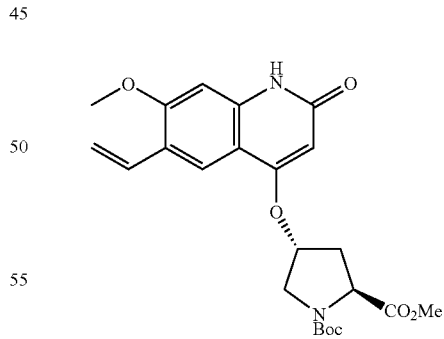

Potassium vinyltrifluoroborate (0.913 g, 6.82 mmol), TEA (0.950 mL, 6.82 mmol), and PdCl₂(dppf)-CH₂Cl₂ adduct (0.186 g, 0.227 mmol) were added to a solution of the product from step 2 (2.26 g, 4.54 mmol) in EtOH (45.4 mL). The mixture was then heated to reflux for 1 h. The EtOH was removed in vacuo, and the residue was taken up in EtOAc and extracted with water. The organic layer was dried over MgSO₄, and the solvent was removed in vacuo. The crude material was purified on silica gradient elution, 0-5% MeOH/DCM) to yield 2.0 g (99%) of the title compound. LRMS ESI+ ((M-Boc)+H)+345.3.

Step 4: 1-tert-Butyl 2-methyl (2S,4R)-4-[(2-ethoxy-7-methoxy-6-vinylquinolin-4-yl)oxy]pyrrolidine-1,2-dicarboxylate

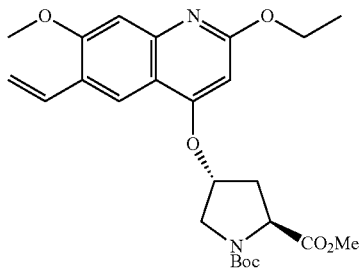 [SMILES: C=Cc1cc2c(O[C@@H]3C[C@@H](C(=O)OC)N(C(=O)OC(C)(C)C)C3)cc(OCC)nc2cc1OC]

Triethyloxonium tetrafluoroborate (1.28 g, 6.75 mmol) was added to a solution of the product from step 3 (2.0 g, 4.5 mmol) in DCM (41 mL). DIEA (0.236 mL, 1.35 mmol) was then added after 15 min. After 45 additional min, the reaction mixture was worked up with NaHCO$_3$ and DCM. The organic layer was then dried over MgSO$_4$, and the solvent was removed in vacuo. The crude material was then purified on silica (gradient elution, 10-60% EtOAc/hexanes) to yield the title compound as an oil. LRMS (M+H)+=473.4.

Step 5: Methyl (4R)-4-[(2-ethoxy-7-methoxy-6-vinylquinolin-4-yl)oxy]-L-prolinate hydrochloride Intermediate C4

HCl gas was bubbled through a solution of the product from step 4 (5 g, 10.6 mmol) in DCM (105 mL) for 10 min, and then the mixture was stirred for 1 h. The solvent was then removed in vacuo to yield the title compound as a white solid. LRMS (M+H)+=373.4.

Intermediate C5: Methyl (4R)-4-[(3-vinylquinolin-2-yl)oxy]-L-prolinate hydrochloride

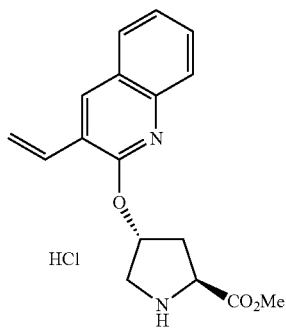 [SMILES: C=Cc1cc2ccccc2nc1O[C@H]1CN[C@H](C(=O)OC)C1 ; Cl]

Intermediate C5 can be prepared according to the procedure described for Intermediate C6 using 3-bromoquinoline instead of 3-bromo-7-methoxyquinoline in step 1.

Intermediate C6: Methyl (4R)-4-[(7-methoxy-3-vinylquinolin-2-yl)oxy]-L-prolinate hydrochloride

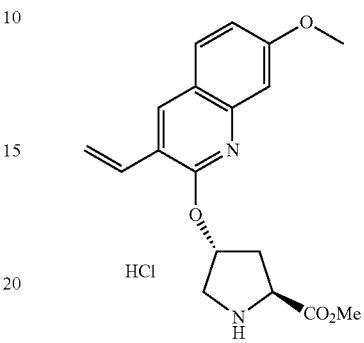

Step 1: 3-Bromo-7-methoxyquinoline 1-oxide

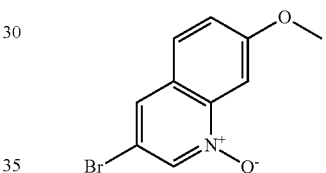

in CPBA (2.9 g, 16.8 mmol) was added to a solution of 3-bromo-7-methoxyquinoline (2.0 g, 8.40 mmol) in DCM (42 mL) at RT, and the reaction mixture was stirred at RT for 1 h. A second portion of mCPBA (2.9 g, 16.8 mmol) was then added, and the reaction mixture was stirred at RT for 18 h. The reaction mixture was poured onto 10% aqueous Na$_2$SO$_3$ and DCM, and the layers were separated. The organic layer was washed with NaHCO$_3$, dried over MgSO$_4$, filtered and concentrated. The resulting product was used with no further purification. LRMS (M+H)+=254.2.

Step 2: 3-Bromo-7-methoxyquinolin-2(1H)-one

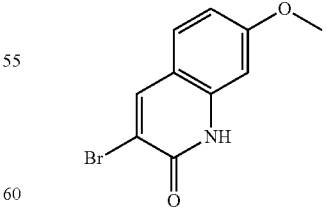

p-Toluenesulfonyl chloride (1.68 g, 8.83 mmol) was added to a solution of 3-bromo-7-methoxyquinoline 1-oxide (2.04 g, 8.03 mmol) in EtOAc (50 mL) and 15% aqueous K$_2$CO$_3$ (15 mL) at RT. The reaction mixture was stirred vigorously at RT for 18 h, at which time the product was collected by filtration and washed with EtOAc. The solid was dried under vacuum and used with no further purification. LRMS (M+H)⁺ =254.1.

Step 3: 1-tert-Butyl 2-methyl (2S,4R)-4-[(3-bromo-7-methoxyquinolin-2-yl)oxy]pyrrolidine-1,2-dicarboxylate

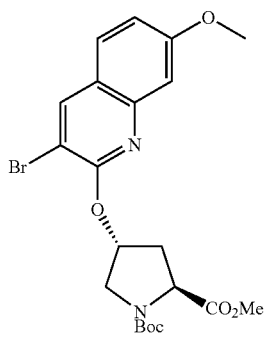 [SMILES: COC(=O)[C@@H]1C[C@@H](Oc2nc3cc(OC)ccc3cc2Br)CN1C(=O)OC(C)(C)C]

Cs₂CO₃ (2.11 g, 6.46 mmol) was added to a solution of 3-bromo-7-methoxyquinolin-2(1H)-one (1.31 g, 5.17 mmol) and 1-text-butyl 2-methyl (2S,4S)-4-{[(4-bromophenyl)sulfonyl]oxy}pyrrolidine-1,2-dicarboxylate (2.0 g, 4.31 mmol) in NMP (21.5 mL), and the reaction mixture was stirred for 40 h at 40° C. An additional portion of 1-tert-butyl 2-methyl (2S,4S)-4-{[(4-bromophenyl)sulfonyl]oxy}pyrrolidine-1,2-dicarboxylate (1.0 g, 2.16 mmol) was added, and the reaction mixture was stirred at 40° C. for 16 h. The reaction mixture was cooled and poured onto a mixture of EtOAc and water, and the layers were separated. The organic layer was washed with water twice, NaHCO₃ twice and brine, dried over Mg₂SO₄, filtered and concentrated. The product was used with no further purification. LRMS (M+H-Boc)⁺=381.2.

Step 4: 1-tert-Butyl 2-methyl (2S,4R)-4-[(7-methoxy-3-vinylquinolin-2-yl)oxy]pyrrolidine-1,2-dicarboxylate

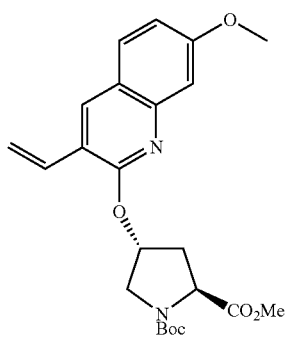 [SMILES: C=Cc1cc2ccc(OC)cc2nc1O[C@@H]1C[C@@H](C(=O)OC)N(C(=O)OC(C)(C)C)C1]

TEA (0.87 mL, 6.23 mmol) was added to a solution of 1-tert-butyl 2-methyl (2S,4R)-4-[(3-bromo-7-methoxyquinolin-2-yl)oxy]pyrrolidine-1,2-dicarboxylate (2.0 g, 4.2 mmol) in EtOH (30 mL). Potassium vinyltrifluoroborate (0.84 g, 6.23 mmol) and PdCl₂(dppf)-CH₂Cl₂ adduct (0.17 g, 0.21 mmol) were then added, and the reaction mixture was stirred at 100° C. for 2 h. The reaction mixture was worked up with EtOAc and water, and the layers were separated. The organic layer was washed with brine, dried over MgSO₄, filtered and concentrated. The crude material was purified on silica (gradient elution, 0-40% EtOAc/hexanes) to yield the title compound as an oil. LRMS (M+H-tBu)⁺=373.3.

Step 5: Methyl (4R)-44(7-methoxy-3-vinylquinolin-2-yl)oxy-L-prolinate hydrochloride Intermediate C6

A solution of 1-tort-butyl 2-methyl (2S,4R)-4-[(7-methoxy-3-vinylquinolin-2-yl)oxy]pyrrolidine-1,2-dicarboxylate (0.85 g, 1.98 mmol) in 4M HCl in dioxane (10 mL) was stirred at RT for 2 h. The reaction mixture was concentrated, and the product was used with no further purification. LRMS (M+H-tBu)⁺=329.3.

Intermediate C7: Methyl (4R)-4-[(2-chloroquinolin-3-yl)oxy]-L-prolinate hydrochloride

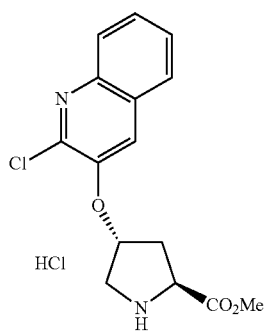 [SMILES: COC(=O)[C@@H]1C[C@@H](Oc2cc3ccccc3nc2Cl)CN1 ; Cl]

Step 1: 2-chloroquinolin-3-ol

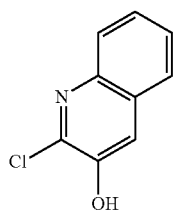 [SMILES: Oc1cc2ccccc2nc1Cl]

A suspension of 2-chloroquinoline-3-boronic acid (15 g, 72.3 mmol) and NH₄Cl (7.16 g, 134 mmol) in Et₂O:H₂O (600 mL) was treated dropwise with aqueous H₂O₂ (30%, 62 mL, 709 mmol). The mixture was stirred for 16 h. Then, the precipitate was filtered, washed with water and Et₂O, and dried at 60° C. over P$_2$O$_5$ to afford the title compound (11.5 g, 89%). LCMS (ES+) m/z 180 (M+H)+.

Step 2: 1-tert-Butyl 2-methyl (2S,4R)-4-[(2-chloro-quinolin-3-yl)oxy]pyrrolidine-1,2-dicarboxylate

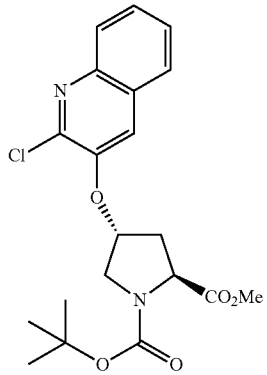 [SMILES: COC(=O)[C@@H]1C[C@@H](Oc2cc3ccccc3nc2Cl)CN1C(=O)OC(C)(C)C]

A solution of the 2-chloroquinolin-3-ol (4.00 g, 22.27 mmol), 1-tert-butyl 2-methyl (2S,4S)-4-hydroxypyrrolidine-1,2-dicarboxylate (5.74 g, 23.38 mmol) and PPh$_3$ (7.01 g, 26.7 mmol) in anhydrous THF (250 mL) was cooled to 0° C. and treated dropwise with DEAD (4.65 g, 26.7 mmol). The mixture was stirred for 3 h at 20° C., then treated at 0° C. with further PPh$_3$ (1.75 g, 6.67 mmol) and DEAD (1.16 g, 6.67 mmol). After stirring for 3 h at 20° C., the mixture was concentrated, and the residue was purified on silica column (15% EtOAc in petroleum ether) to furnish the title compound (5.08 g, 56%) as a white solid. LCMS (ES+) m/z 307 (M+H-Boc)+.

Step 3: Methyl (4R)-4-[(2-chloroquinolin-3-yl)oxy]-L-prolinate hydrochloride

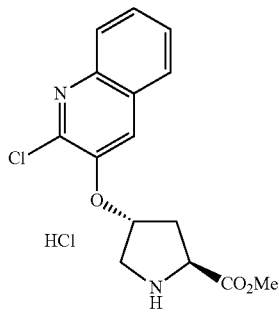 [SMILES: COC(=O)[C@@H]1C[C@@H](Oc2cc3ccccc3nc2Cl)CN1 ; Cl]

A solution of 1-tert-butyl 2-methyl (2S,4R)-4-[(2-chloroquinolin-3-yl)oxy]pyrrolidine-1,2-dicarboxylate (8.9 g, 21.9 mmol) in HCl/dioxane (4 N, 80 mL) was prepared at 0° C. The mixture was stirred for 1 h at 0° C., then at 20° C. for 2 h. Further HCl/dioxane (4 N, 10 mL) was added, and the mixture was stirred for another 1 h. Removal of the volatiles and trituration of the residue with Et$_2$O afforded the title compound (7.19 g, 96%) as a solid that was used directly in subsequent steps. LCMS (ES+) m/z 307 (M+H)+.

Intermediate C8: (2S,4R)-4-[(2-bromo-6-methoxyquinolin-3-yl)oxy]-2-(methoxycarbonyl)pyrrolidinium chloride

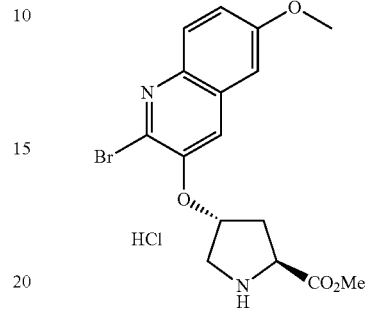

Step 1: 2-Bromo-6-methoxyquinoline

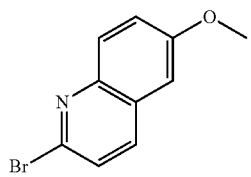

6-Methoxyquinolin-2(1H)-one (6.81 g, 38.9 mmol) was carefully added to POBr$_3$ (18.9 g, 66.1 mmol) at 60° C., and the resulting solution was stirred at 140° C. for 2.5 h. The reaction mixture was cooled and poured onto crushed ice, and the solid was collected by filtration. Purification of this material on silica gel (gradient elution from 5 to 12% EtOAc in petroleum ether) afforded the title compound (4.57 g, 49.3%) as a solid. LCMS (ES+) m/z 238, 240 (M+H)+.

Step 2: (2-Bromo-6-methoxyquinolin-3-yl)boronic acid

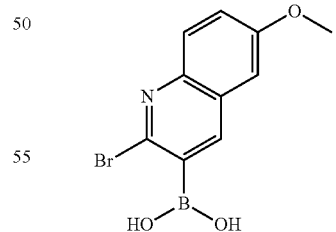

n-BuLi (1.6 N in hexanes, 14.4 mL, 23.0 mmol) was added at −78° C. to a solution of 2,2,6,6-tetramethylpiperidine (3.11 g, 22.05 mmol) in anhydrous THF (59 mL), and the mixture was then warmed to 0° C. for 0.5 h. The mixture was cooled back to −78° C. and treated with a solution of 2-bromo-6-methoxyquinoline (4.57 g, 19.17 mmol) in THF (14 mL). After stirring for 1 h, a solution of trimethyl borate (2.46 mL, 22.05 mmol) in THF (14 mL) was added, and the mixture was maintained at −78° C. for a further 2 h. A mixture of THF (14 mL) and H₂O (3.5 mL), were added then the solution was warmed to −10° C. and treated with water (70 mL) and Et₂O (70 mL). Aqueous NaOH (1 N, 75 mL) was added, and the aqueous layer was separated and acidified to pH 4 with aqueous HCl (3 N). The aqueous phase was extracted with Et₂O, and the combined extracts were washed with brine and dried over Na₂SO₄. Filtration and removal of the volatiles afforded the title compound (4.64 g, 86% yield) as an oily solid that was used directly in the subsequent step. LCMS (ES+) m/z 282, 284 (M+H)⁺.

Step 3: 2-Bromo-6-methoxyquinolin-3-ol

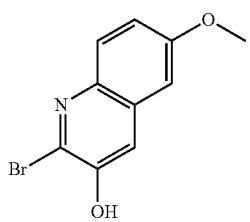

Aqueous H₂O₂ (30%, 32.8 mL, 321 mmol) was added dropwise to a stirred solution of (2-bromo-6-methoxyquinolin-3-yl)boronic acid (4.64 g, 16.45 mmol) and NH₄Cl (3.29 g, 61.5 mmol) in Et₂O (82 mL) and water (82 mL). After 13 h, NH₄Cl (3.29 g, 61.5 mmol) and aqueous H₂O₂ (30%, 32.8 mL, 321 mmol) were added, and the mixture was stirred for 48 h. The precipitate was collected and washed with water, then dried at 50° C. to afford the title compound (4.18 g, 100%) as a solid that was used directly in the subsequent step. LCMS (ES+) m/z 254, 256 (M+H)⁺, Step 4: 1-tert-Butyl 2-methyl (2S,4R)-4[(2-bromo-6-methoxyquinolin-3-yl)oxy]pyrrolidine-1,2-dicarboxylate

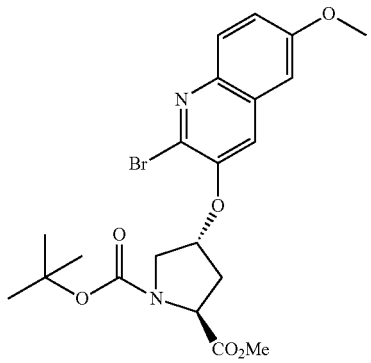 [SMILES: COC(=O)[C@@H]1C[C@@H](Oc2cc3cc(OC)ccc3nc2Br)CN1C(=O)OC(C)(C)C]

Cs₂CO₃ (10.7 g, 32.9 mmol) was added to a stirred mixture of 1-tert-butyl 2-methyl (2S,4S)-4-{[(4-bromophenyl)sulfonyl]oxy}pyrrolidine-1,2-dicarboxylate (8.78 g, 18.9 mmol) and 2-bromo-6-methoxyquinolin-3-ol (4.18 g, 16.45 mmol) in NMP (46 mL). The resulting mixture was stirred at 50° C. for 3 h, then cooled and diluted with EtOAc. The organics were washed with saturated aqueous NaHCO₃, water and brine then dried over Na₂SO₄. Filtration and removal of the volatiles gave a residue, which was purified by column chromatography on silica gel (gradient elution: 1 to 100% EtOAc in petroleum ether) to give the title compound (5.56 g, 70.2%). LCMS (ES+) m/z 481, 483 (M+H)⁺.

Step 5: (2S,4R)-4-[(2-Bromo-6-methoxyquinolin-3-yl)oxy]-2-(methoxycarbonyl)pyrrolidinium chloride

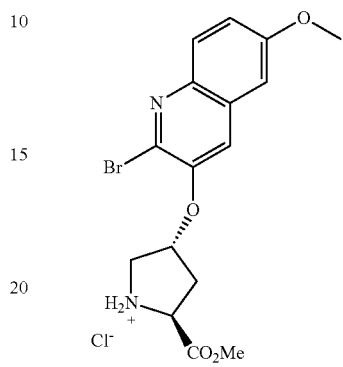

A solution of 1-tert-butyl 2-methyl (2S,4R)-4-[(2-bromo-6-methoxyquinolin-3-yl)oxy]pyrrolidine-1,2-dicarboxylate (5.01 g, 10.40 mmol) in HCl/dioxane (4 N, 31 ml) was prepared at 0° C. and the mixture was stirred at 20° C. for 40 min. The volatiles were evaporated and the residue was triturated with Et₂O to afford an approximately 1:1 mixture of the title compound and (2S,4R)-4-[(2-chloro-6-methoxyquinolin-3-yl)oxy]-2-(methoxycarbonyl)pyrrolidinium chloride (4.34 g) as a solid that was used directly in subsequent steps. LCMS (ES+) m/z 381, 383 (M+H)⁺.

Intermediate C9: Methyl 4R)-4-[(3-allyl-1-methyl-3H-pyrrolo[2,3-c]quinolin-4-yl)oxy]-L-prolinate

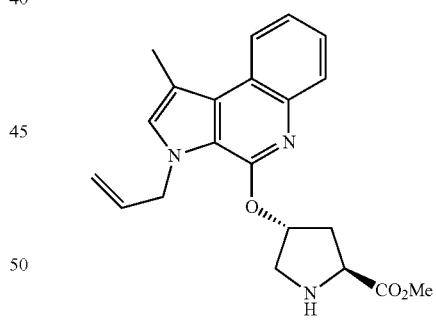

Step 1: 1-Nitro-2-[2-nitroprop-1-en-1-yl]benzene

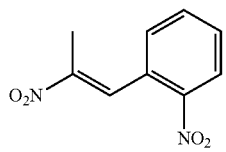

A solution of 2-nitrobenzaldehyde (5.0 g, 33.1 mmol) and ammonium acetate (2.55 g, 33.1 mmol) in AcOH (20 mL)

was treated dropwise at 20° C. with nitroethane (2.84 mL, 39.7 mmol). The resulting solution was heated under reflux for 2 h, then cooled and diluted with EtOAc. The organic layer was washed with saturated aqueous NaHCO$_3$ solution and brine, then dried over Na$_2$SO$_4$. Filtration and removal of the volatiles gave a residue that was purified on silica gel (gradient elution, 0-40% EtOAc/hexanes) to give the title compound as an oil (2.3 g, 33%). LCMS (ES+) m/z 209 (M+H)$^+$.

Step 2: Ethyl 4-methyl-3-(2-nitrophenyl)-1H-pyrrole-2-carboxylate

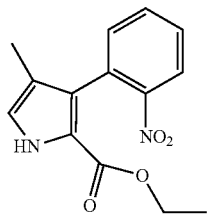 [SMILES: CCOC(=O)c1[nH]cc(C)c1-c1ccccc1[N+](=O)[O-]]

A solution of 1-nitro-2-[2-nitroprop-1-en-1-yl]benzene (4.1 g, 19.7 mmol) in a mixture of THF (131 mL) and tert-BuOH (66 mL) was treated with DBU (4.45 mL, 29.5 mmol) and ethyl isocyanoacetate (2.67 g, 2.58 mL) added. The resulting solution was stirred for 1 h, then heated to 70° C. for 4 h. The mixture was cooled and concentrated in vacuo to give residue that was taken up in EtOAc and aqueous HCl (1 N). The organic layer was separated and washed with brine, then dried over Na$_2$SO$_4$. Filtration and solvent removal afforded a residue that was purified on silica gel (gradient elution, 0-40% EtOAc/hexanes) to afford the title compound (3.2 g, 59%) as solid. LCMS (ES+) m/z 275 (M+H)$^+$.

Step 3: 1-Methyl-3H-pyrrolo[2,3-c]quinolin-4-ol

A solution of ethyl 4-methyl-3-(2-nitrophenyl)-1H-pyrrole-2-carboxylate (3.2 g, 11.67 mmol) in AcOH (117 mL) was treated at 20° C. with iron dust (6.52 g, 117 mmol). The reaction mixture was heated at 100° C. for 3 h. The white precipitate was removed by filtration, and the filtrates were concentrated to give a residue that was purified on silica gel (gradient elution, 50-100% MeOH/acetone) to afford the title compound (2.0 g, 86%) as a solid. LCMS (ES+) m/z 199 (M+H)$^+$.

Step 4: 3-Allyl-1-methyl-3H-pyrrolo[2,3-e]quinolin-4-ol

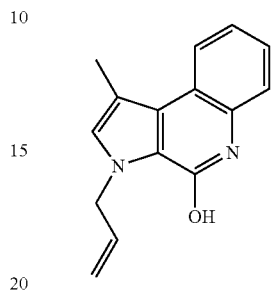

A solution of 1-methyl-3H-pyrrolo[2,3-c]quinolin-4-ol (1.2 g, 6.05 mmol) in a mixture of THF (30 mL) and NMP (60 mL) was treated with Cs$_2$CO$_3$ (2.95 g, 9.08 mmol). Allyl bromide (0.524 mL, 6.06 mmol) was added dropwise, and the resulting mixture was stirred at 40° C. for 12 h. The mixture was cooled and quenched with aqueous HCl (1 N) and EtOAc. The organic layer was separated, washed with aqueous HCl (1 N), brine, and dried over Na$_2$SO$_4$. Filtration and removal of the volatiles gave a residue that was triturated with Et$_2$O to give the title compound (0.78 g, 54%) as a solid. LCMS (ES+) m/z 239 (M+H)$^+$.

Step 5: 1-tert-Butyl 2-methyl (2S,4R)-4-[(3-allyl-1-methyl-3H-pyrrolo[2,3-e]quinolin-4-yl)oxy]pyrrolidine-1,2-dicarboxylate

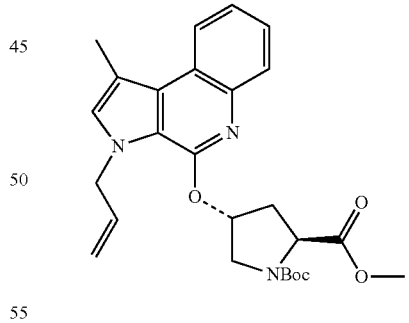

Cs$_2$CO$_3$ (8.20 g, 25.20 mmol) and 1-tert-butyl 2-methyl (2S,4S)-4-{[(4-bromophenyl)sulfonyl]oxy}pyrrolidine-1,2-dicarboxylate (3.80 g, 8.18 mmol) were added in sequence to a solution of 3-allyl-1-methyl-3H-pyrrolo[2,3-e]quinolin-4-ol (1.50 g, 6.29 mmol) in NMP (42 mL). The mixture was heated at 60° C. for 12 h, then cooled and diluted with EtOAc and aqueous HCl (1 N). The organic layer was separated, washed with brine and dried over Na$_2$SO$_4$. Filtration and removal of the volatiles gave a residue that was purified on silica gel (gradient elution, 20-100% EtOAc/petrol ether) to afford the title compound (1.30 g, 44%) as a solid. LCMS (ES+) m/z 466 (M+H)$^+$.

Step 6: Methyl (4R)-4-[(3-allyl-1-methyl-3H-pyrrolo [2,3-c]quinolin-4-yl)oxy]-L-prolinate

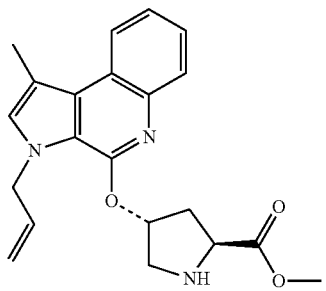

TFA (3 mL) was added to a solution of 1-tert-butyl 2-methyl (2S,4R)-4-[(3-allyl-1-methyl-3H-pyrrolo[2,3-c]quinolin-4-yl)oxy]pyrrolidine-1,2-dicarboxylate (1.30 g, 2.79 mmol) in DCM (20 mL). The mixture was stirred for 4 h, then diluted with PhMe and concentrated under reduced pressure. The residue was taken up in EtOAc and washed with saturated aqueous NaHCO$_3$ and brine. The organic phase was dried over Na$_2$SO$_4$ and concentrated to give the title compound (1.02 g, 98%) as an oil that was used without further purification in subsequent steps. LCMS (ES+) m/z 366 (M+H)$^+$.

Intermediate C10: (2S,4R)-4-[(3-Chloroquinoxalin-2-yl)oxy]-2-(methoxycarbonyl)pyrrolidinium chloride

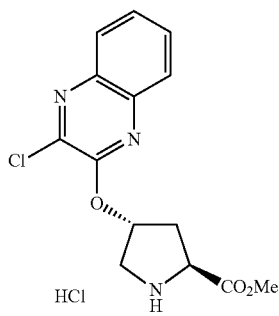 [SMILES: COC(=O)[C@@H]1C[C@@H](Oc2nc3ccccc3nc2Cl)CN1 ; Cl]

Step 1: 1-tert-Butyl 2-methyl (2S,4R)-4-[(3-chloroquinoxalin-2-yl)oxy]pyrrolidine-1,2-dicarboxylate A solution of 3-chloroquinoxalin-2-ol (1.44 g, 7.97 mmol) and 1-tert-butyl 2-methyl (2S,4S)-4-hydroxypyrrolidine-1,2-dicarboxylate (2.05 g, 8.37 mmol) in THF (190 ml) was cooled to 0° C., then treated with PPh$_3$ (2.51 g, 9.57 mmol). DIAD (1.86 ml, 9.57 mmol) was added dropwise, and the mixture was stirred at 20° C. for 1 h. After evaporation of the volatiles, the residue was purified on silica gel (gradient elution, 0-70% EtOAc/petroleum ether) to afford the title compound (2.5 g, 77%). LCMS (ES+) m/z 408 (M+H)$^+$.

Step 2: (2S,4R)-4-[(3-Chloroquinoxalin-2-yl)oxy]-2-(methoxycarbonyl)pyrrolidinium chloride A solution of 1-tent-butyl 2-methyl (2S,4R)-4-[(3-chloroquinoxalin-2-yl)oxy]pyrrolidine-1,2-dicarboxylate (1.05 g, 2.57 mmol) in HCl/dioxane (4 N, 5 mL) was prepared at 0° C., then stirred for 2 h at 20° C. The reaction mixture was concentrated to afford a residue that was triturated with Et$_2$O to afford the title compound (0.88 g, 98%) as a white solid that was used directly in subsequent reactions. LCMS (ES+) m/z 308 (M+H)⁺.

Intermediate C11: 1-tert-Butyl 2-methyl (2S,4R)-4 [(2-ethoxy-6-vinylquinazolin-4-yl)oxy]pyrrolidine-1, 2-dicarboxylate hydrochloride

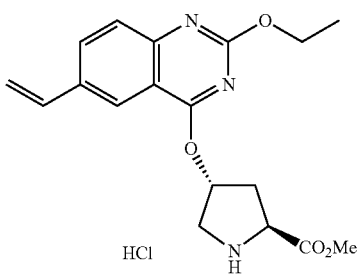 [SMILES: C=Cc1ccc2nc(OCC)nc(O[C@H]3CN[C@H](C(=O)OC)C3)c2c1 ; Cl]

Step 1: 2-Chloro-6-iodoquinazolin-4-ol

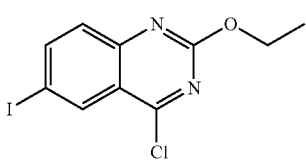

A solution of 2,4-dichloro-6-iodoquinazoline (10 g, 30.8 mmol) in THF (8 ml) and water (8 ml) was treated with aqueous NaOH (1 N, 4 ml). The solution was stirred for 1 h, then diluted with aqueous HCl (1 N) and EtOAc. The organic phase was separated and washed with brine then dried over Na₂SO₄. Filtration and removal of the volatiles afforded the title compound (9.4 g, 100%) as a solid. LCMS (ES+) m/z 307 (M+H)⁺.

Step 2: 2-Ethoxy-6-iodoquinazolin-4-ol

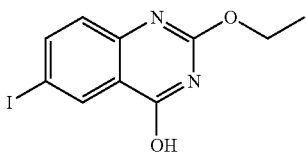

2-Chloro-6-iodoquinazolin-4-ol (3.5 g, 11.42 mmol) was suspended in EtOH and treated with an ethanolic solution of NaOEt (21%, 12.8 ml, 34.3 mmol). The mixture was irradiated at 150° C. in a microwave for 2 h, then was cooled to 20° C. The precipitated product was collected by filtration, and washed with aqueous HCl (1 N) and water. After drying under vacuum, the title compound (3.04 g, 84%) was obtained as a yellow solid. LCMS (ES+) m/z 317 (M+H)⁺.

Step 3: 1-tert-Butyl 2-methyl (2S,4R)-4-[(2-ethoxy-6-vinylquinazolin-4-yl)oxy]pyrrolidine-1,2-dicarboxylate

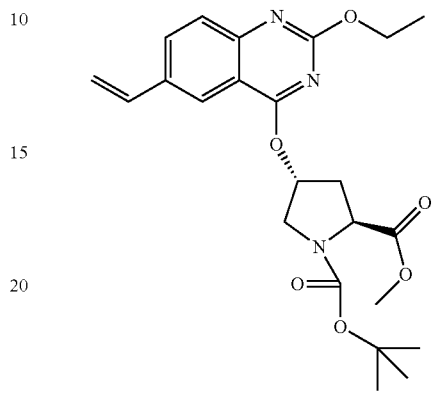

A solution of 2-ethoxy-6-iodoquinazolin-4-ol (2.94 g, 9.30 mmol) and 1-tent-butyl 2-methyl (2S,4S)-4-hydroxypyrrolidine-1,2-dicarboxylate (2.28 g, 9.30 mmol) in THF (150 ml) was cooled to 0° C. and treated with Ph₃P (2.93 g, 11.16 mmol). DEAD (4.42 ml, 11.16 mmol) was added dropwise, and the mixture was stirred at 20° C. for 4 h. After evaporation of the volatiles, the residue was purified on silica gel (gradient elution, 0-5% EtOAc/(EtOAc:DCM=5:95)) to furnish a 6:4 mixture of 1-tert-butyl 2-methyl (2S,4R)-4-[(2-ethoxy-6-iodoquinazolin-4-yl)oxy]pyrrolidine-1,2-dicarboxylate and 1-text-butyl 2-methyl (2S,4R)-4-(2-ethoxy-6-iodo-4-oxoquinazolin-3(4H)-yl)pyrrolidine-1,2-dicarboxylate (3.8 g) LCMS (ES+) m/z 544 (M+H)⁺. This material was dissolved in EtOH (40 mL) and treated with TEA (0.83 mL, 5.98 mmol). Potassium vinyltrifluoroborate (0.80 g, 5.98 mmol) and PdCl₂(dppf)-CH₂Cl₂ adduct (0.32 g, 0.399 mmol) were added, and the mixture was stirred at 90° C. for 2 h. The mixture cooled, diluted with EtOAc and washed with aqueous HCl (1 N) and brine. The organic phase was dried over Na₂SO₄, filtered and concentrated to give a residue that was purified on silica (gradient elution, 0-20% EtOAc/DCM) to yield the title compound as an oil (1.38 g, 33%). LCMS (ES+) m/z 444 (M+H)⁺.

Step 4: Methyl (4R)-4-[(2-ethoxy-6-vinylquinazolin-4-yl)oxy]-L-prolinate

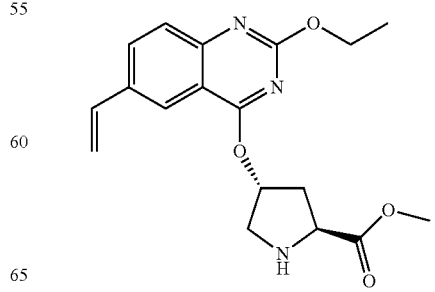

A solution of 1-tert-butyl-2-methyl-(2S,4R)-4-[(2-ethoxy-6-vinylquinazolin-4-yl)oxy]pyrrolidine-1,2-dicarboxylate (1.44 g, 2.20 mmol) in HCl/dioxane (4 N, 5 mL) was prepared at 0° C. and stirred at 20° C. for 1.5 h. The mixture was diluted with EtOAc, then washed with saturated aqueous NaHCO$_3$ and brine, and dried over Na$_2$SO$_4$. Filtration and removal of the volatiles afforded the title compound (0.59 g, 53%) as a solid. This material was used without further purification. LCMS (ES+) m/z 344 (M+H)$^+$.

Intermediate C12: Methyl (4R)-4-[(3-vinyl-2-naphthyl)oxy]-L-prolinate hydrochloride

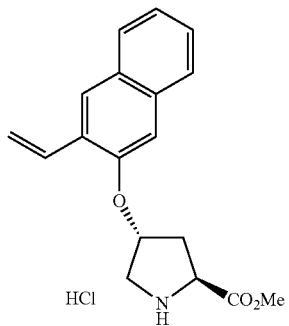 [SMILES: C=Cc1cc2ccccc2cc1O[C@H]1CN[C@H](C(=O)OC)C1 ; Cl]

Intermediate C12 can be prepared according to the procedure described for Intermediate C6, steps 3-5 using 3-bromo-2-naphthol (Edward R. Biehl et al., SYNTHESIS 885 (September 1993); Radoslaw S. Laufer & Gary I. Dmitrienko, 124(9) J. AM. CHEM. SOC. 1854 (2002)) instead of 3-bromo-7-methoxyquinolin-2(1H)-one in step 3.

Example 1

(3R,5S,8S,15S)-8-Cyclohexyl-N-((1R,2S)-1-{[(cyclopropylsulfonyl)amino]carbonyl}-2-vinylcyclopropyl)-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide

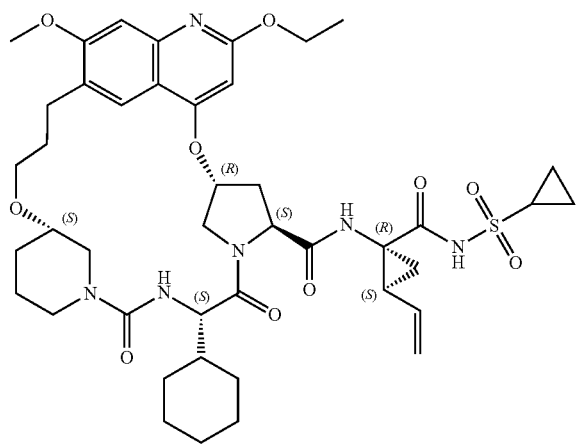

Step 1: Methyl (4R)-1-[(2S)-2-({[(3S)-3-(allyloxy)piperidin-1-yl]carbonyl}amino)-2-cyclohexylacetyl]-4[(2-ethoxy-7-methoxy-6-vinylquinolin-4-yl)oxy]-L-prolinate (7)

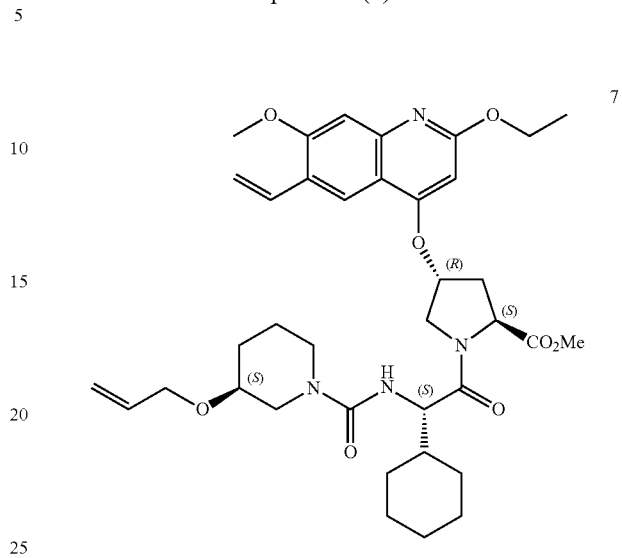

A 100 mL round-bottom flask was charged with Intermediate B1a (291 mg, 0.898 mmol), Intermediate C4 (400 mg, 0.898 mmol), HATU (512 mg, 1.347 mmol), DMF (5.00 ml), DIPEA (0.627 ml, 3.59 mmol), and DMAP (54.9 mg, 0.449 mmol). The reaction solution was stirred at RT for 18 hours, then poured into 2.5% NaHCO$_3$. The mixture was extracted thrice with EtOAc, and the combined organic portions were washed with brine, dried with anhydrous MgSO$_4$, filtered and rotary evaporated. Flash column chromatography (60 EtOAc/40 hexane) gave the title compound as a white foam. LRMS (M+1)=679.3.

Step 2: Methyl (3R,5S,8S,15S,18E)-8-cyclohexyl-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1(27),18,20,22,23,25,27-heptaene-5-carboxylate (8)

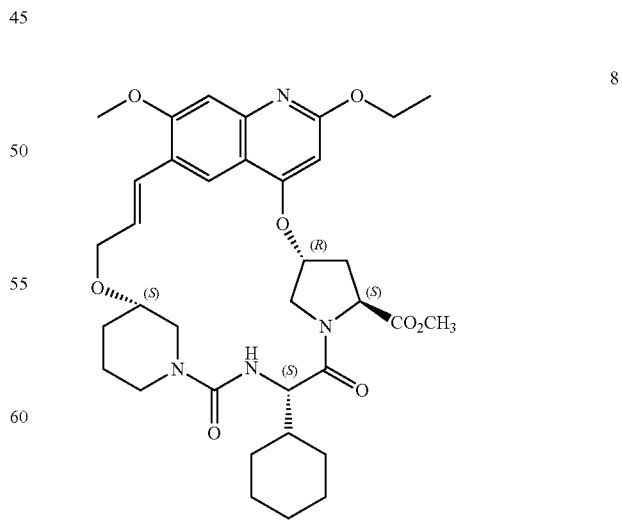

A 500 mL round-bottom flask was charged with the product from step 1 (500 mg, 0.737 mmol) and DCE (150 ml), and the resulting solution degassed with nitrogen for 0.5 h. Dichloro(1,3-dimesitylimidazolidin-2-ylidene){5-[(dimethylamino)sulfonyl]-2-isopropoxy benzylidene}ruthenium catalyst (54.0 mg, 0.074 mmol) was added, and the mixture was heated in a 70° C. oil bath under nitrogen. After 1 h, an additional portion of dichloro(1,3-dimesitylitnidazolidin-2-ylidene){5-[(dimethylamino)sulfonyl]-2-isopropoxy benzylidene}ruthenium catalyst (54.0 mg, 0.074 mmol) was added. After 18 h, the reaction mixture was cooled, evaporated and subjected to flash column chromatography (60 EtOAc/40 hexanes) to give the title compound as a foam. LRMS (M+1)=651.3.

Step 3: Methyl (3R,5S,8S,15S)-8-cyclohexyl-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1 (27), 20, 22, 23,25,27-hexaene-5-carboxylate (9)

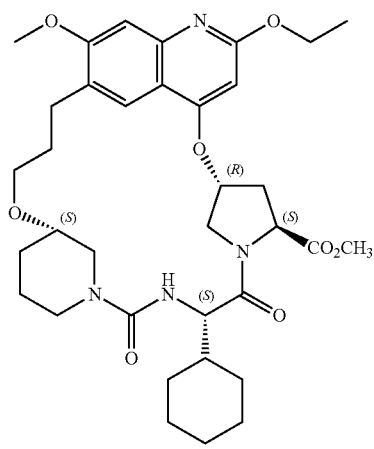

A 100 mL round-bottom flask was charged with the product from step 2 (120 mg, 0.184 mmol) and MeOH (25 mL). 10% Pd/C (34 mg, 0.319 mmol) was added, and the reaction mixture was hydrogenated using a balloon for 48 h. The reaction mixture was filtered through CELITE, and the filtrate evaporated to afford the title compound as a tan foam. LRMS (M+1)=653.3.

Step 4: (3R,5S,8S,15S)-8-Cyclohexyl-25-ethoxy-21-methoxy-7,10-dioxo-2,16-dioxa-6,9,11,24-tetraazapentacyclo[18.6.2.1$^{3,6}$.1$^{11,15}$.0$^{23,27}$]-triaconta-1 (27), 20,22,23,25,27-hexaene-5-carboxylic acid (10)

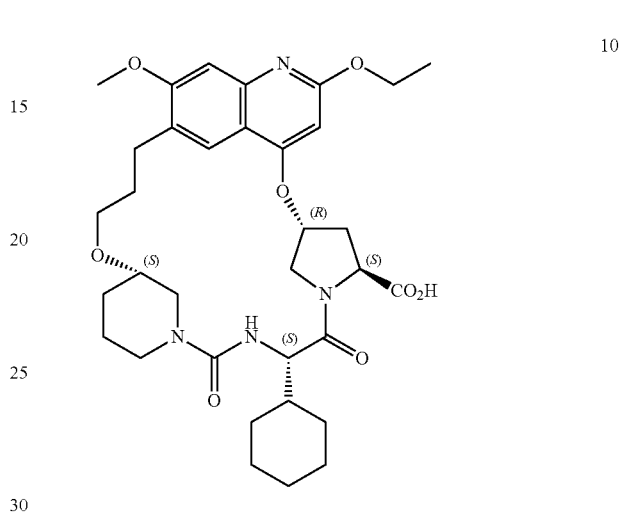

A 100 mL round bottom flask was charged with the product from step 3 (119 mg, 0.182 mmol), MeOH (5.00 mL), THF (5.00 mL), and LiOH (1M, 1.822 mL, 1.822 mmol). The reaction solution was stirred at RT for 48 h, poured into 5% KHSO$_4$ and extracted with thrice with EtOAc. The combined organic portions were washed with brine, dried with anhydrous MgSO$_4$, filtered and rotary evaporated to give the title compound as a foam. LRMS (M+H)$^+$ 639.3.

Step 5: (3R,5S,8S,15S)-8Cyclohexyl-N-((1R,2S)-1-{[(cyclopropylsulfonyl)amino]carbonyl}-2-vinylcyclopropyl-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide (EXAMPLE 1)

A 100 mL round-bottom flask with was charged with the product from step 4 (106 mg, 0.166 mmol), Intermediate A1 (66.4 mg, 0.249 mmol), DMF (2.00 ml), HATU (95 mg, 0.249 mmol), DIPEA (0.087 ml, 0.498 mmol), and DMAP (10.14 mg, 0.083 mmol). The contents of the reaction flask were stirred at RT for 3 h, then subjected to Gilson reverse-phase preparative chromatography using a 0.15% trifluoroacetic acid/CH$_3$CN gradient and a WATERS SUNFIRE PREP C$_{18}$ ODB 5 μm 30×100 min column. Evaporation of fractions containing product gave the title compound as a white foam. $^1$H NMR (CD$_3$OD): δ 9.36 (s, 1H), 7.92 (s, 1H), 7.10 (s, 1H), 6.84 (s, 1H), 5.81-5.74 (m, 2H), 5.29 (d, J=16Hz, 1H), 5.12 (d, J=12 Hz, 1H), 4.75 (d, J=12 Hz, 1H), 4.66-4.62 (m, 2H), 4.45-4.41 (m, 1H), 4.34 (d, J=8 Hz, 1H), 4.09-4.06 (m, 1H), 4.01 (s, 3H), 3.85-3.82(m, 1H), 3.68-3.65 (m, 1H), 3.60-3.55 (m, 1H), 3.47-3.43 (m, 1H), 3.39 (s, br, 1H), 3.10-3.05 (m, 1H), 2.97-2.88 (m, 3H), 2.77-2.65 (m, 2H), 2.42-2.35 (m, 1H), 2.22-2.16 (m, 1H), 1.92-1.57 (m, 14H), 1.45-0.99 (m, 11H) ppm. LRMS (M+H)+=852. Cell-based HCV Replication Assay: IC$_{50}$ 4 nM.

Example 2

(2R,4S,7S,13S,18E)-7-Cyclopentyl-N-(1R,2S)-1-{[(cyclopropylsulfonyl)amino]carbonyl}-2-vinylcyclopropyl)-6,9-dioxo-3,4,6,7,8,9,12,13,16,17-decahydro-2H,11H,15H-2, 5:10,13-diamethano[1,14,5,7,10]dioxatriazacyclohnicosino[15,16-b]quinoxaline-4-carboxamide Step 1: Methyl (4R)-4-[(3-chloroquinoxalin-2-yl)oxy]-1-[(2S)-2-cyclopentyl-2-({[(3S)-3-(pent-4-en-1-yloxy)pyrrolidin-1-yl]carbonyl}amino)acetyl]-L-prolinate (11)

Following the procedure described in example 1, step 1, treatment of a DMF solution of Intermediates B8 (0.2 g, 0.581 mmol) and C11 (0.207 g, 0.639 mmol) with HATU (0.287 g, 0.755 mmol) and DIPEA (0.304 mL, 1.74 mmol) afforded the title compound (0.357 g, 59%) as a solid. LCMS (ES+) m/z 615 (M+H)+.

Step 2: Methyl (4R)-1-[(2S)-2-cyclopentyl-2-({[(3S)-3-(pent-4-en-1-yloxy)pyrrolidin-1-yl]carbonyl}amino)acetyl]-4-[(3-vinylquinoxalin-2-yl)oxy]-L-prolinate (12)

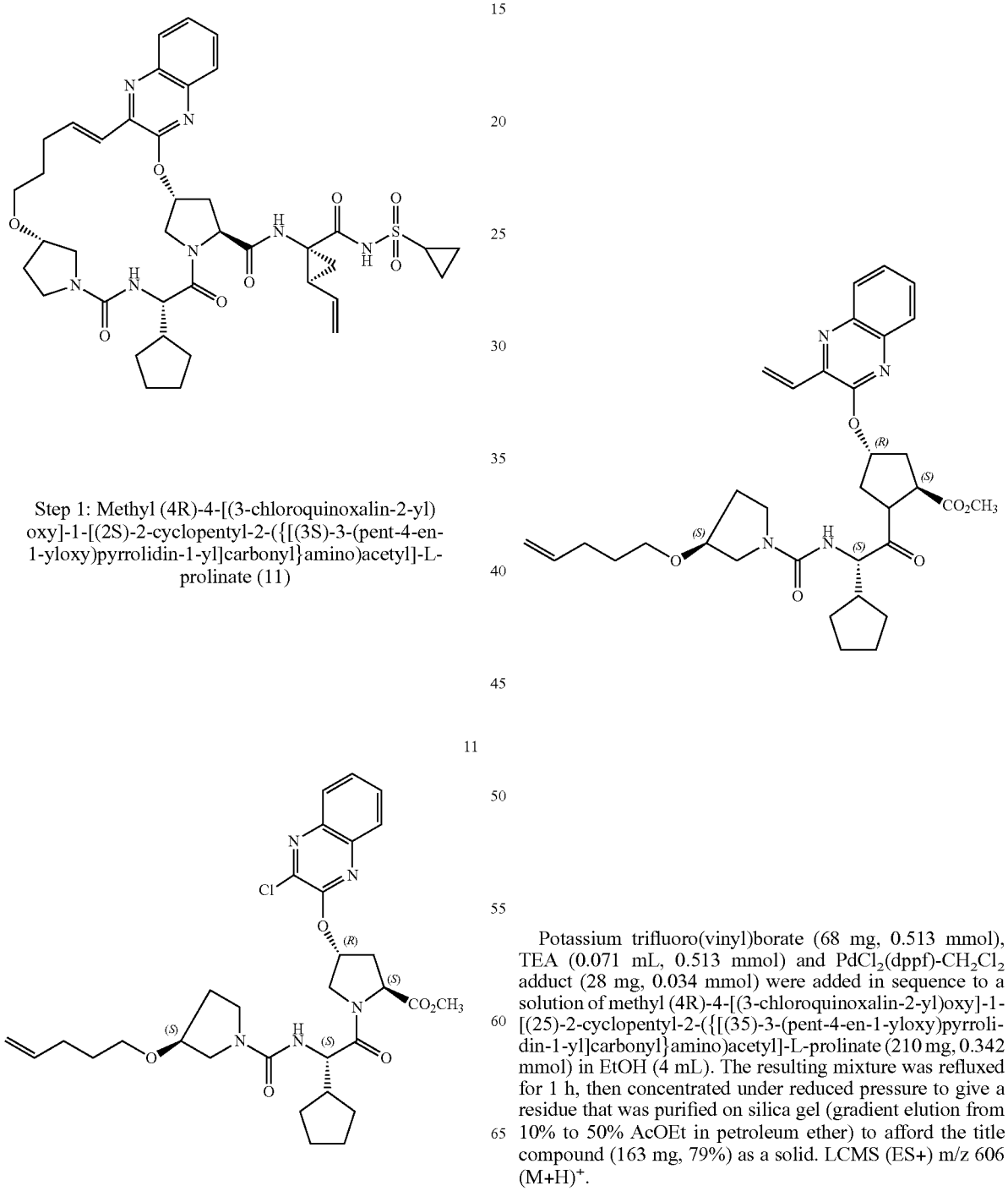

Potassium trifluoro(vinyl)borate (68 mg, 0.513 mmol), TEA (0.071 mL, 0.513 mmol) and PdCl$_2$(dppf)-CH$_2$Cl$_2$ adduct (28 mg, 0.034 mmol) were added in sequence to a solution of methyl (4R)-4-[(3-chloroquinoxalin-2-yl)oxy]-1-[(2S)-2-cyclopentyl-2-({[(3S)-3-(pent-4-en-1-yloxy)pyrrolidin-1-yl]carbonyl}amino)acetyl]-L-prolinate (210 mg, 0.342 mmol) in EtOH (4 mL). The resulting mixture was refluxed for 1 h, then concentrated under reduced pressure to give a residue that was purified on silica gel (gradient elution from 10% to 50% AcOEt in petroleum ether) to afford the title compound (163 mg, 79%) as a solid. LCMS (ES+) m/z 606 (M+H)+.

Step 3: (2R,4S,7S,13S,18E)-7-Cyclopentyl-((1R, 2S)-1-{[(cyclopropylsulfonyl)amino]carbonyl}-2-vinylcyclopropyl)-6,9-dioxo-3,4,6,7,8,9,12,13,16,17-decahydro-2H,11H,15H-2,5:10,13-dimethano[1,14,5,7,10]dioxatriazacyclohenicosino[15,16-b]quinoxaline-4-carboxamide (EXAMPLE 2)

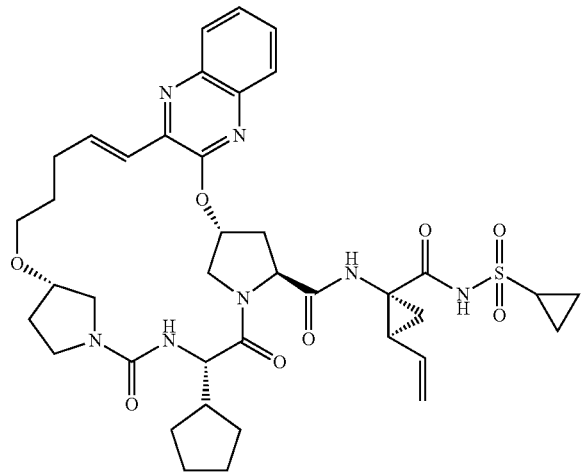

Subjecting methyl (41R)-1-[(2S)-2-cyclopentyl-2-({[(3S)-3-(pent-4-en-1-yloxy)pyrrolidin-1-yl]carbonyl}amino)acetyl]-4-[(3-vinylquinoxalin-2-yl)oxy]-L-prolinate (110 mg, 0.181 mmol) to the procedures described in EXAMPLE 1, steps 2, 4 and 5, afforded the title compound (22 mg, 15%) as a solid. $^1$H NMR (DMSO-$d_6$) δ 10.45 (s, 1H), 9.06 (s, 1H), 7.95 (d, J=7.6 Hz, 1H), 7.80 (d, J=7.8 Hz, 1H), 7.69 (t, J=7.8 Hz, 1H), 7.62 (t, J=7.6 Hz, 1H), 7.08-7.00 (m, 1H), 6.63 (d, J=15.7 Hz, 1H), 6.12 (d, J=8.3 Hz, 1H), 6.06-6.02 (m, 1H), 5.68-5.55 (m, 1H), 5.24 (d, J=16.7 Hz, 1H), 5.11 (d, J=11.4 Hz, 1H), 4.99 (d, J=11.6 Hz, 1H), 4.35 (dd, J=10.6 Hz, J=6.8 Hz, 1H), 4.23 (t, J=9.6 Hz, 1H), 3.92-3.85 (m, 1H), 3.45-3.39 (m, 2H), 3.33-3.27 (m, 1H), 3.25-3.18 (m, 1H), 2.99-2.92 (m, 2H), (1H under DMSO), 2.45-2.37 (m, 2H), 2.35-2.27 (m, 2H), 2.25-2.10 (m, 2H), 2.03-1.90 (m, 2H), 1.88-1.41 (m, 10H), 1.32-1.27 (m, 1H), 1.22-1.12 (m, 2H), 1.11-1.01 (m, 4H); LCMS (ES+) m/z 776 (M+H)$^+$.

The following EXAMPLES were prepared according to the appropriate procedures described in EXAMPLE 1 and EXAMPLE 2 using the appropriate Intermediates A, B and C.

| Ex. | Structure | Name | LRMS (M + H)$^+$ | Intermediates and Procedure | Cell based HCV Replication Assay-IC$_{50}$ (nM) |
|---|---|---|---|---|---|
| 3 | 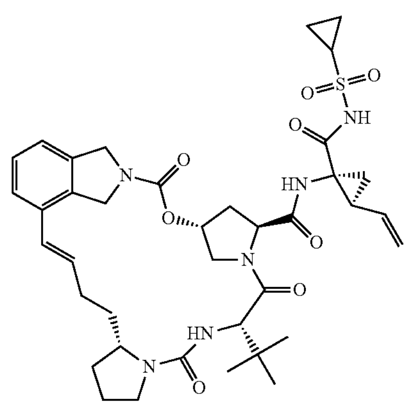 [SMILES: C=C[C@@H]1C[C@]1(NC(=O)[C@@H]1C[C@@H]2CN1C(=O)[C@H](C(C)(C)C)NC(=O)N1CCC[C@@H]1CC/C=C/c1cccc3c1CN(C3)C(=O)O2)C(=O)NS(=O)(=O)C1CC1] | (1R,12E,16S,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10,12-tetraene-26-carboxamide | | A1, B2, C2 EXAMPLE 1, Steps 1, 2, 4 and 5. Separate diastereomers. | 16 |
| 4 | 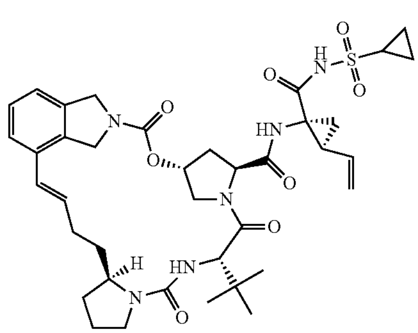 [SMILES: C=C[C@@H]1C[C@]1(NC(=O)[C@@H]1C[C@@H]2CN1C(=O)[C@H](C(C)(C)C)NC(=O)N1CCC[C@H]1CC/C=C/c1cccc3c1CN(C3)C(=O)O2)C(=O)NS(=O)(=O)C1CC1] | (1R,12E,16R,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10,12-tetraene-26-carboxamide | 751 | A1, B2, C2 EXAMPLE 1, Steps 1, 2, 4 and 5. Separate diastereomers. | 260 |

-continued

| Ex. | Structure | Name | LRMS (M + H)+ | Intermediates and Procedure | Cell based HCV Replication Assay-IC$_{50}$ (nM) |
|---|---|---|---|---|---|
| 5 | 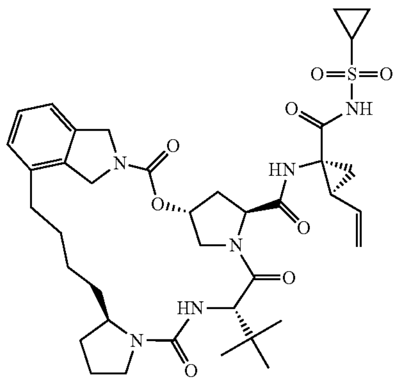 [SMILES: C=C[C@@H]1C[C@]1(NC(=O)[C@@H]1C[C@@H]2CN1C(=O)[C@H](C(C)(C)C)NC(=O)N1CCC[C@H]1CCCCc1cccc3c1CN(C3)C(=O)O2)C(=O)NS(=O)(=O)C1CC1] | (1R,16R,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10-triene-26-carboxamide | | A1, B2, C2 EXAMPLE 1. Separate diastereomers. | 170 |
| 6 | 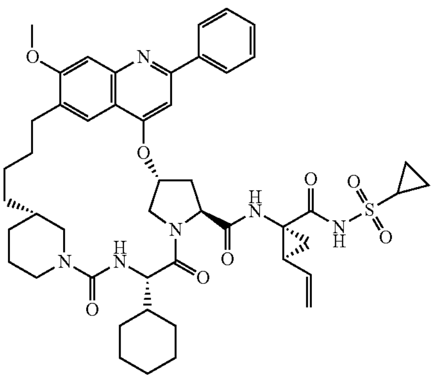 [SMILES: C=C[C@@H]1C[C@]1(NC(=O)[C@@H]1C[C@@H]2CN1C(=O)[C@H](C1CCCCC1)NC(=O)N1CCC[C@H](CCCCc3cc4c(cc(-c5ccccc5)nc4cc3OC)O2)C1)C(=O)NS(=O)(=O)C1CC1] | (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-25-phenyl-2-oxa-6,9,11,24-tetraazapentacyclo[18.6.2.1$^{3,6}$.1$^{11,15}$.0$^{23,27}$]triaconta-1(27),20,22,23,25,27-hexaene-5-carboxamide | 882 | A1, B5, C1 EXAMPLE 1. Separate diastereomers. | 24 |
| 7 | 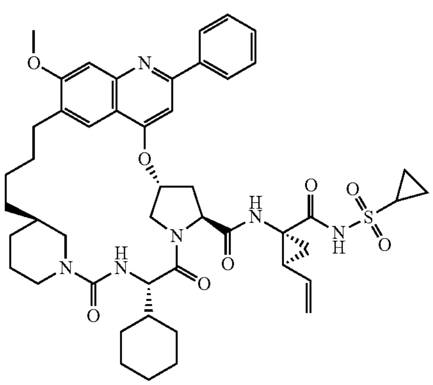 [SMILES: C=C[C@@H]1C[C@]1(NC(=O)[C@@H]1C[C@@H]2CN1C(=O)[C@H](C1CCCCC1)NC(=O)N1CCC[C@@H](CCCCc3cc4c(cc(-c5ccccc5)nc4cc3OC)O2)C1)C(=O)NS(=O)(=O)C1CC1] | (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-25-phenyl-2-oxa-6,9,11,24-tetraazapentacyclo[18.6.2.1$^{3,6}$.1$^{11,15}$.0$^{23,27}$]triaconta-1(27),20,22,23,25,27-hexaene-5-carboxamide | 882 | A1, B5, C1 EXAMPLE 1. Separate diastereomers. | 8 |
| 8 | 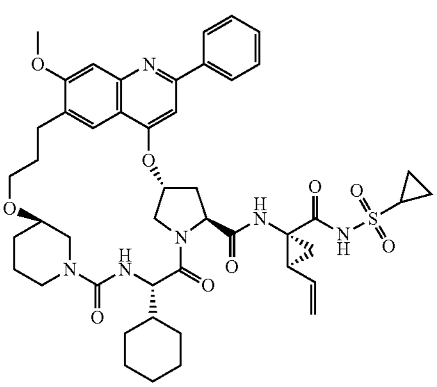 [SMILES: C=C[C@@H]1C[C@]1(NC(=O)[C@@H]1C[C@@H]2CN1C(=O)[C@H](C1CCCCC1)NC(=O)N1CCC[C@H](C1)OCCCc1cc3c(cc(-c4ccccc4)nc3cc1OC)O2)C(=O)NS(=O)(=O)C1CC1] | (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-25-phenyl-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide | 884 | A1, B1, C1 EXAMPLE 1. Separate diastereomers. | 5 |

-continued

| Ex. | Structure | Name | LRMS (M + H)+ | Intermediates and Procedure | Cell based HCV Replication Assay-IC$_{50}$ (nM) |
|---|---|---|---|---|---|
| 9 | 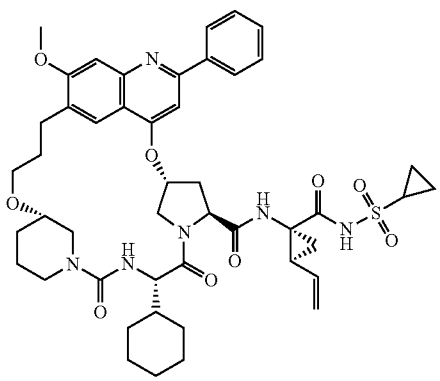 [SMILES: C=C[C@@H]1C[C@]1(NC(=O)[C@@H]1C[C@@H]2CN1C(=O)[C@H](C1CCCCC1)NC(=O)N1CCC[C@@H](C1)OCCCc1cc3c(cc(-c4ccccc4)nc3cc1OC)O2)C(=O)NS(=O)(=O)C1CC1] | (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-25-phenyl-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide | 884 | A1, B1, C1 EXAMPLE 1. Separate diastereomers. | 7 |
| 10 | 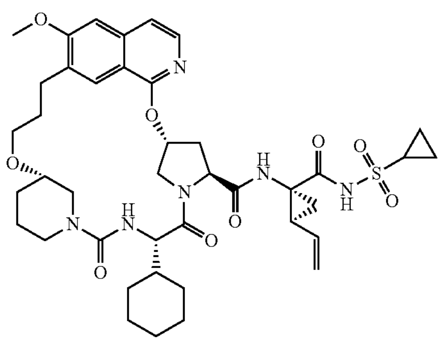 [SMILES: C=C[C@@H]1C[C@]1(NC(=O)[C@@H]1C[C@@H]2CN1C(=O)[C@H](C1CCCCC1)NC(=O)N1CCC[C@@H](C1)OCCCc1cc3c(nccc3cc1OC)O2)C(=O)NS(=O)(=O)C1CC1] | (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-2,16-dioxa-6,9,11,26-tetraazapentacyclo[18.6.2.1$^{3,6}$.1$^{11,15}$.0$^{23,27}$]triaconta-1(26),20,22,24,27-pentaene-5-carboxamide | 807 | A1, B1, C3 EXAMPLE 1. Separate diastereomers. | 7 |
| 11 | 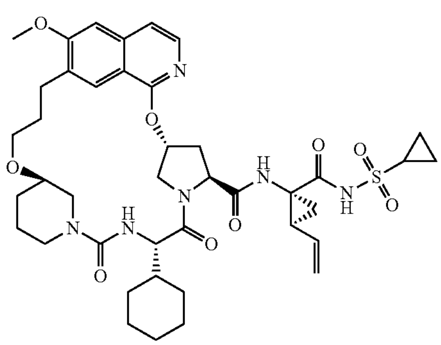 [SMILES: C=C[C@@H]1C[C@]1(NC(=O)[C@@H]1C[C@@H]2CN1C(=O)[C@H](C1CCCCC1)NC(=O)N1CCC[C@H](C1)OCCCc1cc3c(nccc3cc1OC)O2)C(=O)NS(=O)(=O)C1CC1] | (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-2,16-dioxa-6,9,11,26-tetraazapentacyclo[18.6.2.1$^{3,6}$.1$^{11,15}$.0$^{23,27}$]triaconta-1(26),20,22,24,27-pentaene-5-carboxamide | 807 | A1, B1, C3 EXAMPLE 1. Separate diastereomers. | 6 |
| 12 | 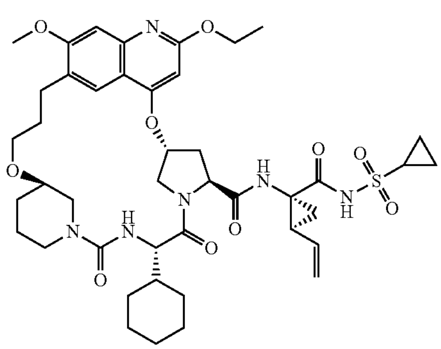 [SMILES: C=C[C@@H]1C[C@]1(NC(=O)[C@@H]1C[C@@H]2CN1C(=O)[C@H](C1CCCCC1)NC(=O)N1CCC[C@H](C1)OCCCc1cc3c(cc(OCC)nc3cc1OC)O2)C(=O)NS(=O)(=O)C1CC1] | (3R,5S,8S,15R)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide | 852 | A1, B1, C4 EXAMPLE 1. Separate diastereomers. | 4 |

| Ex. | Structure | Name | LRMS (M + H)+ | Intermediates and Procedure | Cell based HCV Replication Assay-IC$_{50}$ (nM) |
|---|---|---|---|---|---|
| 13 | 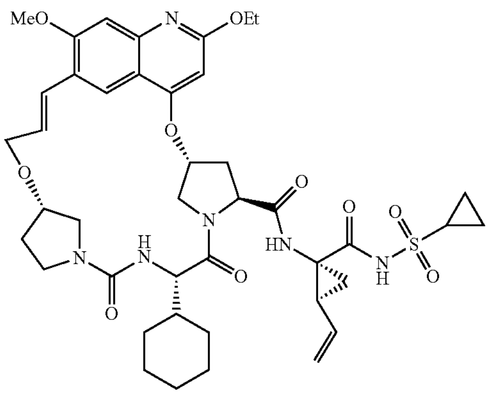 [SMILES: C=C[C@@H]1C[C@]1(NC(=O)[C@@H]1C[C@@H]2CN1C(=O)[C@H](C1CCCCC1)NC(=O)N1CC[C@@H](C1)OC/C=C/c1cc3c(cc(OCC)nc3cc1OC)O2)C(=O)NS(=O)(=O)C1CC1] | (3R,5S,8S,14S,17E)-8-cyclohexyl-N-((1R,2S)-1-{[(cyclopropylsulfonyl)amino]carbonyl}-2-vinylcyclopropyl)-24-ethoxy-20-methoxy-7,10-dioxo-2,15-dioxa-6,9,11,23-tetraazapentacyclo[17.6.2.1$^{3,6}$.1$^{11,14}$.0$^{22,26}$]nonacosa-1(25),17,19,21,23,26-hexaene-5-carboxamide | 835.3 | A1, B3, C4 EXAMPLE 1, Steps 1, 2, 4 and 5. | 9 |
| 14 | 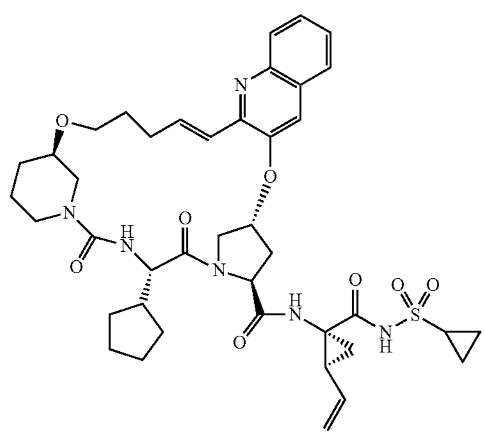 | (4S,7S,9R,21E,27R)-4-cyclopentyl-N-((1R,2S)-1-{[(cyclopropylsulfonyl)amino]carbonyl}-2-vinylcyclopropyl)-2,5-dioxo-10,26-dioxa-1,3,6,19-tetraazapentacyclo[25.3.1.1$^{6,9}$.0$^{11,20}$.0$^{13,18}$]dotriaconta-11(20),12,13,15,17,18,21-heptaene-7-carboxamide | 789 | A1, B6, C7 EXAMPLE 2 Steps 1-2 EXAMPLE 1 Steps 2,4, 5 | |
| 15 | 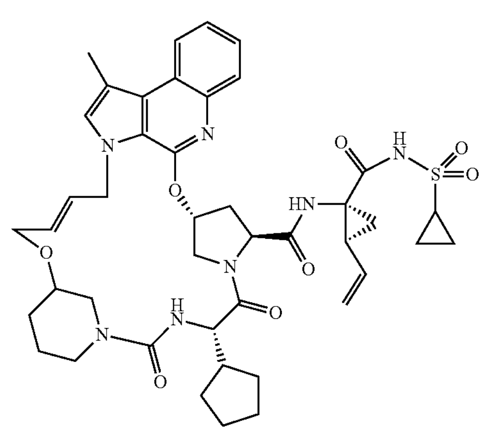 [SMILES: C=C[C@@H]1C[C@]1(NC(=O)[C@@H]1C[C@@H]2CN1C(=O)[C@H](C1CCCC1)NC(=O)N1CCCC(C1)OC/C=C/Cn1cc(C)c3c4ccccc4nc(c31)O2)C(=O)NS(=O)(=O)C1CC1] | (3S,5S,8S,18E)-8-cyclopentyl-N-((1R,2S)-1-{[(cyclopropylsulfonyl)amino]carbonyl}-2-vinylcyclopropyl)-23-methyl-7,10-dioxo-2,16-dioxa-6,9,11,21,31-pentaazahexacyclo[19.10.1.1$^{3,6}$.1$^{11,15}$.0$^{24,32}$.0$^{25,30}$]tetratriaconta-1(31),18,22,24(32),25,27,29-heptaene-5-carboxamide | 828 | A1, B7, C9 EXAMPLE 1, Steps 1, 2, 4 and 5. | 5 |

| Ex. | Structure | Name | LRMS (M + H)+ | Intermediates and Procedure | Cell based HCV Replication Assay-IC$_{50}$ (nM) |
|---|---|---|---|---|---|
| 16 | 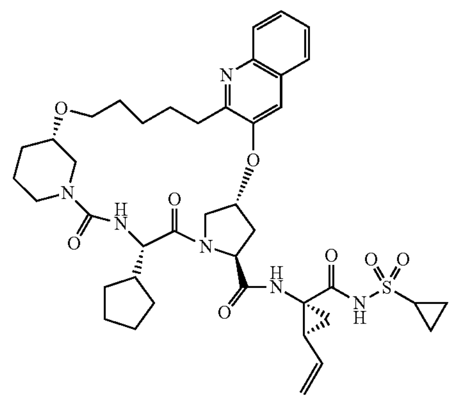 | (4S,7S,9R,27S)-4-cyclopentyl-N-((1R,2S)-1-{[(cyclopropylsulfonyl)amino]carbonyl}-2-vinylcyclopropyl)-2,5-dioxo-10,26-dioxa-1,3,6,19-tetraazapentacyclo[25.3.1.1$^{6,9}$.0$^{11,20}$.0$^{13,18}$]dotriaconta-11(20),12,13,15,17,18-hexaene-7-carboxamide | 791 | A1, B6, C7 EXAMPLE 2 Steps 1-2 EXAMPLE 1 Steps 2-5 | |
| 17 | 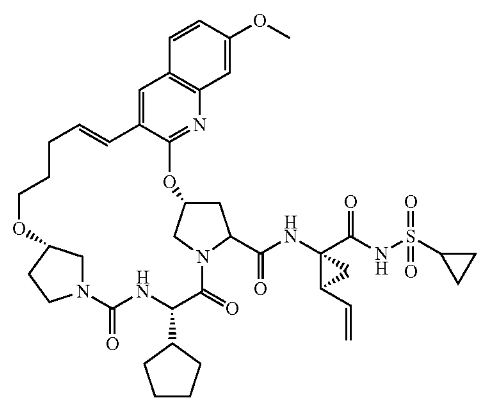 [SMILES: C=C[C@@H]1C[C@]1(NC(=O)C1C[C@@H]2CN1C(=O)[C@H](C1CCCC1)NC(=O)N1CC[C@@H](C1)OCCC/C=C/c1cc3ccc(OC)cc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 805.5 | A1, B8, C6 EXAMPLE 1, Steps 1, 2, 4 and 5. | 4 |
| 18 | 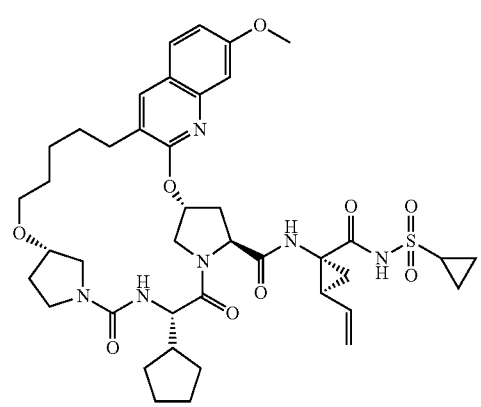 [SMILES: C=C[C@@H]1C[C@]1(NC(=O)[C@@H]1C[C@@H]2CN1C(=O)[C@H](C1CCCC1)NC(=O)N1CC[C@@H](C1)OCCCCCc1cc3ccc(OC)cc3nc1O2)C(=O)NS(=O)(=O)C1CC1] | (1R,19S,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 807.4 | A1, B8, C6 EXAMPLE 1. | 7 |

| Ex. | Structure | Name | LRMS (M + H)+ | Intermediates and Procedure | Cell based HCV Replication Assay-IC$_{50}$ (nM) |
|---|---|---|---|---|---|
| 19 | 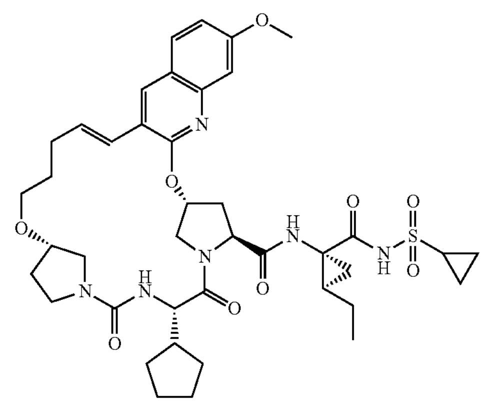 [SMILES: CC[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ccc(OC)cc3nc1O2)C(=O)NS(=O)(=O)C1CC1] | (1R,13E,19S,25S,28S)-25-cyclopentyl-N-((1R,2R)-1-{[(cyclopropylsulfonyl)amino]carbonyl}-2-ethylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 807.5 | A3, B8, C6 EXAMPLE 1, Steps 1, 2, 4 and 5. | 4 |
| 20 | 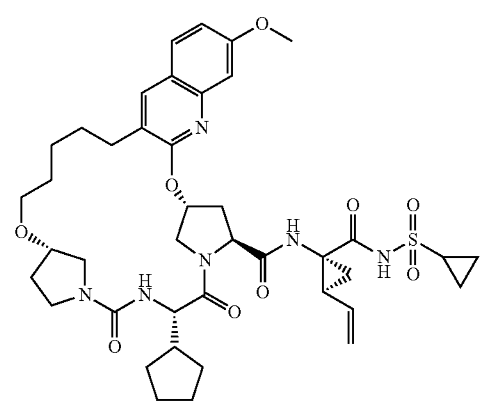 [SMILES: C=C[C@@H]1C[C@]1(NC(=O)[C@@H]1C[C@@H]2CN1C(=O)[C@H](C1CCCC1)NC(=O)N1CC[C@@H](C1)OCCCCCc1cc3ccc(OC)cc3nc1O2)C(=O)NS(=O)(=O)C1CC1] | (1R,19S,25S,28S)-25-cyclopentyl-N-((1R,2R)-1-{[(cyclopropylsulfonyl)amino]carbonyl}-2-ethylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 809.4 | A3, B8, C6 EXAMPLE 1. | 15 |
| 21 | 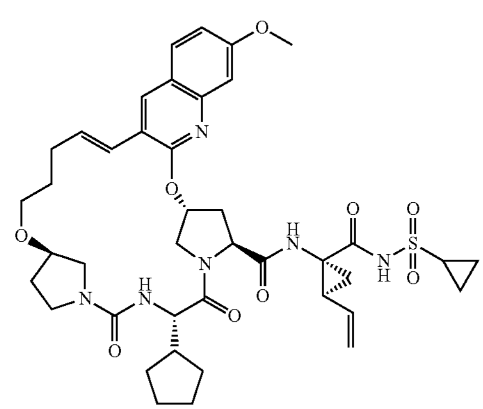 [SMILES: C=C[C@@H]1C[C@]1(NC(=O)[C@@H]1C[C@@H]2CN1C(=O)[C@H](C1CCCC1)NC(=O)N1CC[C@H](C1)OCCC/C=C/c1cc3ccc(OC)cc3nc1O2)C(=O)NS(=O)(=O)C1CC1] | (1R,13E,19S,25S,28S)-25-cyclopentyl-N-((1R,2R)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 805.4 | A1, B9, C6 EXAMPLE 1, Steps 1, 2, 4 and 5. | 20 |

-continued

| Ex. | Structure | Name | LRMS (M + H)+ | Intermediates and Procedure | Cell based HCV Replication Assay-IC$_{50}$ (nM) |
|---|---|---|---|---|---|
| 22 | 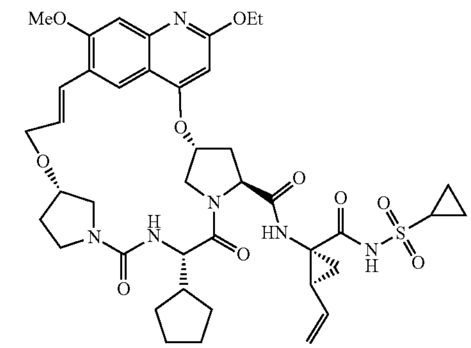 [SMILES: C=C[C@@H]1C[C@]1(NC(=O)[C@@H]1C[C@@H]2CN1C(=O)[C@H](C1CCCC1)NC(=O)N1CC[C@@H](C1)OC/C=C/c1cc3c(cc(OCC)nc3cc1OC)O2)C(=O)NS(=O)(=O)C1CC1] | (3R,5S,8S,14S,17E)-8-cyclopentyl-N-((1R,2S)-1-{[(cyclopropylsulfonyl)amino]carbonyl}-2-vinylcyclopropyl)-24-ethoxy-20-methoxy-7,10-dioxo-2,15-dioxa-6,9,11,23-tetraazapentacyclo[17.6.2.1$^{3,6}$.1$^{11,14}$.0$^{22,26}$]nonacosa-1(25),17,19,21,23,26-hexaene-5-carboxamide | 821.4 | A1, B10, C4 EXAMPLE 1, Steps 1, 2, 4 and 5. | 11 |
| 23 | 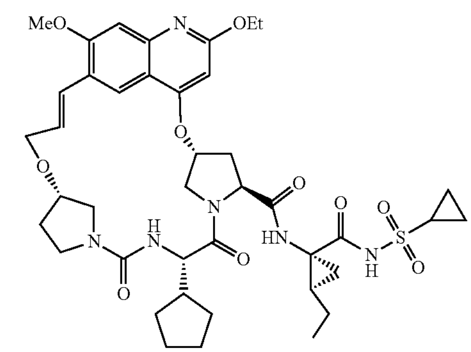 | (3R,5S,8S,14S,17E)-8-cyclopentyl-N-((1R,2R)-1-{[(cyclopropylsulfonyl)amino]carbonyl}-2-ethylcyclopropyl)-24-ethoxy-20-methoxy-7,10-dioxo-2,15-dioxa-6,9,11,23-tetraazapentacyclo[17.6.2.1$^{3,6}$.1$^{11,14}$.0$^{22,26}$]nonacosa-1(25),17,19,21,23,26-hexaene-5-carboxamide | 823.2 | A3, B10, C4 EXAMPLE 1, Steps 1, 2, 4 and 5. | 7 |
| 24 | 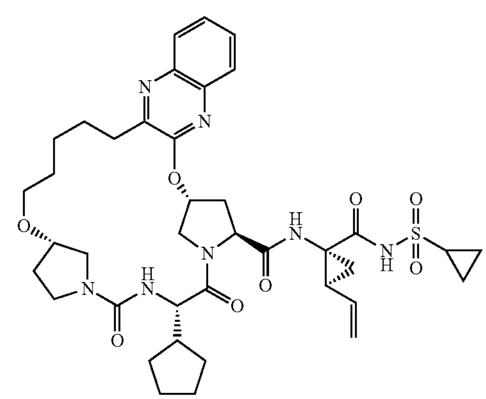 [SMILES: C=C[C@@H]1C[C@]1(NC(=O)[C@@H]1C[C@@H]2CN1C(=O)[C@H](C1CCCC1)NC(=O)N1CC[C@@H](C1)OCCCCCc1nc3ccccc3nc1O2)C(=O)NS(=O)(=O)C1CC1] | (2R,4S,7S,13S)-7-cyclopentyl-N-((1R,2S)-1-{[(cyclopropylsulfonyl)amino]carbonyl}-2-vinylcyclopropyl)-6,9-dioxo-3,4,6,7,8,9,12,13,16,17,18,19-dodecahydro-2H,11H,15H-2,5:10,13-dimethano[1,14,5,7,10]dioxatriazacyclohenicosino[15,16-b]quinoxaline-4-carboxamide | 778 | A1, B8, C10 EXAMPLE 2 Steps 1-2 EXAMPLE 1 Steps 2-5 | |
| 25 | 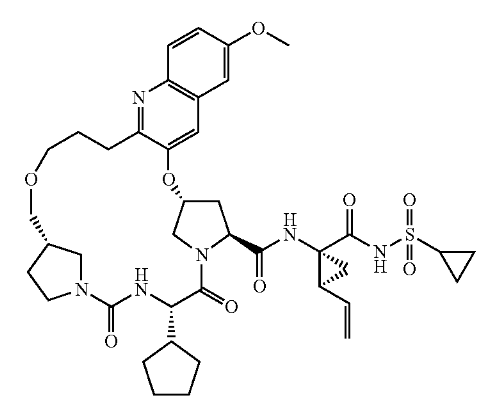 [SMILES: C=C[C@@H]1C[C@]1(NC(=O)[C@@H]1C[C@@H]2CN1C(=O)[C@H](C1CCCC1)NC(=O)N1CC[C@H](COCCCc3nc4ccc(OC)cc4cc3O2)C1)C(=O)NS(=O)(=O)C1CC1] | (1R,18S,24S,27S)-24-cyclopentyl-N-((1R,2R)-1-{[(cyclopropylsulfonyl)amino]carbonyl}-2-vinylcyclopropyl)-7-methoxy-22,25-dioxo-2,16-dioxa-11,21,23,26-tetraazapentacyclo[24.2.1.1$^{18,21}$.0$^{3,12}$.0$^{5,10}$]triaconta-3(12),4,5,7,9,10-hexaene-27-carboxamide | 793 | A1, B14, C8 EXAMPLE 2 Steps 1-2 EXAMPLE 1 Steps 2-5 | 7 |

-continued

| Ex. | Structure | Name | LRMS (M + H)+ | Intermediates and Procedure | Cell based HCV Replication Assay-IC50 (nM) |
|---|---|---|---|---|---|
| 27 | 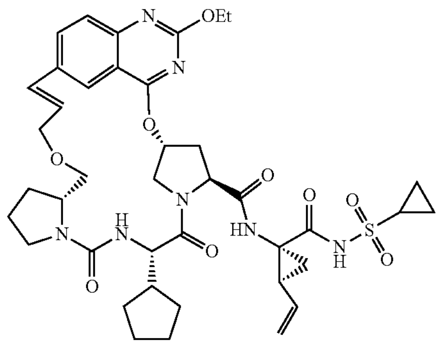 [SMILES: C=C[C@@H]1C[C@]1(NC(=O)[C@@H]1C[C@@H]2CN1C(=O)[C@H](C1CCCC1)NC(=O)N1CCC[C@@H]1COC/C=C/c1ccc3nc(OCC)nc(c3c1)O2)C(=O)NS(=O)(=O)C1CC1] | (2R,4S,7S,13S)-7-cyclopentyl-N-((1R,2S)-1-{[(cyclopropylsulfonyl)amino]carbonyl}-2-vinylcyclopropyl)-23-methoxy-6,9-dioxo-3,4,6,7,8,9,11,12,13,14,16,17,18,19-tetradecahydro-2H-2,5:10,13-dimethano[1,15,5,8,10]dioxatriazacyclohenicosino[20,21-b]quinoline-4-carboxamide | 806 | A1, B12, C11 EXAMPLE 1 Steps 1, 2, 4, 5 | |
| 28 | 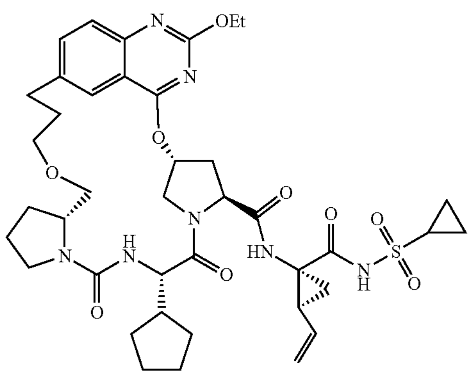 [SMILES: C=C[C@@H]1C[C@]1(NC(=O)[C@@H]1C[C@@H]2CN1C(=O)[C@H](C1CCCC1)NC(=O)N1CCC[C@@H]1COCCCc1ccc3nc(OCC)nc(c3c1)O2)C(=O)NS(=O)(=O)C1CC1] | (6R,8S,11S,17aR)-11-cyclopentyl-N-((1R,2S)-1-{[(cyclopropylsulfonyl)amino]carbonyl}-2-vinylcyclopropyl)-3-ethoxy-10,13-dioxo-7,8,10,11,12,13,16,17,17a,18,20,21-dodecahydro-6H,15H-1,22-(ethanediylidene)-6,9-methanopyrimido[4,5-n]pyrrolo[2,1-c][1,13,4,6,9]dioxatriazacyclononadecine-8-carboxamide | 808 | A1, B12, C11 EXAMPLE 1. | 6 |
| 29 | 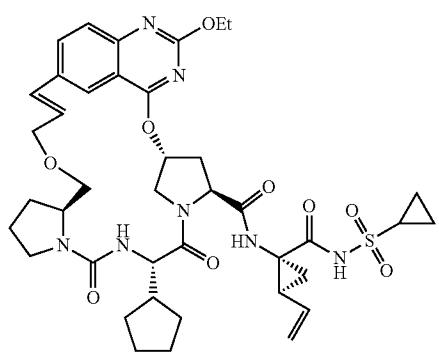 [SMILES: C=C[C@@H]1C[C@]1(NC(=O)[C@@H]1C[C@@H]2CN1C(=O)[C@H](C1CCCC1)NC(=O)N1CCC[C@H]1COC/C=C/c1ccc3nc(OCC)nc(c3c1)O2)C(=O)NS(=O)(=O)C1CC1] | (6R,8S,11S,17aS,20E)-11-cyclopentyl-N-((1R,2S)-1-{[(cyclopropylsulfonyl)amino]carbonyl}-2-vinylcyclopropyl)-3-ethoxy-10,13-dioxo-7,8,10,11,12,13,16,17,17a,18-decahydro-6H,15H-1,22-(ethanediylidene)-6,9-methanopyrimido[4,5-n]pyrrolo[2,1-c][1,13,4,6,9]dioxatriazacyclononadecine-8-carboxamide | 806 | A1, B13, C11 EXAMPLE 1 Steps 1, 2, 4, 5 | |
| 30 | 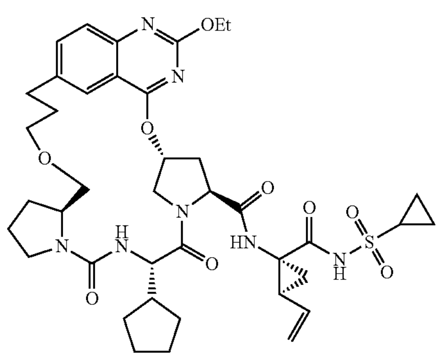 [SMILES: C=C[C@@H]1C[C@]1(NC(=O)[C@@H]1C[C@@H]2CN1C(=O)[C@H](C1CCCC1)NC(=O)N1CCC[C@H]1COCCCc1ccc3nc(OCC)nc(c3c1)O2)C(=O)NS(=O)(=O)C1CC1] | (6R,8S,11S,17aS)-11-cyclopentyl-N-((1R,2S)-1-{[(cyclopropylsulfonyl)amino]carbonyl}-2-vinylcyclopropyl)-3-ethoxy-10,13-dioxo-7,8,10,11,12,13,16,17,17a,18,20,21-dodecahydro-6H,15H-1,22-(ethanediylidene)-6,9-methanopyrimido[4,5-n]pyrrolo[2,1-c][1,13,4,6,9]dioxatriazacyclononadecine-8-carboxamide | 808 | A1, B13, C11 EXAMPLE 1. | |

-continued

| Ex. | Structure | Name | LRMS (M + H)+ | Intermediates and Procedure | Cell based HCV Replication Assay-IC$_{50}$ (nM) |
|---|---|---|---|---|---|
| 31 | 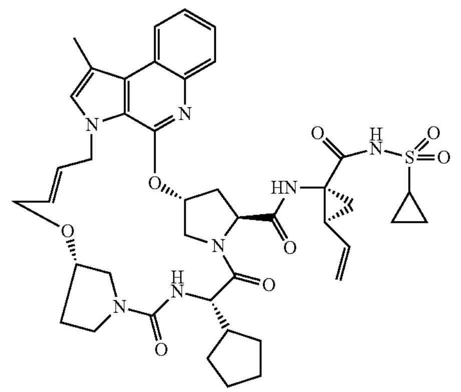 [SMILES: C=C[C@@H]1C[C@]1(NC(=O)[C@@H]1C[C@@H]2CN1C(=O)[C@H](C1CCCC1)NC(=O)N1CC[C@@H](C1)OC/C=C/Cn1cc(C)c3c4ccccc4nc(c31)O2)C(=O)NS(=O)(=O)C1CC1] | (4E,8S,14S,17S,19R)-14-cyclopentyl-N-((1R,2S)-1-{[(cyclopropylsulfonyl)amino]carbonyl}-2-vinylcyclopropyl)-1-methyl-12,15-dioxo-3,6,9,10,12,13,14,15,18,19-decahydro-8H,17H-8,11:16,19-dimethano-7,20-dioxa-2a,11,13,16,21-pentaazabenzo[g]cyclohenicosa[1,2,3-cd]indene-17-carboxamide | 814 | A1, B10, C8 EXAMPLE 1. Steps 1, 2, 4, 5. | 7 |
| 32 | 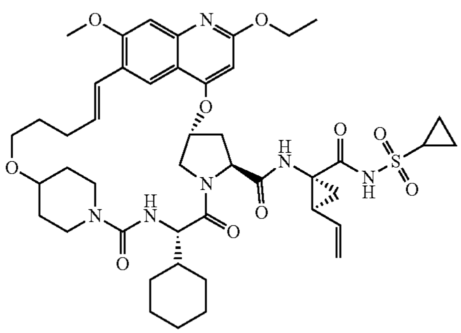 [SMILES: C=C[C@@H]1C[C@]1(NC(=O)[C@@H]1C[C@@H]2CN1C(=O)[C@H](C1CCCCC1)NC(=O)N1CCC(CC1)OCCC/C=C/c1cc3c(cc(OCC)nc3cc1OC)O2)C(=O)NS(=O)(=O)C1CC1] | (3R,5S,8S,19E)-8-cyclohexyl-N-((1R,2R)-1-{[(cyclopropylsulfonyl)amino]carbonyl}-2-vinylcyclopropyl)-26-ethoxy-22-methoxy-7,10-dioxo-2,15-dioxa-6,9,11,25-tetraazapentacyclo[19.6.2.2$^{11,14}$.1$^{3,6}$.0$^{24,28}$]dotriaconta-1(27),19,21,23,25,28-hexaene-5-carboxamide | 878.3 | A1, B15, C4 EXAMPLE 1. Steps 1, 2, 4, 5. | 10 |
| 33 | 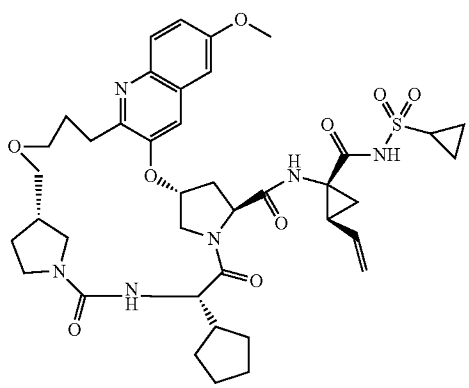 [SMILES: C=C[C@@H]1C[C@]1(NC(=O)[C@@H]1C[C@@H]2CN1C(=O)[C@H](C1CCCC1)CNC(=O)N1CC[C@H](COCCCc3nc4ccc(OC)cc4cc3O2)C1)C(=O)NS(=O)(=O)C1CC1] | (1R,18S,24S,27S)-24-cyclopentyl-N-((1R,2R)-1-{[(cyclopropylsulfonyl)amino]carbonyl}-2-vinylcyclopropyl)-7-methoxy-22,25-dioxo-2,16-dioxa-11,21,23,26-tetraazapentacyclo[24.2.1.1$^{18,21}$.0$^{3,12}$.0$^{5,10}$]triaconta-3(12),4,5,7,9,10-hexaene-27-carboxamide | xx | A1, B8, C10 EXAMPLE 2 Steps 1-2 EXAMPLE 1 Steps 2, 4, 5. | >100 |
| 34 | 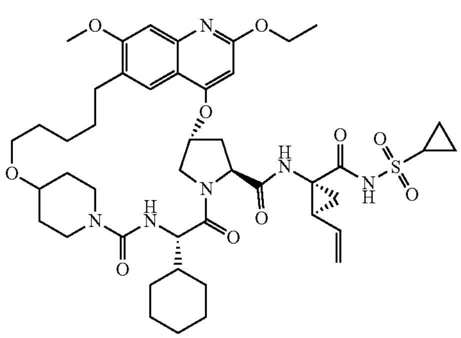 [SMILES: C=C[C@@H]1C[C@]1(NC(=O)[C@@H]1C[C@@H]2CN1C(=O)[C@H](C1CCCCC1)NC(=O)N1CCC(CC1)OCCCCCc1cc3c(cc(OCC)nc3cc1OC)O2)C(=O)NS(=O)(=O)C1CC1] | (3R,5S,8S)-8-cyclohexyl-N-((1R,2R)-1-{[(cyclopropylsulfonyl)amino]carbonyl}-2-vinylcyclopropyl)-26-ethoxy-22-methoxy-7,10-dioxo-2,15-dioxa-6,9,11,25-tetraazapentacyclo[19.6.2.2$^{11,14}$.1$^{3,6}$.0$^{24,28}$]dotriaconta-1(27),21,23,25,28-pentaene-5-carboxamide | 880.3 | EXAMPLE 45, starting with EXAMPLE 32. | 7 |

-continued

| Ex. | Structure | Name | LRMS (M + H)+ | Intermediates and Procedure | Cell based HCV Replication Assay-IC$_{50}$ (nM) |
|---|---|---|---|---|---|
| 35 | 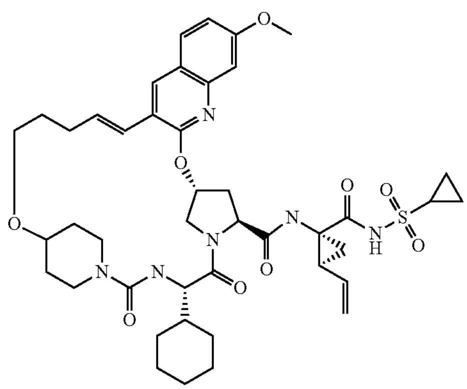 [SMILES: C=C[C@@H]1C[C@]1(NC(=O)[C@@H]1C[C@@H]2CN1C(=O)[C@H](C1CCCCC1)NC(=O)N1CCC(CC1)OCCCC/C=C/c1cc3ccc(OC)cc3nc1O2)C(=O)NS(=O)(=O)C1CC1] | (4S,7S,9R,21E)-4-cyclohexyl-N-((1R,2S)-1-{[(cyclopropylsulfonyl)amino]carbonyl}-2-vinylcyclopropyl)-15-methoxy-2,5-dioxo-10,26-dioxa-1,3,6,12-tetraazapentacyclo[25.2.2.1$^{6,9}$.0$^{11,20}$.0$^{13,18}$]dotriaconta-11(20),12,13,15,17,18,21-heptaene-7-carboxamide | 834.1 | A1, B15, C6 EXAMPLE 1. Steps 1, 2, 4, 5. | |
| 36 | 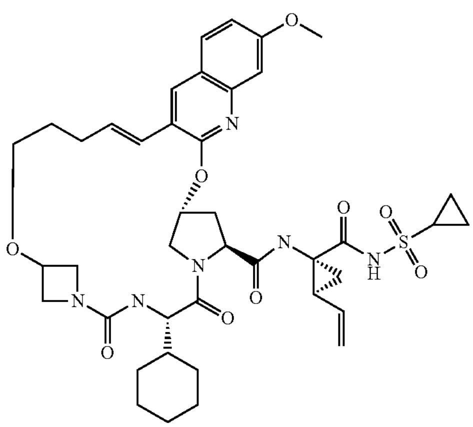 [SMILES: C=C[C@@H]1C[C@]1(NC(=O)[C@@H]1C[C@@H]2CN1C(=O)[C@H](C1CCCCC1)NC(=O)N1CC(C1)OCCCC/C=C/c1cc3ccc(OC)cc3nc1O2)C(=O)NS(=O)(=O)C1CC1] | (1R,13E,24S,27S)-24-cyclohexyl-N-((1R,2S)-1-{[(cyclopropylsulfonyl)amino]carbonyl}-2-vinylcyclopropyl)-7-methoxy-22,25-dioxo-2,18-dioxa-4,21,23,26-tetraazapentacyclo[24.2.1.1$^{19,21}$.0$^{3,12}$.0$^{5,10}$]triaconta-3(12),4,5,7,9,10,13-heptaene-28-carboxamide | 805.3 | A1, B16, C6 EXAMPLE 1. Steps 1, 2, 4, 5. | |
| 37 | 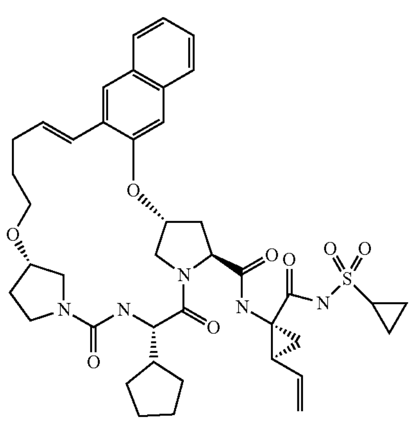 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ccccc3cc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10,13-heptaene-28-carboxamide | 774.0 | A1, B8, C12 EXAMPLE 1. Steps 1, 2, 4, 5. | 4 |

| Ex. | Structure | Name | LRMS (M + H)+ | Intermediates and Procedure | Cell based HCV Replication Assay-IC$_{50}$ (nM) |
|---|---|---|---|---|---|
| 38 | 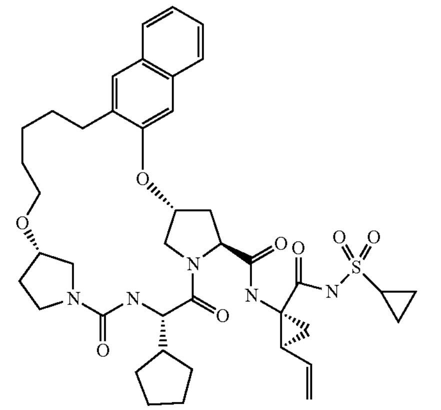 [SMILES: C=C[C@@H]1C[C@]1(NC(=O)[C@@H]1C[C@@H]2CN1C(=O)[C@H](C1CCCC1)NC(=O)N1CC[C@@H](C1)OCCCCCc1cc3ccccc3cc1O2)C(=O)NS(=O)(=O)C1CC1] | (1R,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10-hexaene-28-carboxamide | 776.0 | EXAMPLE 45, starting with EXAMPLE 37. | |
| 39 | 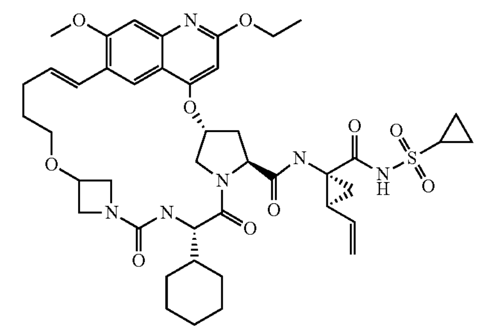 [SMILES: C=C[C@@H]1C[C@]1(NC(=O)[C@@H]1C[C@@H]2CN1C(=O)[C@H](C1CCCCC1)NC(=O)N1CC(C1)OCCC/C=C/c1cc3c(cc(OCC)nc3cc1OC)O2)C(=O)NS(=O)(=O)C1CC1] | (3R,5S,8S,18E)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,14-dioxa-6,9,11,24-tetraazapentacyclo[18.6.2.1$^{3,6}$.1$^{11,13}$.0$^{23,27}$]triaconta-1(26),18,20,22,24,27-hexaene-5-carboxamide | 850.3 | A1, B16, C4 EXAMPLE 1. Steps 1, 2, 4, 5. | 19 |
| 40 | 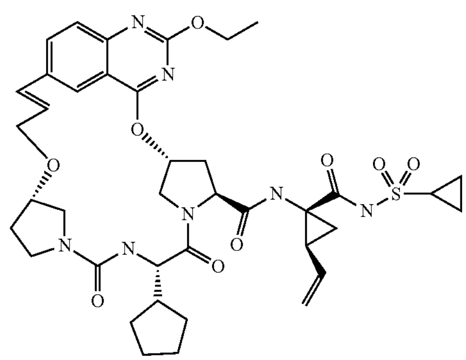 [SMILES: C=C[C@@H]1C[C@]1(NC(=O)[C@@H]1C[C@@H]2CN1C(=O)[C@H](C1CCCC1)NC(=O)N1CC[C@@H](C1)OC/C=C/c1ccc3nc(OCC)nc(c3c1)O2)C(=O)NS(=O)(=O)C1CC1] | (3R,5S,8S,14S)-8-cyclopentyl-N-((1R,2S)-1-{[(cyclopropylsulfonyl)amino]carbonyl}-2-vinylcyclopropyl)-24-ethoxy-7,10-dioxo-2,15-dioxa-6,9,11,23,25-pentaazapentacyclo[17.6.2.1$^{3,6}$.1$^{11,14}$.0$^{22,26}$]nonacosa-1(25),17,19,21,23,26-hexaene-5-carboxamide | xx | A1, B10, C11 EXAMPLE 2 Steps 1-2 EXAMPLE 1 Steps 2, 4, 5. | |

-continued

| Ex. | Structure | Name | LRMS (M + H)+ | Intermediates and Procedure | Cell based HCV Replication Assay-IC$_{50}$ (nM) |
|---|---|---|---|---|---|
| 41 | 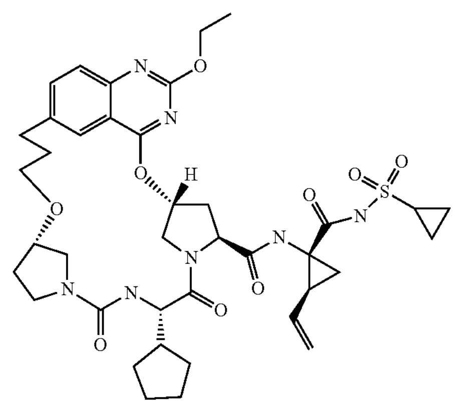 [SMILES: C=C[C@@H]1C[C@]1(NC(=O)[C@@H]1C[C@@H]2CN1C(=O)[C@H](C1CCCC1)NC(=O)N1CC[C@@H](C1)OCCCc1ccc3nc(OCC)nc(c3c1)O2)C(=O)NS(=O)(=O)C1CC1] | (3R,5S,8S,14S)-8-cyclopentyl-N-((1R,2S)-1-{[(cyclopropylsulfonyl)amino]carbonyl}-2-vinylcyclopropyl)-24-ethoxy-7,10-dioxo-2,15-dioxa-6,9,11,23,25-pentaazapentacyclo[17.6.2.1$^{3,6}$.1$^{11,14}$.0$^{22,26}$]nonacosa-1(25),19,21,23,26-pentaene-5-carboxamide | xx | A1, B10, C11 EXAMPLE 2 Steps 1-2 EXAMPLE 1 Steps 2-5. | 94 |
| 42 | 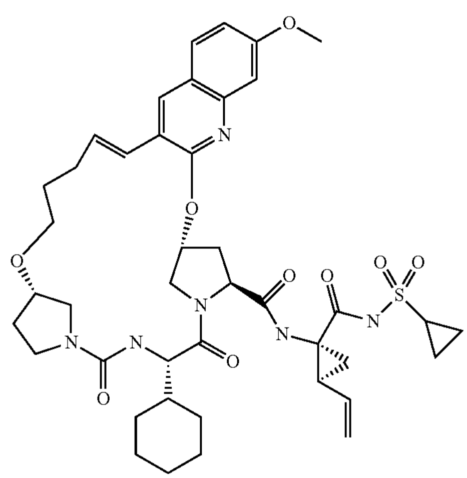 | (1R,13E,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 819.0 | A1, B17, C6 EXAMPLE 1, Steps 1, 2, 4, 5. | 3 |
| 43 | 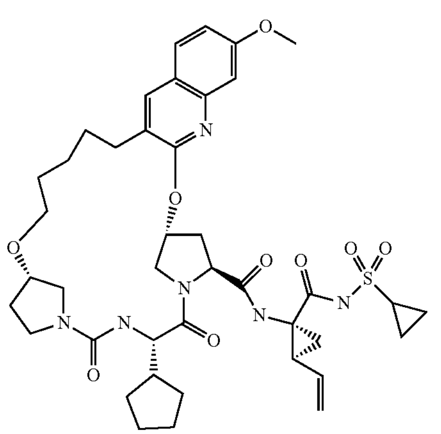 | (1R,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 821.0 | EXAMPLE 45, starting with EXAMPLE 42. | |

Example 44

(3R,5S,8S,17E)-8-Cyclohexyl-N-((1R,2S)-1-{[(cyclopropylsulfonyl)amino]carbonyl}-2-vinylcyclopropyl)-24-ethoxy-20-methoxy-7,10-dioxo-2,14-dioxa-6,9,11,23-tetraazapentacyclo[17.6.2.1$^{3,6}$.1$^{11,13}$.0$^{22,26}$]nonacosa-1(25),17,19,21,23,26-hexaene-5-carboxamide

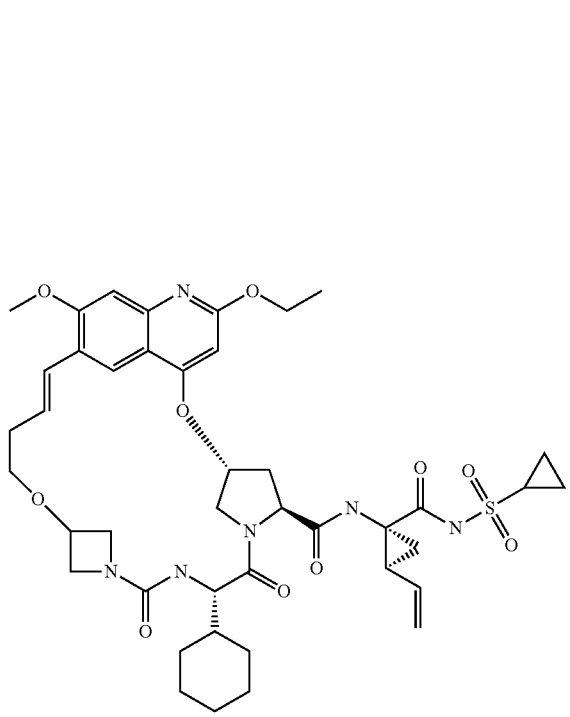 [SMILES: C=C[C@@H]1C[C@]1(NC(=O)[C@@H]1C[C@@H]2CN1C(=O)[C@H](C1CCCCC1)NC(=O)N1CC(C1)OCC/C=C/c1cc3c(cc(OCC)nc3cc1OC)O2)C(=O)NS(=O)(=O)C1CC1]

The title compound was isolated from the reaction mixture containing EXAMPLE 39. This ring contracted byproduct was formed during the ring-closing metathesis reaction described in EXAMPLE 1, step 3. LRMS (M+H)$^+$=835.3. Cell-based HCV Replication Assay: IC$_{50}$ 6 nM.

Example 45

(3R,5S,8S)-8-cyclohexyl-N-((1R,2S)-1-{[(cyclopropylsulfonyl)amino]carbonyl}-2-vinylcyclopropyl)-24-ethoxy-20-methoxy-7,10-dioxo-2,14-dioxa-6,9,11,23-tetraazapentacyclo[17.6.2.1$^{3,6}$.1$^{11,13}$.0$^{22,26}$]nonacosa-1(25),19,21,23,26-pentaene-5-carboxamide

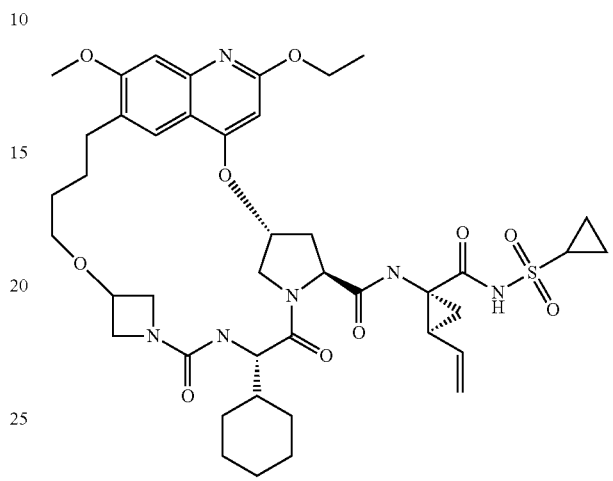

Bismuth(III)chloride (0.015 mL, 0.222 mmol) was added to a solution of EXAMPLE 44 (37.0 mg, 0.044 mmol) in EtOH (10 mL) under nitrogen, and the reaction mixture was cooled in an ice bath. Sodium borohydride (84 mg, 2.216 mmol) was then added, and the reaction mixture was heated to 50° C. oil bath and stirred for 1 h. The reaction mixture was cooled to 0° C. and carefully quenched with 1M HCl dropwise. The mixture was filter through CELITE, rinsed with EtOH and concentrated to a white solid. Water and HCl were added to adjust to pH ~4.5, and the mixture was extracted with EtOAc, dried with anhydrous MgSO$_4$, filtered and concentrated. Purification by reverse-phase chromatography (0.15% trifluoracetic acid/CH$_3$CN gradient and a WATERS SUNFIRE PREP C$_{18}$ ODB 5 µm 30×100 mm column) gave the title compound as a white foam. LRMS (M+H)$^+$=837.3. Cell-based HCV Replication Assay: IC$_{50}$ 6 nM.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

---

What is claimed is:

1. A compound of formula (I):

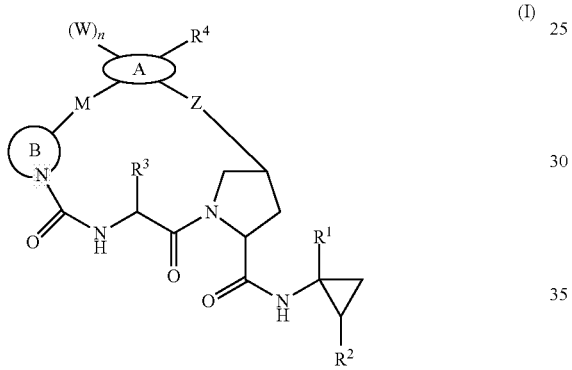

or a pharmaceutically acceptable salt thereof, wherein:

n is 0, 1 or 2;

$R^1$ is selected from the group consisting of $CO_2R^{10}$, $CONR^{10}SO_2R^6$, $CONR^{10}SO_2NR^8R^9$ and tetrazolyl;

$R^2$ is selected from the group consisting of $C_{1-6}$alkyl, $C_{2-6}$alkenyl and $C_{3-8}$cycloalkyl, wherein said $R^2$ alkyl, alkenyl or cycloalkyl is substituted with 0 to 3 halogens;

$R^3$ is selected from the group consisting of $C_{1-8}$alkyl, $C_{3-8}$cycloalkyl, $C_{3-8}$cycloalkyl($C_{1-8}$)alkyl, aryl($C_{1-8}$) alkyl and Het, wherein said $R^3$ alkyl, cycloalkyl, or aryl is substituted with 0 to 3 substituents selected from the group consisting of halogen, $OR^{10}$, $SR^{10}$, $N(R^{10})_2$, $N(C_{1-6}$alkyl$)O(C_{1-6}$alkyl$)$, $C_{1-6}$alkyl, $C_{1-6}$haloalkyl, $C_{1-6}$haloalkoxy, $NO_2$, CN, $CF_3$, $SO_2(C_{1-6}$alkyl$)$, $S(O)(C_{1-6}$alkyl$)$, $NR^{10}SO_2R^6$, $SO_2N(R^6)_2$, $NHCOOR^6$, $NHCOR^6$, $NHCONHR^6$, $CO_2R^{10}$, $C(O)R^{10}$ and $CON(R^{10})_2$;

Het is a 5- to 6-membered saturated cyclic ring having 1 or 2 heteroatoms selected from the group consisting of N, O and S, wherein said ring is substituted with 0 to 3 substituents selected from the group consisting of halogen, $OR^{10}$, $SR^{10}$, $N(R^{10})_2$, $N(C_{1-6}$alkyl$)O(C_{1-6}$alkyl$)$, $C_{1-6}$alkyl, $C_{1-6}$haloalkyl, $C_{1-6}$haloalkoxy, $NO_2$, CN, $CF_3$, $SO_2(C_{1-6}$alkyl$)$, $S(O)(C_{1-6}$alkyl$)$, $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^4$ is selected from the group consisting of H, halogen, OH, $C_{1-6}$alkoxy, $C_{1-6}$alkyl, CN, $CF_3$, $SR^{10}$, $SO_2(C_{1-6}$alkyl$)$, $C_{3-8}$cycloalkyl, $C_{3-8}$cycloalkoxy, $C_{1-6}$haloalkyl, $N(R^7)_2$, aryl, heteroaryl and heterocyclyl; wherein said $R^4$ aryl, heteroaryl, heterocyclyl, cycloalkyl, cycloalkoxy, alkyl or alkoxy is substituted with 0 to 4 substituents selected from the group consisting of halogen, $OR^{10}$, $SR^{10}$, $N(R^7)_2$, $N(C_{1-6}$alkyl$)O(C_{1-6}$alkyl$)$, $C_{1-6}$alkyl, $C_{1-6}$haloalkyl, $C_{1-6}$haloalkoxy, $C_{3-6}$cycloalkyl, $C_{3-6}$cycloalkoxy, $NO_2$, CN, $CF_3$, $SO_2(C_{1-6}$alkyl$)$, $NR^{10}SO_2R^6$, $SO_2N(R^6)_2$, $S(O)(C_{1-6}$alkyl$)$, $NHCOOR^6$, $NHCOR^6$, $NHCONHR^6$, $CO_2R^{10}$, $C(O)R^{10}$ and $CON(R^{10})_2$; wherein 2 adjacent substituents of said $R^4$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;

each $R^6$ is independently selected from the group consisting of $C_{1-6}$alkyl, $C_{3-6}$cycloalkyl, $C_{3-6}$cycloalkyl($C_{1-5}$) alkyl, aryl, aryl($C_{1-4}$alkyl, heteroaryl, heteroaryl($C_{1-4}$ alkyl), heterocyclyl and heterocyclyl($C_{1-8}$alkyl), wherein said $R^6$ alkyl, cycloalkyl, aryl, heteroaryl, or heterocyclyl is substituted with 0 to 2 Q substituents;

each Q is independently selected from the group consisting of halogen, $OR^{10}$, $C_{1-6}$alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_{1-6}$alkyl$)$, $S(O)(C_{1-6}$alkyl$)$, $C_{3-8}$cycloalkyl, $C_{3-8}$cycloalkoxy, $C_{1-6}$haloalkyl, $N(R^{10})_2$, $N(C_{1-6}$alkyl$)O(C_{1-6}$ alkyl$)$, $C_{1-6}$haloalkoxy, $NR^{10}SO_2R^{10}$, $SO_2N(R^{10}SO_2)$, $NHCOOR^{10}$, $NHCONHR^{10}$, aryl, heteroaryl and heterocyclyl;

each $R^7$ is independently selected from the group consisting of H, $C_{1-6}$alkyl, $C_{3-6}$cycloalkyl, $C_{3-6}$cycloalkyl ($C_{1-5}$)alkyl, aryl, aryl($C_{1-4}$alkyl, heteroaryl, heteroaryl ($C_{1-4}$alkyl), heterocyclyl and heterocyclyl($C_{1-8}$alkyl), wherein said $R^7$ alkyl, cycloalkyl, aryl, heteroaryl, or heterocyclyl is substituted with 0 to 2 Q substituents;

$R^8$ is selected from the group consisting of $C_{1-8}$alkyl, $C_{3-8}$cycloalkyl, $C_{3-8}$cycloalkyl($C_{1-8}$alkyl), aryl, aryl ($C_{1-4}$ alkyl), heteroaryl, heterocyclyl, heteroaryl($C_{1-4}$ alkyl) and heterocyclyl($C_{1-8}$alkyl), wherein said $R^8$ alkyl, cycloalkyl, aryl, heteroaryl or heterocyclyl is substituted with 0 to 4 substituents selected from the group consisting of aryl, $C_{3-8}$cycloalkyl, heteroaryl, heterocyclyl, $C_{1-6}$alkyl, $C_{1-6}$haloalkoxy, halo, $OR^{10}$, $SR^{10}$, $N(R^{10})_2$, $N(C_{1-6}$alkyl$)O(C_{1-6}$alkyl$)$, $C_{1-6}$alkyl, $C(O)R^{10}$, $C_{1-6}$haloalkyl, $NO_2$, CN, $CF_3$, $SO_2(C_{1-6}$alkyl$)$, S(O)(C$_{1-6}$alkyl), NR$^{10}$SO$_2$R$^6$, SO$_2$N(R$^6$)$_2$, NHCOOR$^6$, NHCOR$^6$, NHCONHR$^6$, CO$_2$R$^{10}$ and)C(O)N(R$^{10}$SO$_2$; wherein 2 adjacent substituents of said R$^8$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;

R$^9$ is selected from the group consisting of C$_{1-8}$alkyl, C$_{3-8}$cycloalkyl, C$_{3-8}$cycloalkyl(C$_{1-8}$alkyl), C$_{1-8}$alkoxy, C$_{3-8}$cycloalkoxy, aryl, aryl(C$_{1-4}$alkyl), heteroaryl, heterocyclyl, heteroaryl(C$_{1-4}$alkyl) and heterocyclyl(C$_{1-8}$alkyl), wherein said R$^9$ alkyl, cycloalkyl, alkoxy, cycloalkoxy, aryl, heteroaryl or heterocyclyl is substituted with 0 to 4 substituents selected from the group consisting of aryl, C$_{3-8}$cycloalkyl, heteroaryl, heterocyclyl, C$_{1-6}$alkyl, C$_{1-6}$haloalkoxy, halo, OR$^{10}$, SR$^{10}$, N(R$^{10}$)$_2$, N(C$_{1-6}$alkyl)O(C$_{1-6}$alkyl), C$_{1-6}$alkyl, C(O)R$^{10}$, C$_{1-6}$haloalkyl, NO$_2$, CN, CF$_3$, SO$_2$(C$_{1-6}$alkyl), S(O)(C$_{1-6}$alkyl), NR$^{10}$SO$_2$R$^6$, SO$_2$N(R$^6$)$_2$, NHCOOR$^6$, NHCOR$^6$, NHCONHR$^6$, CO$_2$R$^{10}$ and C(O)N(R$^{10}$)$_2$; wherein the 2 adjacent substituents of said R$^9$ cycloalkyl, cycloalkoxy, aryl, heteroaryl or heterocyclyl are optionally taken together to form a 3- to 6-membered cyclic ring containing 0 to 3 heteroatoms selected from the group consisting of N, O and S;

or R$^8$ and R$^9$ are optionally taken together, with the nitrogen atom to which they are attached, to form a 4- to 8-membered monocyclic ring containing 0 to 2 additional heteroatoms selected from the group consisting of N, O and S;

each R$^{10}$ is independently selected from the group consisting of H and C$_{1-6}$alkyl;

Z is C$_{1-6}$alkylene, C$_{0-5}$alkylene-O—, C$_{0-5}$alkylene-NR$^{10}$—, C$_{2-6}$alkenylene, C$_{2-5}$alkenylene-O—, C$_{2-5}$alkenylene-NR$^{10}$—, C$_{2-6}$alkynylene, C$_{2-5}$alkynylene-O—, C$_{2-5}$alkynylene-NR$^{10}$—, C$_{0-3}$alkylene-C(O)O—, C$_{0-3}$alkylene-C(O)—NR$^{10}$, C$_{0-3}$alkylene-O—C(O)—NR$^{10}$— and C$_{0-3}$alkylene-NR$^{10}$—C(O)O—, each substituted by 0 to 2 C$_{1-4}$alkyl;

ring B is selected from the group consisting of N-linked 4- to 9-membered heterocycles containing one N atom, containing 0 or 1 additional heteroatom selected from N, O and S, and substituted by 0 to 2 R$^{10}$;

each W is independently selected from the group consisting of halogen, OR$^{10}$, C$_{1-6}$alkyl, CN, NO$_2$, CF$_3$, CO$_2$R$^{10}$, CON(R$^{10}$)$_2$, COR$^{10}$, NR$^5$C(O)R$^{10}$, aryl and heteroaryl;

M is selected from the group consisting of C$_{3-9}$alkylene, C$_{3-9}$alkenylene and C$_{3-9}$alkynylene, substituted by 0 to 3 substituents selected from the group consisting of C$_{1-6}$alkyl, (CH$_2$)$_{0-3}$C$_{3-8}$cycloalkyl and (CH$_2$)$_{0-3}$aryl, and containing 0 or 1 member selected from the group consisting of O, S and NR$^{10}$ group; and ring A is selected from the group consisting of 8- to 14-membered fused carbobi- and carbotricyclic ring systems, containing 0 to 4 heteroatoms selected from N, O and S.

2. The compound according to claim 1, wherein n is 0 or 1.

3. The compound according to claim 1, wherein R$^1$ is selected from the group consisting of CONR$^{10}$SO$_2$R$^6$ and CONR$^{10}$SO$_2$NR$^8$R$^9$.

4. The compound according to claim 1, wherein R$^2$ is selected from the group consisting of C$_{1-6}$alkyl and C$_{2-6}$alkenyl, substituted with 0 to 3 halogens selected from the group consisting of fluoro and chloro.

5. The compound according to claim 1, wherein R$^3$ is selected from the group consisting of C$_{1-6}$alkyl, (CH$_2$)$_{0-3}$C$_{3-8}$cycloalkyl, (CH$_2$)$_{0-3}$aryl and Het, substituted by 0 to 3 substituents selected from the group consisting of halo, OR$^{10}$, SR$^{10}$, N(R$^{10}$)$_2$, C$_{1-6}$alkyl, NO$_2$, CN, CF$_3$, NR$^{10}$SO$_2$R$^6$, SO$_2$N(R$^6$)$_2$, NHC(O)OR$^6$, NHC(O)R$^6$, NHC(O)NHR$^6$, CO$_2$R$^{10}$, C(O)R$^{10}$ and)C(O)N(R$^{10}$SO$_2$.

6. The compound according to claim 1, wherein each W is independently selected from the group consisting of halo, OR$^{10}$, C$_{1-6}$alkyl, CN, NO$_2$, CF$_3$, CO$_2$R$^{10}$ or CON(R$^{10}$)$_2$.

7. The compound according to claim 1, wherein Z is selected from the group consisting of C$_{0-5}$alkylene-O—, C$_{0-5}$alkylene-NR$^{10}$—, C$_{2-5}$alkenylene-O—, C$_{2-5}$alkenylene-NR$^{10}$, C$_{2-5}$alkylylene-O—, C$_{2-5}$alkynylene-NR$^{10}$— and C$_{0-3}$alkylene-C(O)—O—, substituted by 0 to 2 C$_{1-4}$alkyl.

8. The compound according to claim 1, wherein ring B is selected from the group consisting of N-linked 4- to 8-membered heterocycles containing one N atom, containing 0 or 1 further heteroatom selected from the group consisting of N or O, and substituted by 0 to 2 R$^{10}$.

9. The compound according to claim 1, wherein M is selected from the group consisting of C$_{3-8}$alkylene, C$_{3-8}$alkenylene and C$_{3-8}$alkynylene, substituted by 0 to 2 C$_{1-6}$alkyl, and containing 0 or 1 group selected from the group consisting of O atom and NR$^{10}$ group.

10. The compound according to claim 1, wherein ring A is selected from the group consisting of 8- to 14-membered fused carbobi- and carbotricyclic ring systems, containing 0 to 3 heteroatoms selected from the group consisting of N and O, and substituted by 0 to 4 R$^4$.

11. The compound according to claim 1, wherein R$^4$ is selected from the group consisting of halo, hydroxy, C$_{1-6}$alkyl, C$_{1-6}$alkoxy, CN, C$_{3-8}$cycloalkyl, N(R$^7$)$_2$, aryl and heteroaryl, substituted by 0 to 4 halo or C$_{1-4}$alkyl.

12. The compound according to claim 1, wherein the compound of formula (I) is a compound of formula (Ia):

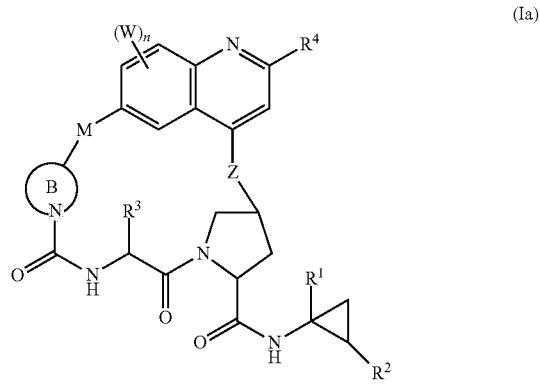

(Ia)

or a pharmaceutically acceptable salt thereof.

13. The compound according to claim 1, wherein the compound of formula (I) is a compound of formula (Ib):

111

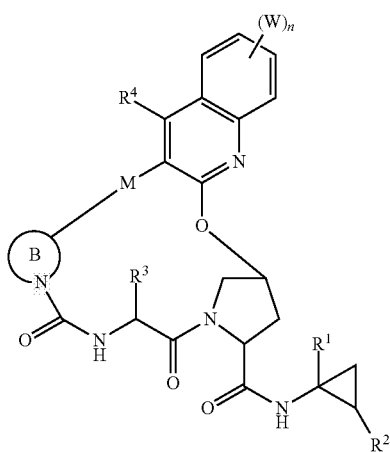

(Ib)

or a pharmaceutically acceptable salt thereof.

14. The compound according to claim 1, wherein the compound of formula (I) is a compound of formula (Ic):

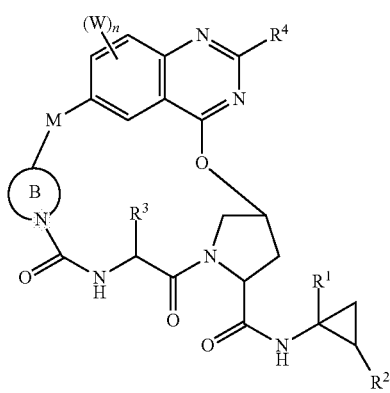

(Ic)

or a pharmaceutically acceptable salt thereof.

15. The compound according to claim 1, wherein the compound of formula (I) is a compound of formula (Id):

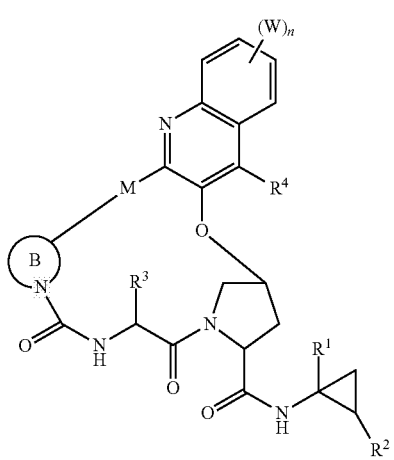

(Id)

or a pharmaceutically acceptable salt thereof.

112

16. The compound according to claim 1, wherein the compound of formula (I) is a compound of formula (Ie):

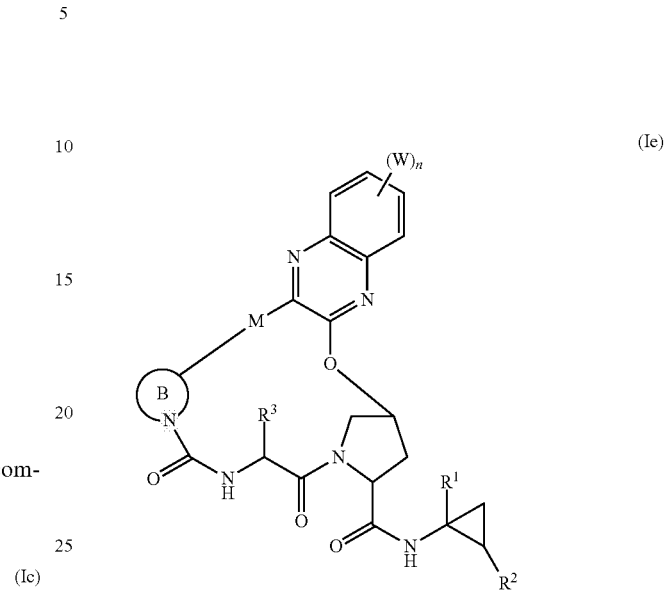

(Ie)

or a pharmaceutically acceptable salt thereof.

17. The compound according to claim 1, wherein the compound of formula (I) is a compound of formula (If):

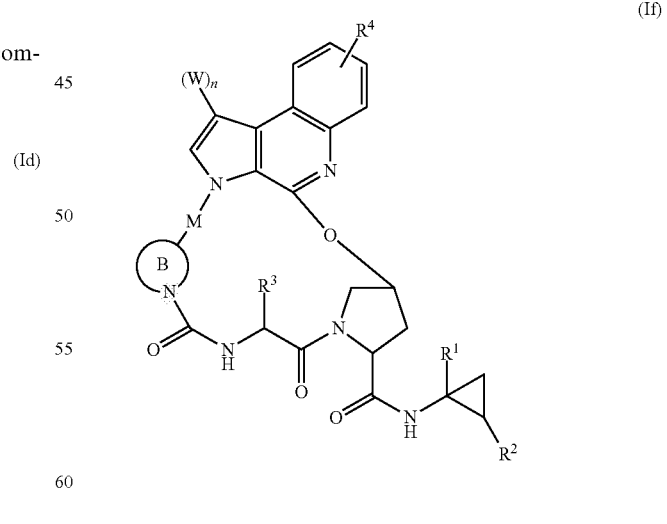

(If)

or a pharmaceutically acceptable salt thereof.

18. The compound according to claim 1, wherein the compound of formula (I) is a compound of formula (Ig):

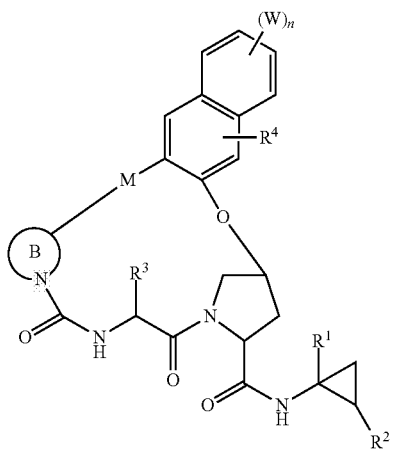

(Ig)

or a pharmaceutically acceptable salt thereof.

19. The compound according to claim 1, wherein the compound of formula (I) is a compound of formula (Ih):

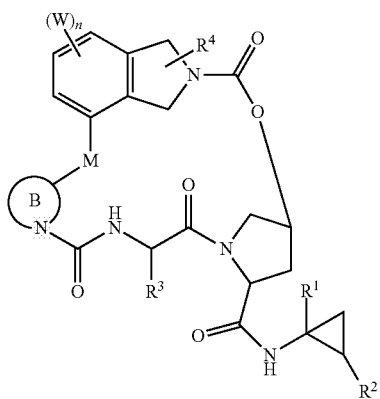

(Ih)

or a pharmaceutically acceptable salt thereof.

20. The compound according to claim 1, wherein the compound of formula (I) is a compound of formula (II):

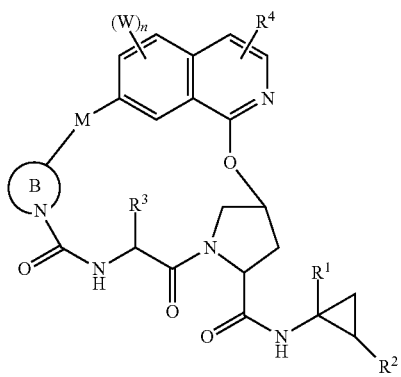

(Ii)

or a pharmaceutically acceptable salt thereof.

21. The compound according to claim 1, wherein the compound of formula (I) is a compound of formula (Ij):

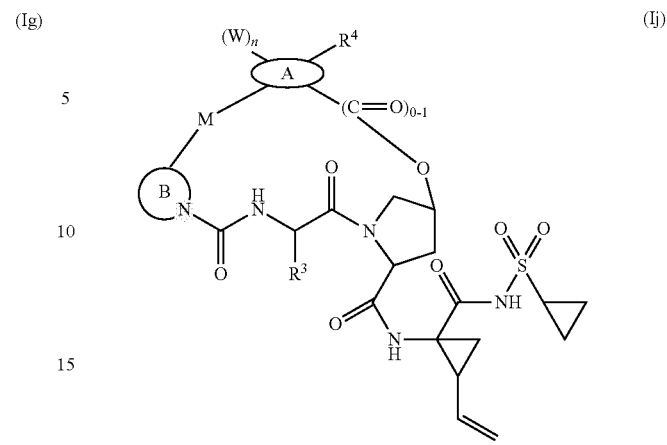

(Ij)

or a pharmaceutically acceptable salt thereof.

22. The compound according to claim 1, wherein the compound is selected from the group consisting of:

(3R,5S,8S,15S)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide, (2R,4S,7S,13S,18E)-7-cyclopentyl-N-((1R,2S)-1-{[(cyclopropylsulfonyl)amino]carbonyl}-2-vinylcyclopropyl)-6,9-dioxo-3,4,6,7,8,9,12,13,16,17-decahydro-2H,11H,15H-2,5:10,13-dimethano[1,14,5,7,10]dioxatriazacyclohenicosino[15,16-b]quinoxaline-4-carboxamide, (1R,12E,16S,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10,12-tetraene-26-carboxamide, (1R,12E,16R,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10,12-tetraene-26-carboxamide, (1R,16R,23S,26S)-23-tert-butyl-N-((1R,2S)-1-{[(cyclopropylsulfonyl)amino]carbonyl}-2-vinylcyclopropyl)-3,21,24-trioxo-2-oxa-4,20,22,25-tetraazapentacyclo[23.2.1.1$^{4,7}$.0$^{6,11}$.0$^{16,20}$]nonacosa-6,8,10-triene-26-carboxamide, (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-25-phenyl-2-oxa-6,9,11,24-tetraazapentacyclo[18.6.2.1$^{3,6}$.1$^{11,15}$.0$^{23,27}$]triaconta-1(27),20,22,23,25,27-hexaene-5-carboxamide, (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-25-phenyl-2-oxa-6,9,11,24-tetraazapentacyclo[18.6.2.1$^{3,6}$.1$^{11,15}$.0$^{23,27}$]triaconta-1(27),20,22,23,25,27-hexaene-5-carboxamide, (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-25-phenyl-2,16-dioxa-6,9,11,24-tetraazapentacyclo[18.6.2.1$^{3,6}$.1$^{11,15}$.0$^{23,27}$]triaconta-1(27),20,22,23,25,27-hexaene-5-carboxamide, (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-25-phenyl-2,16-dioxa-6,9,11,24- tetraazapentacyclo[18.6.2.1$^{3,6}$.1$^{11,15}$.0$^{23,27}$]triaconta-1 (27),20,22,23,25,27-hexaene-5-carboxamide, (3R,5S,8S,15S)-8-cyclohexyl-N-((1R,2S)-1-{[(cyclopropylsulfonyl)amino]carbonyl}-2-vinylcyclopropyl)-21-methoxy-7,10-dioxo-2,16-dioxa-6,9,11,26-tetraazapentacyclo[18.6.2.1$^{3,6}$.1$^{11,15}$.0$^{23,27}$]triaconta-1(26),20, 22,24,27-pentaene-5-carboxamide, (3R,5S,8S,15R)-8-cyclohexyl-N-((1R,2S)-1-{[(cyclopropylsulfonyl)amino]carbonyl}-2-vinylcyclopropyl)-21-methoxy-7,10-dioxo-2,16-dioxa-6,9,11,26-tetraazapentacyclo[18.6.2.1$^{3,6}$.1$^{11,15}$.0$^{23,27}$]triaconta-1(26),20, 22,24,27-pentaene-5-carboxamide, (3R,5S,8S,15R)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,16-dioxa-6,9,11,24-tetraazapentacyclo[18.6.2.1$^{3,6}$.1$^{11,15}$.0$^{23,27}$]triaconta-1 (27),20,22,23,25,27-hexaene-5-carboxamide, (3R,5S,8S,14S,17E)-8-cyclohexyl-N-((1R,2S)-1-{[(cyclopropylsulfonyl)amino]carbonyl}-2-vinylcyclopropyl)-24-ethoxy-20-methoxy-7,10-dioxo-2,15-dioxa-6, 9,11,23-tetraazapentacyclo[17.6.2.1$^{3,6}$.1$^{11,14}$.0$^{22,26}$] nonacosa-1(25),17,19,21,23,26-hexaene-5-carboxamide, (4S,7S,9R,21E,27R)-4-cyclopentyl-N-((1R,2S)-1-{[(cyclopropylsulfonyl)amino]carbonyl}-2-vinylcyclopropyl)-2,5-dioxo-10,26-dioxa-1,3,6,19-tetraazapentacyclo[25.3.1.1$^{6,9}$.0$^{11,20}$.0$^{13,18}$]dotriaconta-11(20),12,13, 15,17,18,21-heptaene-7-carboxamide, (3R,5S,8S,18E)-8-cyclopentyl-N-((1R,2S)-1-{[(cyclopropylsulfonyl)amino]carbonyl}-2-vinylcyclopropyl)-23-methyl-7,10-dioxo-2,16-dioxa-6,9,11,21,31-pentaazahexacyclo[19.10.1.1$^{3,6}$.1$^{11,15}$.0$^{24,32}$.0$^{25,30}$] tetratriaconta-1(31),18,22,24(32),25,27,29-heptaene-5-carboxamide, (4S,7S,9R,27S)-4-cyclopentyl-N-((1R,2S)-1-{[(cyclopropylsulfonyl)amino]carbonyl}-2-vinylcyclopropyl)-2,5-dioxo-10,26-dioxa-1,3,6,19-tetraazapentacyclo [25.3.1.1$^{6,9}$.0$^{11,20}$. 0$^{13,18}$]dotriaconta-11(20),12,13,15, 17,18-hexaene-7-carboxamide, (1R,13E,19S,25S,28S)-25-cyclopentyl-N-((1R,2S)-1-{ [(cyclopropylsulfonyl)amino]carbonyl}-2-vinylcyclopropyl)-7-methoxy-23,26-dioxo-2,18-dioxa-4,22,24, 27-tetraazapentacyclo[25.2.1.1$^{19,22}$.0$^{3,12}$.0$^{5,10}$] hentriaconta-3(12),4,5,7,9,10,13-heptaene-28-carboxamide, (1R,19S,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$] hentriaconta-3(12),4,5,7,9,10-hexaene-28-carboxamide, (1R,13E,19S,25S,28S)-25-cyclopentyl-((N1R,2R)-1-{ [(cyclopropylsulfonyl)amino]carbonyl}-2-ethylcyclopropyl)-7-methoxy-23,26-dioxo-2,18-dioxa-4,22,24, 27-tetraazapentacyclo[25.2.1.1$^{19,22}$.0$^{3,12}$.0$^{5,10}$] hentriaconta-3(12),4,5,7,9,10,13-heptaene-28-carboxamide, (1R,19S,25S,28S)-25-cyclopentyl-N-((1R,2R)-1-{[(cyclopropylsulfonyl)amino]carbonyl}-2-ethylcyclopropyl)-7-methoxy-23,26-dioxo-2,18-dioxa-4,22,24,27-tetraazapentacyclo[25.2.1.1$^{19,22}$.0$^{3,12}$.0$^{5,10}$] hentriaconta-3(12),4,5,7,9,10-hexaene-28-carboxamide, (1R,13E,19R,25S,28S)-25-cyclopentyl-N-((1R,2S)-1-{ [(cyclopropylsulfonyl)amino]carbonyl}-2-vinylcyclopropyl)-7-methoxy-23,26-dioxo-2,18-dioxa-4,22,24, 27-tetraazapentacyclo[25.2.1.1$^{19,22}$.0$^{3,12}$.0$^{5,10}$] hentriaconta-3(12),4,5,7,9,10,13-heptaene-28-carboxamide, (3R,5S,8S,14S,17E)-8-cyclopentyl-N-((1R,2S)-1-{[(cyclopropylsulfonyl)amino]carbonyl}-2-vinylcyclopropyl)-24-ethoxy-20-methoxy-7,10-dioxo-2,15-dioxa-6, 9,11,23-tetraazapentacyclo[17.6.2.1$^{3,6}$.1$^{11,14}$.0$^{22,26}$] nonacosa-1(25),17,19,21,23,26-hexaene-5-carboxamide, (3R,5S,8S,14S,17E)-8-cyclopentyl-N-((1R,2R)-1-{[(cyclopropylsulfonyl)amino]carbonyl}-2-ethylcyclopropyl)-24-ethoxy-20-methoxy-7,10-dioxo-2,15-dioxa-6, 9,11,23-tetraazapentacyclo[17.6.2.1$^{3,6}$.1$^{11,14}$.0$^{22,26}$] nonacosa-1(25),17,19,21,23,26-hexaene-5-carboxamide, (2R,4S,7S,13S)-7-cyclopentyl-N-((1R,2S)-1-{[(cyclopropylsulfonyl)amino]carbonyl}-2-vinylcyclopropyl)-6,9-dioxo-3,4,6,7,8,9,12,13,16,17,18,19-dodecahydro-2H,11H,15H-2,5:10,13-dimethano[1,14,5,7,10] dioxatriazacyclohenicosino[15,16-b]quinoxaline-4-carboxamide, (1R,18S,24S,27S)-24-cyclopentyl-N-((1R,2S)-1-{[(cyclopropylsulfonyl)amino]carbonyl}-2-vinylcyclopropyl)-7-methoxy-22,25-dioxo-2,16-dioxa-11,21,23,26-tetraazapentacyclo[24.2.1.1$^{18,21}$.0$^{3,12}$.0$^{5,10}$]triaconta-3 (12),4,5,7,9,10-hexaene-27-carboxamide, (2R,4S,7S,13S)-7-cyclopentyl-N-((1R,2S)-1-{[(cyclopropylsulfonyl)amino]carbonyl}-2-vinylcyclopropyl)-23-methoxy-6,9-dioxo-3,4,6,7,8,9,11,12,13,14,16,17, 18,19-tetradecahydro-2H-2,5:10,13-dimethano[1,15,5, 8,10]dioxatriazacyclohenicosino[20,21-b]quinoline-4-carboxamide, (6R,8S,11S,17aR)-11-cyclopentyl-N-((1R,2S)-1-{[(cyclopropylsulfonyl)amino]carbonyl}-2-vinylcyclopropyl)-3-ethoxy-10,13-dioxo-7,8,10,11,12,13,16,17,17a, 18,20,21-dodecahydro-6H,15H-1,22-(ethanediylidene)-6,9-methanopyrimido[4,5-n]pyrrolo [2,1-c][1,13,4,6,9]dioxatriazacyclononadecine-8-carboxamide, (6R,8S,11S,17aS,20E)-11-cyclopentyl-N-((1R,2S)-1-{ [(cyclopropylsulfonyl)amino]carbonyl}-2-vinylcyclopropyl)-3-ethoxy-10,13-dioxo-7,8,10,11,12,13,16,17, 17a,18-decahydro-6H,15H-1,22-(ethanediylidene)-6, 9-methano pyrimido[4,5-n]pyrrolo[2,1-c][1,13,4,6,9] dioxatriazacyclononadecine-8-carboxamide, (6R,8S,11S,17a5)-11-cyclopentyl-N-((1R,2S)-1-{[(cyclopropylsulfonyl)amino]carbonyl}-2-vinylcyclopropyl)-3-ethoxy-10,13-dioxo-7,8,10,11,12,13,16,17,17a, 18,20,21-dodecahydro-6H,15H-1,22-(ethanediylidene)-6,9-methanopyrimido[4,5-n]pyrrolo [2,1-c][1,13,4,6,9]dioxatriazacyclononadecine-8-carboxamide, (4E,8S,14S,17S,19R)-14-cyclopentyl-N-((1R,2S)-1-{ [(cyclopropylsulfonyl)amino]carbonyl}-2-vinylcyclopropyl)-1-methyl-12,15-dioxo-3,6,9,10,12,13,14,15, 18,19-decahydro-8H,17H-8,11:16,19-dimethano-7,20-dioxa-2a,11,13,16,21-pentaazabenzo[g]cyclohenicosa [1,2,3-cd]indene-17-carboxamide, (3R,5S,8S,19E)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,15-dioxa-6,9,11,25-tetraazapentacyclo[19.6.2.2$^{11,14}$.1$^{3,6}$.0$^{24,28}$] dotriaconta-1(27),19,21,23,25,28-hexaene-5-carboxamide, (1R,18S,24S,27S)-24-cyclopentyl-N-((1R,2S)-1-{[(cyclopropylsulfonyl)amino]carbonyl}-2-vinylcyclopropyl)-7-methoxy-22,25-dioxo-2,16-dioxa-11,21,23,26- tetraazapentacyclo[24.2.1.1$^{18,21}$.0$^{3,12}$.0$^{5,10}$]triaconta-3 (12),4,5,7,9,10-hexaene-27-carboxamide, (3R,5S,8S)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,15-dioxa-6,9,11,25-tetraazapentacyclo[19.6.2.2$^{11,14}$.1$^{3,6}$.0$^{24,28}$]dotriaconta-1(27),21,23,25,28-pentaene-5-carboxamide, (4S,7S,9R,21E)-4-cyclohexyl-N-((1R,2S)-1-{[(cyclopropylsulfonyl)amino]carbonyl}-2-vinylcyclopropyl)-15-methoxy-2,5-dioxo-10,26-dioxa-1,3,6,12-tetraazapentacyclo[25.2.2.1$^{6,9}$.0$^{11,20}$.0$^{13,18}$]dotriaconta-11(20),12,13,15,17,18,21-heptaene-7-carboxamide, (1R,13E,24S,27S)-24-cyclohexyl-N-((1R,2S)-1-{[(cyclopropylsulfonyl)amino]carbonyl}-2-vinylcyclopropyl)-7-methoxy-22,25-dioxo-2,18-dioxa-4,21,23,26-tetraazapentacyclo[24.2.1.1$^{19,21}$.0$^{3,12}$.0$^{5,10}$]triaconta-3 (12),4,5,7,9,10,13-heptaene-27-carboxamide, (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10,13-heptaene-28-carboxamide, (1R,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10-hexaene-28-carboxamide, (3R,5S,8S,18E)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,14-dioxa-6,9,11,24-tetraazapentacyclo[18.6.2.1$^{3,6}$.1$^{11,13}$.0$^{23,27}$]triaconta-1(26),18,20,22,24,27-hexaene-5-carboxamide, (3R,5S,8S,14S)-8-cyclopentyl-N-((1R,2S)-1-{[(cyclopropylsulfonyl)amino]carbonyl}-2-vinylcyclopropyl)-24-ethoxy-7,10-dioxo-2,15-dioxa-6,9,11,23,25-pentaazapentacyclo[17.6.2.1$^{3,6}$.1$^{11,14}$.0$^{22,26}$]nonacosa-1(25),17,19,21,23,26-hexaene-5-carboxamide, (3R,5S,8S,14S)-8-cyclopentyl-N-((1R,2S)-1-{[(cyclopropylsulfonyl)amino]carbonyl}-2-vinylcyclopropyl)-24-ethoxy-7,10-dioxo-2,15-dioxa-6,9,11,23,25-pentaazapentacyclo[17.6.2.1$^{3,6}$.1$^{11,14}$.0$^{22,26}$]nonacosa-1(25),19,21,23,26-pentaene-5-carboxamide, (1R,13E,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide, (1R,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide, (3R,5S,8S,17E)-8-cyclohexyl-N-((1R,2S)-1-{[(cyclopropylsulfonyl)amino]carbonyl}-2-vinylcyclopropyl)-24-ethoxy-20-methoxy-7,10-dioxo-2,14-dioxa-6,9,11,23-tetraazapentacyclo[17.6.2.1$^{3,6}$.1$^{11,13}$.0$^{22,26}$]nonacosa-1(25),17,19,21,23,26-hexaene-5-carboxamide, (3R,5S,8S)-8-cyclohexyl-N-((1R,2S)-1-{[(cyclopropylsulfonyl)amino]carbonyl}-2-vinylcyclopropyl)-24-ethoxy-20-methoxy-7,10-dioxo-2,14-dioxa-6,9,11,23-tetraazapentacyclo[17.6.2.1$^{3,6}$.1$^{11,13}$.0$^{22,26}$]nonacosa-1(25),19,21,23,26-pentaene-5-carboxamide, and pharmaceutically acceptable salts thereof.

23. A pharmaceutical composition comprising a compound of claim 1, or a pharmaceutically acceptable salt thereof, in association with a pharmaceutically acceptable carrier.

24. The pharmaceutical composition as claimed in claim 23, further comprising one or more other agents for the treatment of viral infections selected from the group consisting of an antiviral agent, an immunomodulatory agent, α-interferon, β-interferon and γ-interferon.

25. A method of inhibiting hepatitis C virus protease and/or of treating a hepatitis C virus infection, the method involving administering to a human or animal subject suffering from the infection a therapeutically effective amount of a compound of claim 1, or a pharmaceutically acceptable salt thereof.

26. A method of inhibiting hepatitis C virus protease and/or of treating a hepatitis C virus infection, the method involving administering to a human or animal subject suffering from the infection a therapeutically effective amount of the pharmaceutical composition as claimed in claim 23.

* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Protease Substrate
<221> NAME/KEY: ACETYLATION
<222> LOCATION: 1
<221> NAME/KEY: AMIDATION
<222> LOCATION: 11
```

```
<221> NAME/KEY: SITE
<222> LOCATION: 1
<223> OTHER INFORMATION: Europium label
<221> NAME/KEY: MOD_RES
<222> LOCATION: 7
<223> OTHER INFORMATION: Xaa = Abu
<221> NAME/KEY: SITE
<222> LOCATION: 8
<223> OTHER INFORMATION: Xaa = 2-hydroxy propanoic acid
<221> NAME/KEY: SITE
<222> LOCATION: (11)...(11)
<223> OTHER INFORMATION: QSY-7 label
<221> NAME/KEY: THIOLEST
<222> LOCATION: (7)...(8)

<400> SEQUENCE: 1

Cys Asp Asp Met Glu Glu Xaa Xaa Ser Ala Lys
1               5                   10
```